United States Patent
Orringer et al.

(10) Patent No.: US 11,419,590 B2
(45) Date of Patent: Aug. 23, 2022

(54) BIOPSY DEVICE FOR COHERENT RAMAN IMAGING

(71) Applicants: THE REGENTS OF THE UNIVERSITY OF MICHIGAN, Ann Arbor, MI (US); INVENIO IMAGING, INC., Santa Clara, CA (US)

(72) Inventors: Daniel Orringer, New York, NY (US); Christian Freudiger, San Carlos, CA (US); Jay Trautman, Los Altos, CA (US); Andrew Kelly, Boise, ID (US)

(73) Assignees: THE REGENTS OF THE UNIVERSITY OF MICHIGAN, Ann Arbor, MI (US); INVENIO IMAGING, INC., Santa Clara, CA (US)

( * ) Notice: Subject to any disclaimer, the term of this patent is extended or adjusted under 35 U.S.C. 154(b) by 43 days.

(21) Appl. No.: 16/994,327

(22) Filed: Aug. 14, 2020

(65) Prior Publication Data

US 2020/0375580 A1    Dec. 3, 2020

Related U.S. Application Data

(63) Continuation of application No. 15/762,904, filed as application No. PCT/US2016/053481 on Sep. 23, 2016, now Pat. No. 10,743,848.

(Continued)

(51) Int. Cl.
*G01J 3/02*       (2006.01)
*A61B 10/02*      (2006.01)
(Continued)

(52) U.S. Cl.
CPC .......... *A61B 10/0283* (2013.01); *A61B 10/02* (2013.01); *G01J 3/44* (2013.01);
(Continued)

(58) Field of Classification Search
CPC ..... A61B 10/0283; A61B 10/02; A61B 10/04; G01J 3/44; G01J 3/0205; G01N 21/65; G01N 2021/653
See application file for complete search history.

(56) References Cited

U.S. PATENT DOCUMENTS 6,108,081 A    8/2000  Holtom et al.
6,411,434 B1   6/2002  Eastman et al.
(Continued)

FOREIGN PATENT DOCUMENTS

CN    101959450 A    1/2011
CN    102266250 A    12/2011
(Continued)

OTHER PUBLICATIONS

Office Action regarding Chinese Patent Application No. 201680062468.0, dated Jun. 2, 2021. Translation provided by Unitalen Attorneys at Law.

(Continued)

*Primary Examiner* — Abdullahi Nur
(74) *Attorney, Agent, or Firm* — Harness, Dickey & Pierce, P.L.C.

(57) ABSTRACT

Devices and systems for analyzing biological samples are provided. Devices include a hollow body extending from a first end to a second end. The body defines a sample collecting portion. A first opening at the first end of the body is operable to receive a source of negative pressure and a second opening at the second end of the body is operable to receive a biological sample. The body also includes an optically transparent region disposed in a region correspond- (Continued)

ing to the sample collecting portion, the optically transparent region being configured to transmit electromagnetic radiation therethrough from an imaging device capable of imaging the biological sample when disposed in the sample collecting portion.

20 Claims, 37 Drawing Sheets

Related U.S. Application Data

(60) Provisional application No. 62/232,633, filed on Sep. 25, 2015.

(51) Int. Cl.
   *G01J 3/44* (2006.01)
   *G01N 21/65* (2006.01)
   *A61B 10/04* (2006.01)

(52) U.S. Cl.
   CPC .............. *G01N 21/65* (2013.01); *A61B 10/04* (2013.01); *G01J 3/0205* (2013.01); *G01N 2021/653* (2013.01)

(56) References Cited

U.S. PATENT DOCUMENTS

| | | | |
|---|---|---|---|
| 6,809,814 | B2 | 10/2004 | Xie et al. |
| 7,194,118 | B1 | 3/2007 | Harris et al. |
| 7,227,630 | B1 | 6/2007 | Zavislan et al. |
| 7,414,729 | B2 | 8/2008 | Xie et al. |
| 7,854,705 | B2 | 12/2010 | Pawluczyk et al. |
| 8,027,032 | B2 | 9/2011 | Xie et al. |
| 8,115,918 | B2 | 2/2012 | Zavislan et al. |
| 2003/0187324 | A1* | 10/2003 | Gatto .................. A61B 1/3132 600/101 |
| 2004/0147033 | A1 | 7/2004 | Shriver et al. |
| 2008/0243031 | A1* | 10/2008 | Seibel .................... A61B 10/02 600/566 |
| 2010/0191266 | A1 | 7/2010 | Oliver et al. |
| 2010/0331782 | A1 | 12/2010 | Hendriks et al. |
| 2012/0068085 | A1 | 3/2012 | Cucin |
| 2012/0259229 | A1 | 10/2012 | Wang et al. |
| 2014/0316255 | A1 | 10/2014 | Garai et al. |
| 2014/0354987 | A1 | 12/2014 | Satoh et al. |
| 2015/0121660 | A1 | 5/2015 | Li |
| 2015/0182204 | A1 | 7/2015 | Yazdanfar et al. |
| 2015/0204790 | A1 | 7/2015 | Yonetani |
| 2016/0103072 | A1 | 4/2016 | Fukutake et al. |

FOREIGN PATENT DOCUMENTS

| | | |
|---|---|---|
| JP | H1195119 A | 4/1999 |
| JP | 2004254742 A | 9/2004 |
| JP | 2006515927 A | 6/2006 |
| JP | 2013514520 A | 4/2013 |
| JP | 2015006321 A | 1/2015 |
| JP | 2015121660 A | 7/2015 |
| WO | WO-2012088167 A2 | 6/2012 |
| WO | WO-2013032839 A2 | 3/2013 |
| WO | WO-2013166497 A1 | 11/2013 |
| WO | 2014131904 A1 | 9/2014 |
| WO | WO-2014162744 A1 | 10/2014 |
| WO | WO-2015042460 A1 | 3/2015 |

OTHER PUBLICATIONS

Hu, Chun-Rui, "Application of Stimulated Raman Scattering (SRS) Microscopy to Quick Detection of and Guiding Removal Surgery of Tumors." In: Label-Free Myelin Imaging by Stimulated Raman Scattering Microscopy and Stimulated Raman Scattering Imaging by Continuous Wave Laser Excitation, China Doctoral Dissertations Full-Text Database Basic Sciences, No. 10, A006-1, pp. 33-35 (Oct. 15, 2014).

Office Action regarding Chinese Patent Application No. 201680062468. 0, dated Dec. 28, 2020. Translation provided by Unitalen Attorneys at Law.

Office Action regarding European Patent Application No. 16774829. 2, dated Feb. 25, 2021.

International Search Report and Written Opinion regarding International Application No. PCT/US2016/053481, dated Dec. 22, 2016; ISA/EP.

Office Action regarding Japanese Patent Application No. 2018-536066, dated Mar. 3, 2020. Translation provided by Asamura Patent Office, p.c.

Office Action regarding Chinese Patent Application No. 201680062468. 0, dated May 6, 2020. Translation provided by Unitalen Attorneys at Law.

Berkels, Benjamin et al., "Co-registration of intra-operative brain surface photographs and pre-operative MR images." International Journal of Computer Assisted Radiology and Surgery, vol. 9, No. 3, pp. 387-400 (2014).

Freudiger, Christian W. et al., "Label-Free Biomedical Imaging with High Sensitivity by Stimulated Raman Scattering Microscopy." Science, vol. 322, No. 5909, pp. 1857-1861 (2008).

Freudiger, Christian W. et al., "Multicolored stain-free histopathology with coherent Raman imaging." Laboratory Investigation, vol. 92, No. 10, pp. 1492-1502 (2012).

Freudiger, Christian W. et al., "Stimulated Raman scattering microscopy with a robust fibre laser source." Nature Photonics, vol. 8, No. 2, pp. 153-159 (2014).

Jermyn, Michael et al., "Intraoperative brain cancer detection with Raman spectroscopy in humans." Science Translational Medicine, vol. 7, No. 274, 274ra19 (2015).

Ji, Minbiao et al., "Detection of human brain tumor infiltration with quantitative stimulated Raman scattering microscopy." Science Translational Medicine, vol. 7, No. 309, 309ra163 (2015).

Ji, Minbiao et al., "Rapid, Label-Free Detection of Brain Tumors with Stimulated Raman Scattering Microscopy." Science Translational Medicine, vol. 5, No. 201, 201ra119 (2013).

Makary, Mina et al., "Clinical and Economic Outcomes of Low-Field Intraoperative MRI-Guided Tumor Resection Neurosurgery." Journal of Magnetic Resonance Imaging, vol. 34, No. 5, pp. 1022-1030 (2011).

Picard, Richard R. and Cook, R. Dennis, "Cross-Validation of Regression Models." Journal of the American Statistical Association, vol. 79, No. 387, pp. 575-583 (1984).

Saar, Brian G. et al., "Video-Rate Molecular Imaging in Vivo with Stimulated Raman Scattering." Science, vol. 330, No. 6009, pp. 1368-1370 (2010).

Satoh, Shuya et al., "Label-free visualization of acetaminophen-induced liver injury by high-speed stimulated Raman scattering spectral microscopy and multivariate image analysis." Pathology International, vol. 64, No. 10, pp. 518-526 (2014).

Senft, Christian et al., "Intraoperative MRI guidance and extent of resection in glioma surgery: a randomised, controlled trial." The Lancet Oncology, vol. 12, No. 11, pp. 997-1003 (2011).

Willems, P.W. et al., "Effectiveness of neuronavigation in resecting solitary intracerebral contrast-enhancing tumors: a randomized controlled trial." Journal of Neurosurgery, vol. 104, No. 3, pp. 360-368 (2006).

Zuschratter, Werner et al., "Acquisition of multiple image stacks with a confocal laser scanning microscope." Proceedings of Three-Dimensional and Multidimensional Microscopy: Image Acquisition and Processing V, Proceedings of SPIE, vol. 3261, pp. 177-186 (1998).

Office Action regarding Japanese Patent Application No. 2020-093824, dated Jul. 29, 2021. Translation provided by Asamura Patent Office, p.c.; 9 pages.

U.S. Appl. No. 15/762,904, filed Mar. 23, 2018.

International Search Report and Written Opinion regarding corresponding International Application No. PCT/US2016/053481 dated Dec. 22, 2016 citing U.S. Pub. No. 2014/0354987; WO 2012/

(56) References Cited

OTHER PUBLICATIONS

088167 A2 and U.S. Pub. No. 2012/0068085; U.S. Pub. No. 2010/0191266; and WO 2013/032839 A2.

Office Action regarding corresponding Japanese Patent Application No. 2018-536066 dated Mar. 3, 2020 citing Satoh, Shuya et al., "Label-free visualization of acetaminophen-induced liver injury by high-speed stimulated Raman scattering spectral microscopy and multivariate image analysis." Pathology International, vol. 64, No. 10, pp. 518-526 (2014); JP 2015-121660 A; JP H1195119 A; WO 2015/042460 A1; JP 2015-006321 A; JP 2004-254742 A; JP 2013-514520 A; WO 2014/162744 A1; U.S. Pub. No. 2014/0316255; and JP 2006-515927 A.

Office Action regarding corresponding Chinese Patent Application. No. 201680062468.0 dated May 6, 2020 Satoh, Shuya et al., "Label-free visualization of acetaminophen-induced liver injury by high-speed stimulated Raman scattering spectral microscopy and multivariate image analysis." Pathology International, vol. 64, No. 10, pp. 518-526 (2014); JP 2015-121660 A, CN 101959450 A, and CN 102266250 A, and JP H11-95119 A.

English language machine translation provided by Espacenet for JP 2015-121660 A.

English language machine translation provided by Espacenet for JP H1195119 A.

English language machine translation provided by Espacenet for JP 2015-006321 A. Further, U.S. Pub. No. 2014/0354987 is believed to be an English language equivalent of JP 2015-006321 A.

English language machine translation provided by Espacenet for JP 2004-254742 A.

English language machine translation provided by Espacenet for WO 2014/162744 A1. Further, U.S. Pub. No. 2016/0103072 is believed to be an English language equivalent of WO 2014/162744 A1.

English language machine translation provided by Espacenet for CN 102266250 A.

U.S. Pub. No. 2012/0259229 is believed to be an English language equivalent of JP 2013-514520 A.

U.S. Pub. No. 2004/0147033 is believed to be an English language equivalent of JP 2006-515927 A.

U.S. Pub. No. 2010/0331782 A1 is believed to be an English language equivalent of CN 101959450 A.

Chinese Office Action regarding Application No. 201680062468.0, dated Mar. 4, 2022.

* cited by examiner

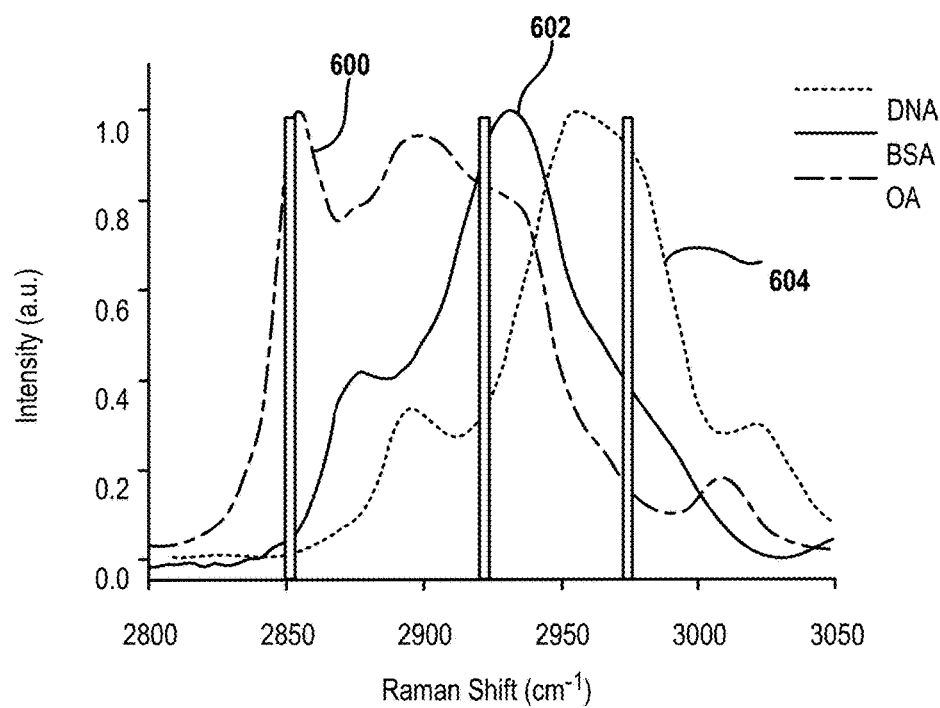
FIG. 6A
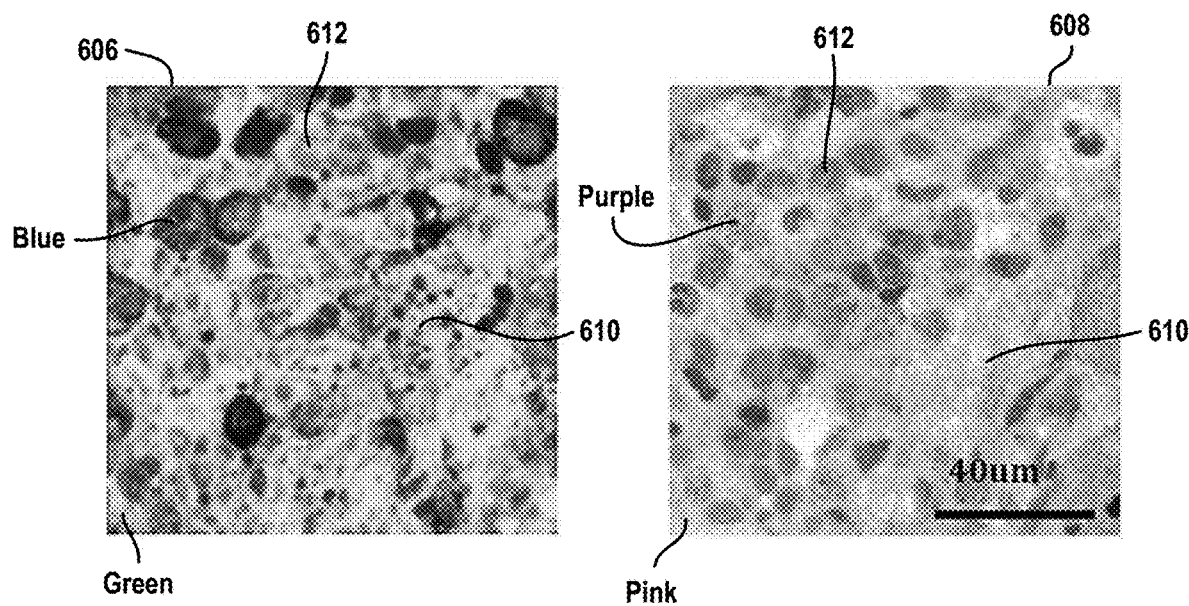
FIG. 6B
FIG. 6C

SRS  H&E
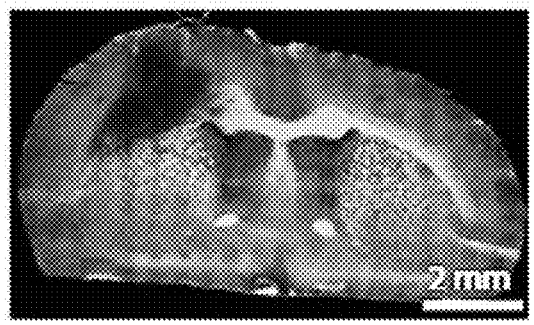 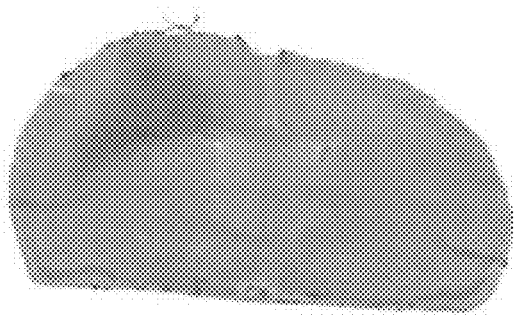
FIG. 7A
SRS  H&E
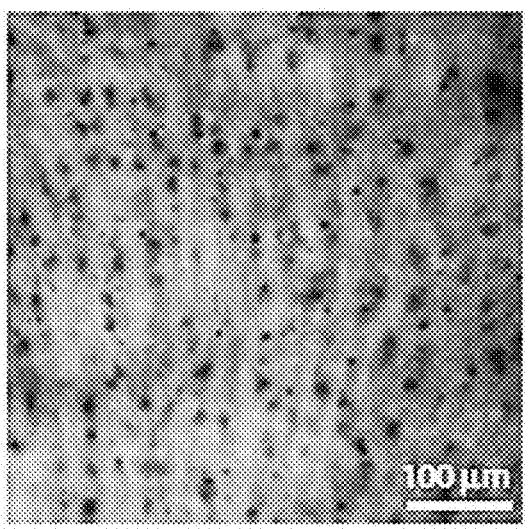 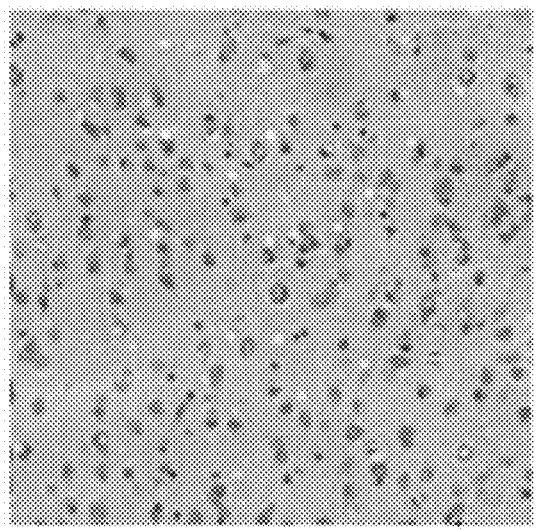
FIG. 7B

SRS            H&E
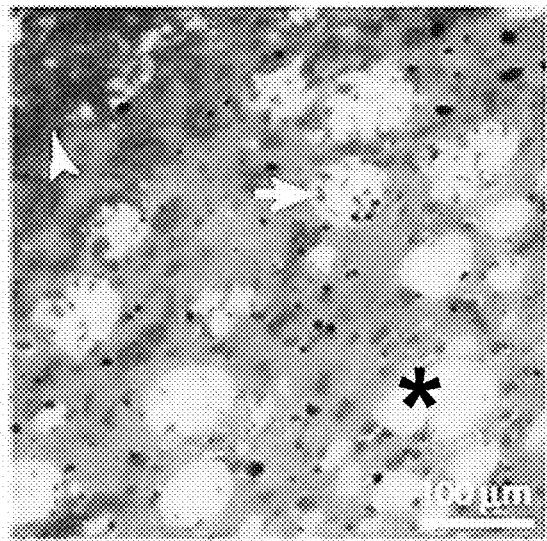 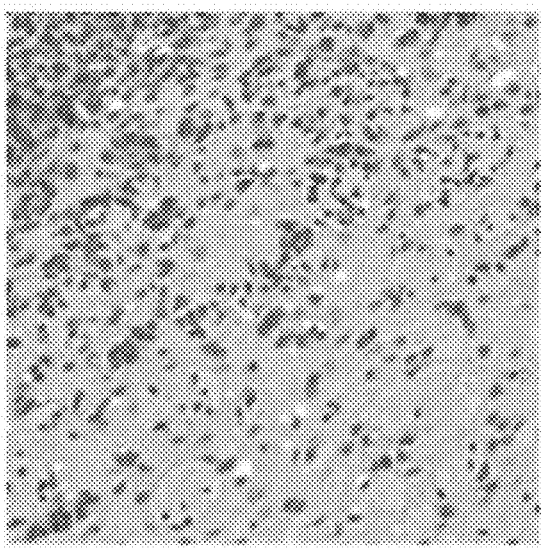
FIG. 7C
SRS            H&E
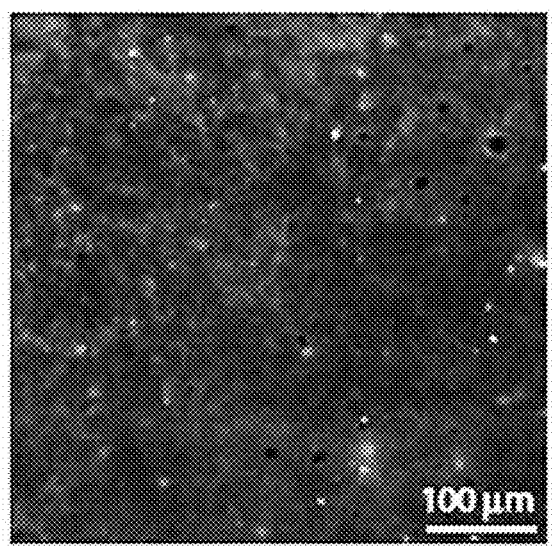 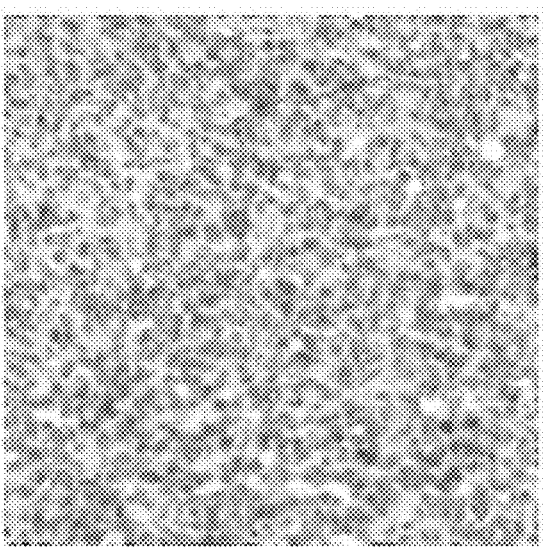
FIG. 7D

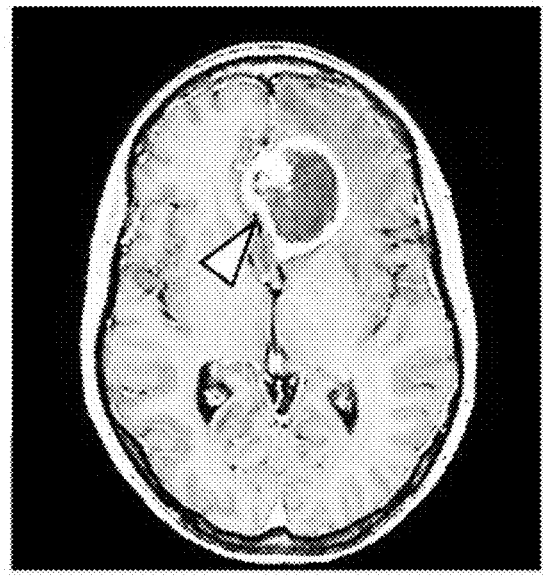
FIG. 8A
SRS  H&E
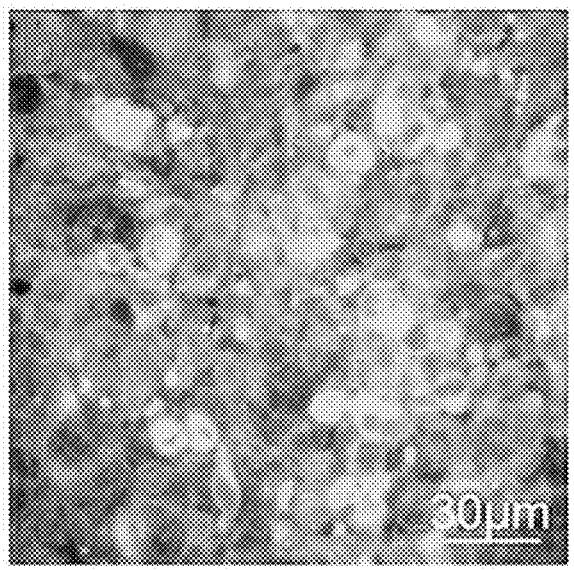 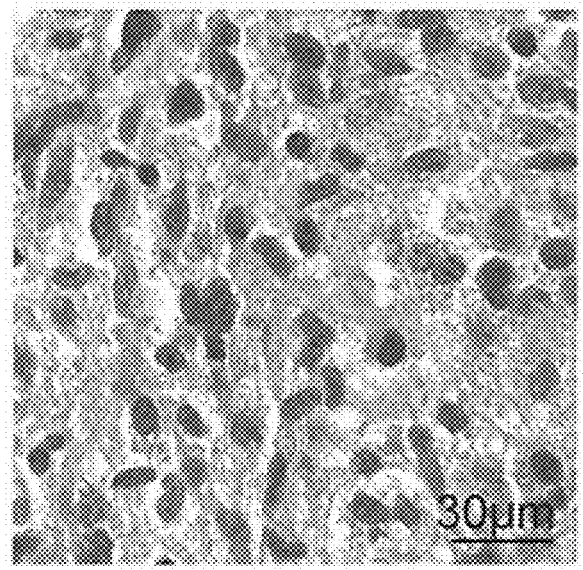
FIG. 8B

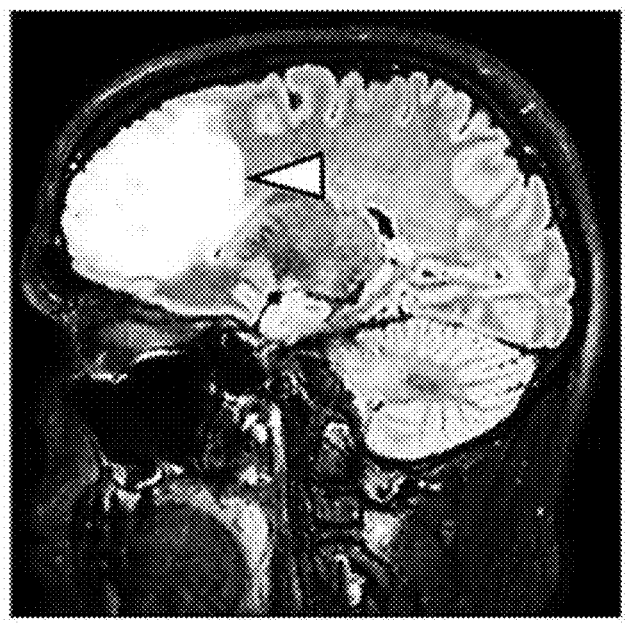
FIG. 8E
SRS  H&E
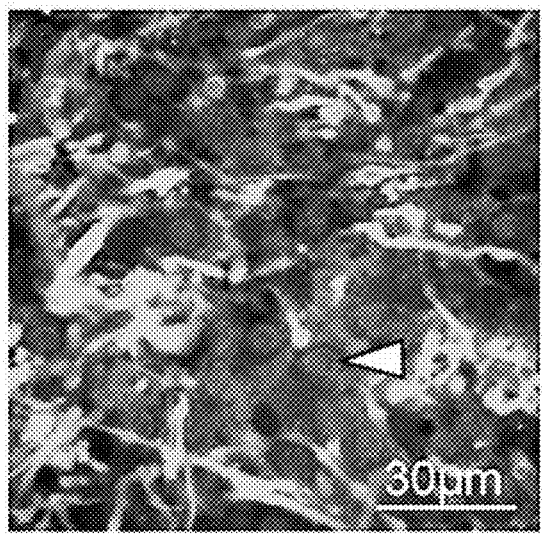 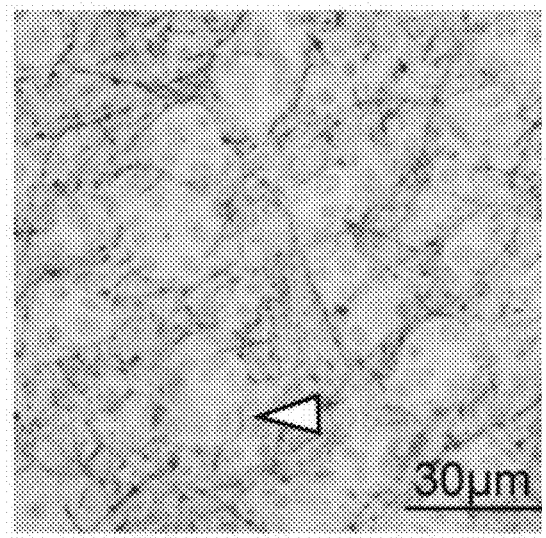
FIG. 8F

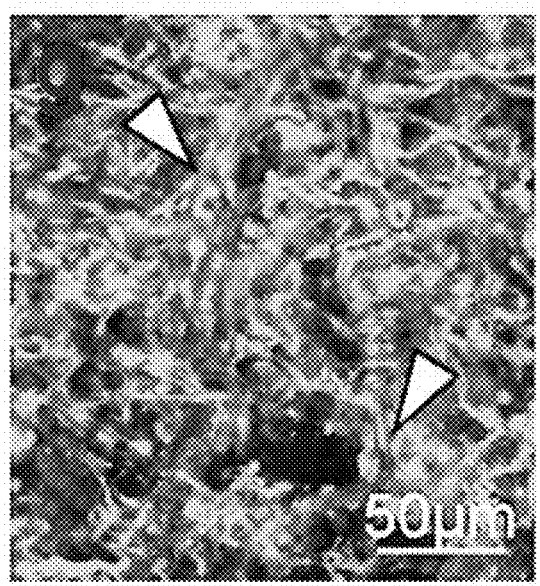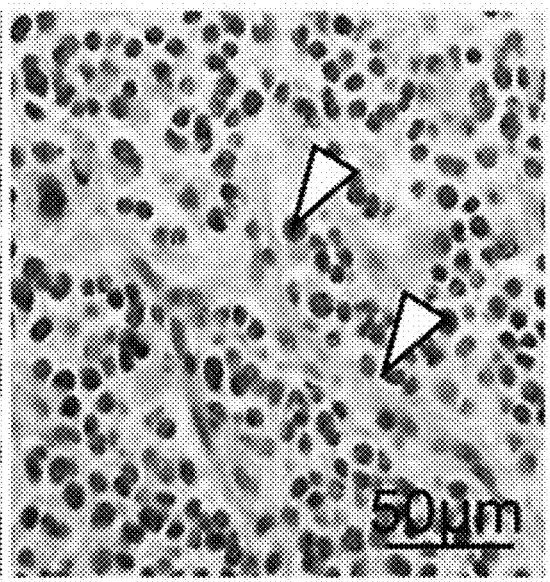
FIG. 8G
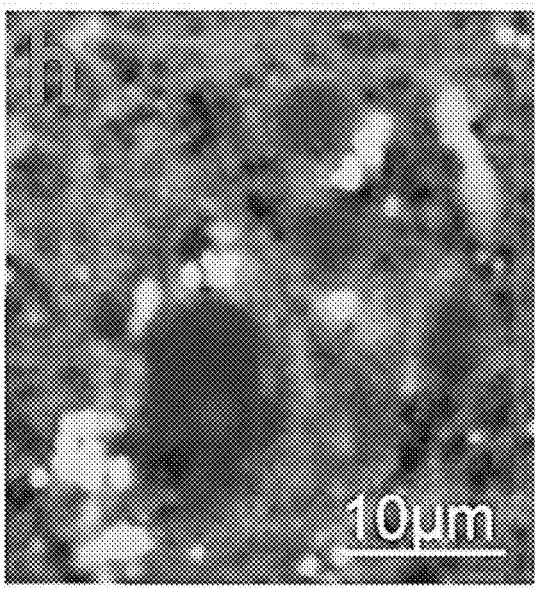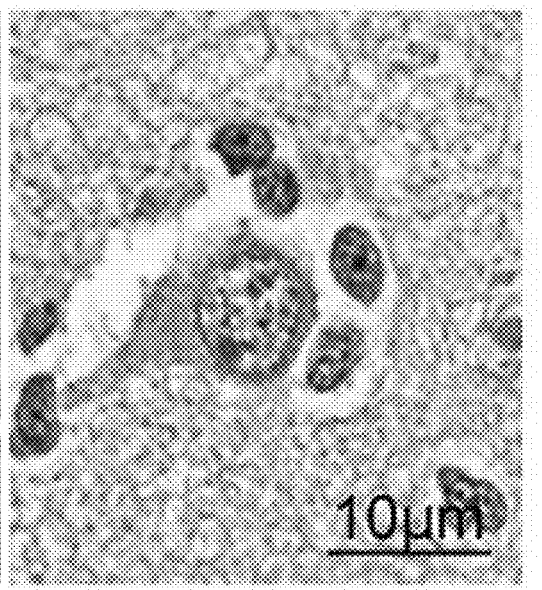
FIG. 8H

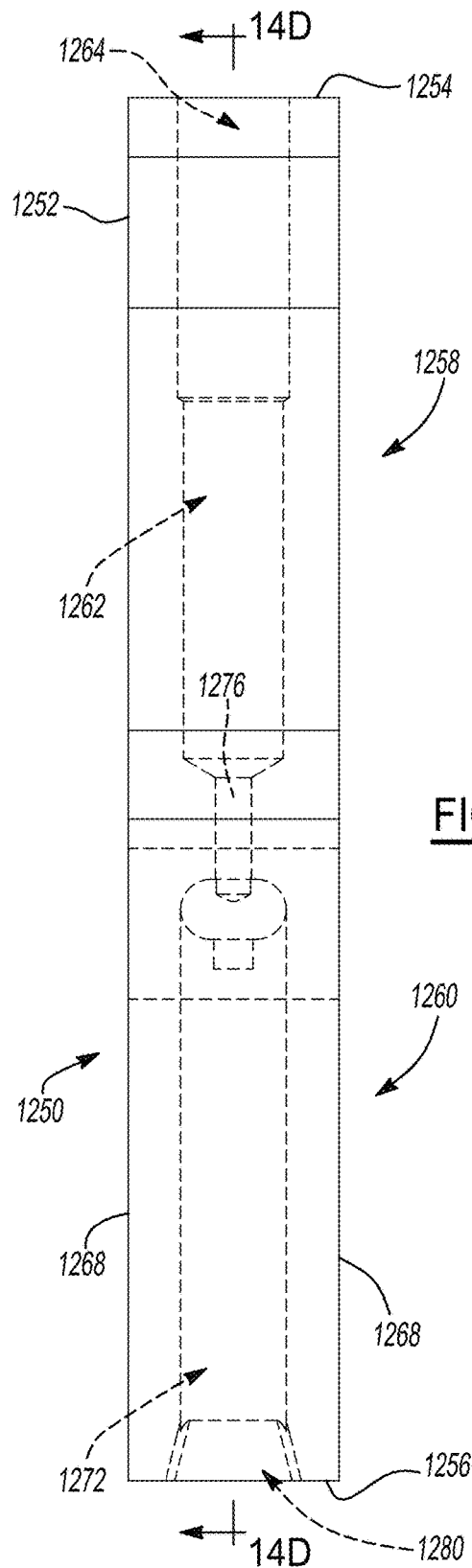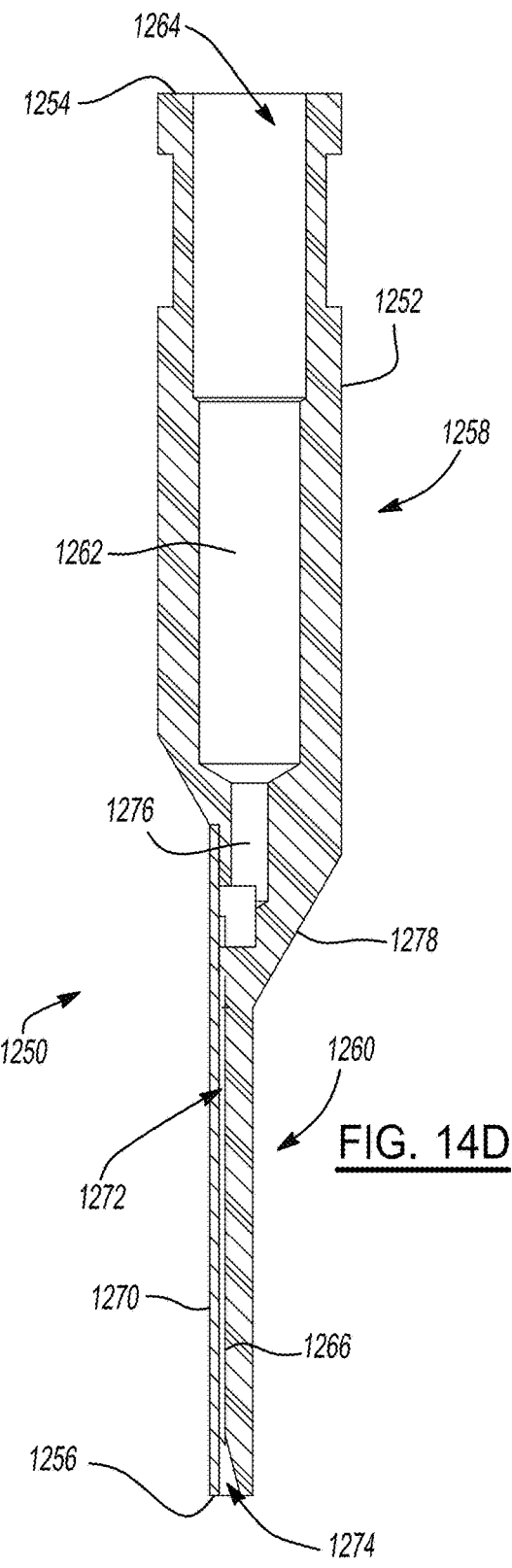

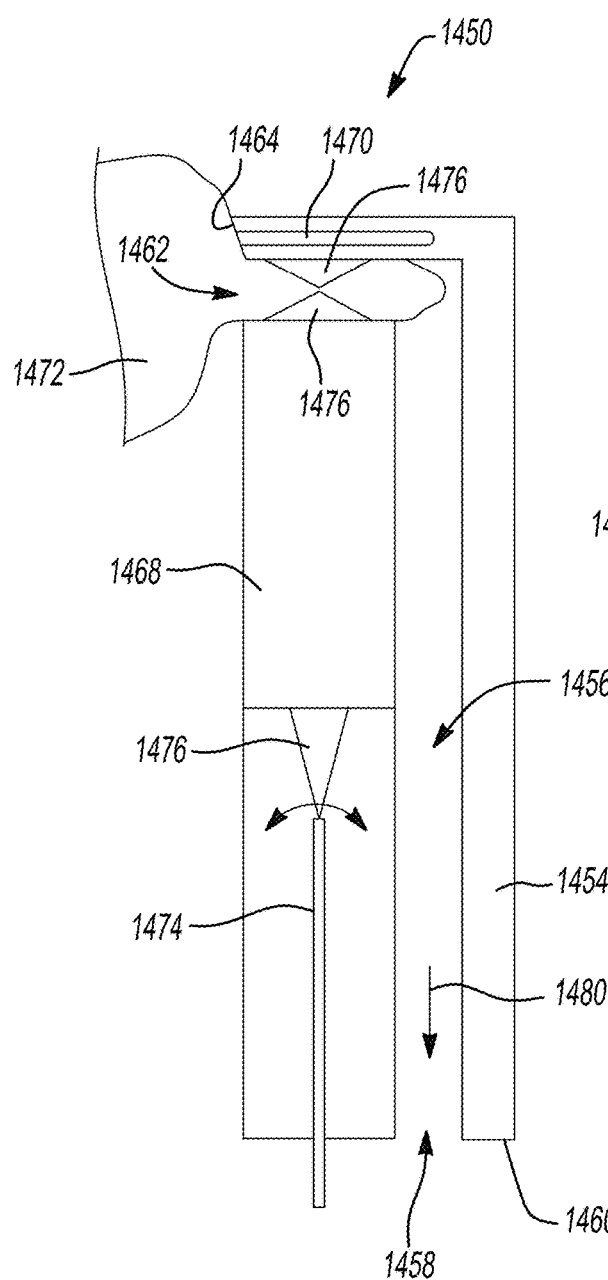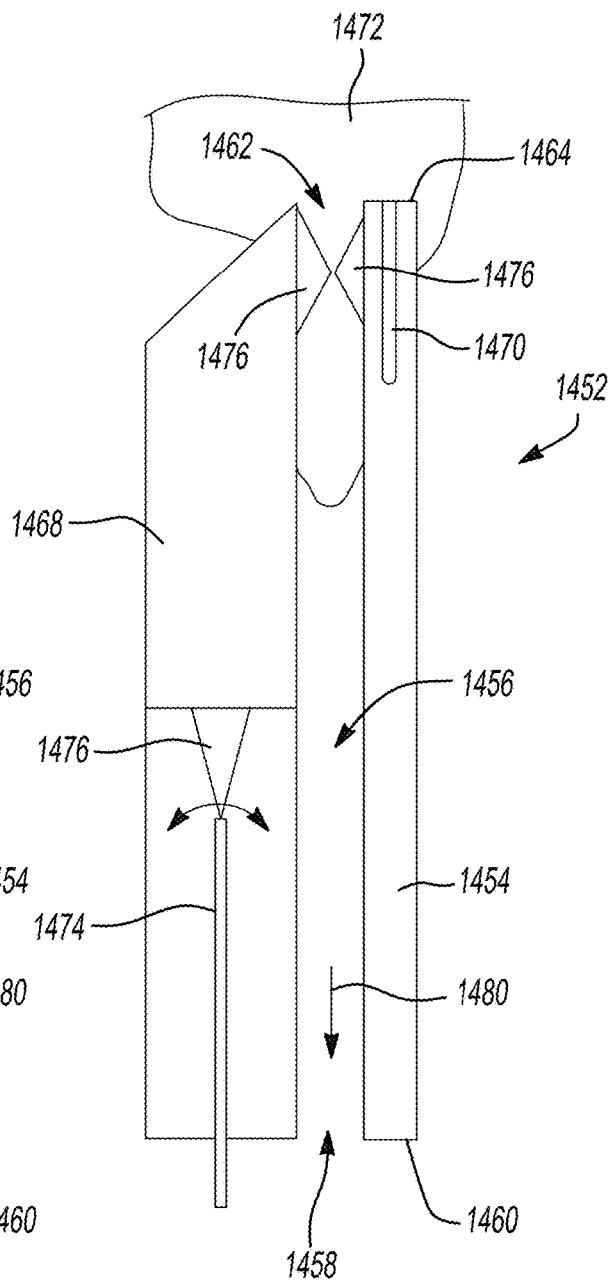

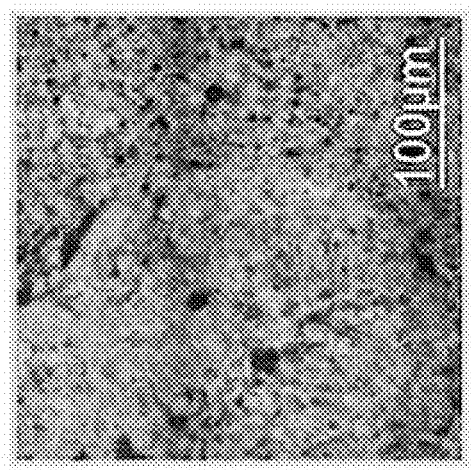
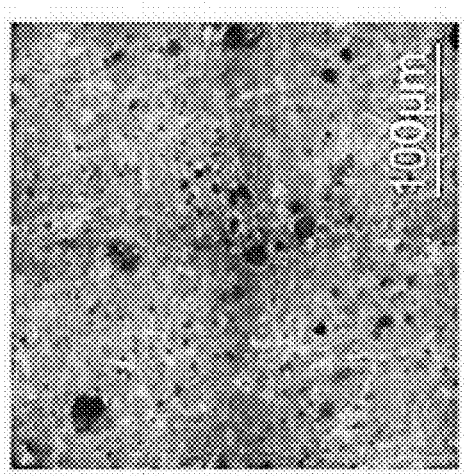
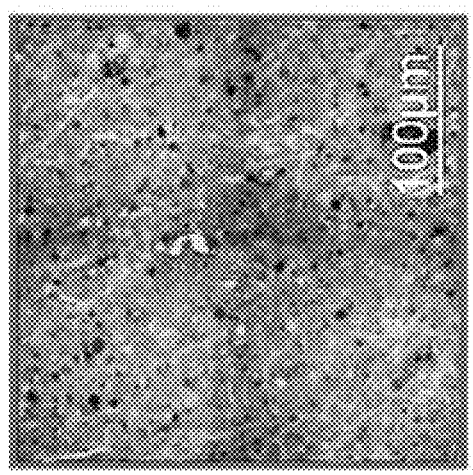
FIG. 29B

BIOPSY DEVICE FOR COHERENT RAMAN IMAGING

CROSS-REFERENCE TO RELATED APPLICATIONS

This application is a continuation of U.S. patent application Ser. No. 15/762,904, filed on Mar. 23, 2018, which is a National Stage of International Application No. PCT/US2016/053481, filed on Sep. 23, 2016, which claims the benefit of U.S. Provisional Application No. 62/232,633, filed on Sep. 25, 2015. The entire disclosures of each of the above applications are incorporated herein by reference.

GOVERNMENT SUPPORT

This invention was made with government support under EB017254 awarded by the National Institutes of Health. The Government has certain rights in the invention.

FIELD

The present disclosure relates to devices and methods for acquiring and analyzing biological tissue samples or biopsies from a subject.

BACKGROUND

This section provides background information related to the present disclosure which is not necessarily prior art.

Surgical resection is the cornerstone of treatment for the majority of tumors. Extent of resection (EOR), or the percentage of tumor removed during surgery, is an important prognostic factor, as most tumor recurrence occurs in or near the resection cavity. In low-grade brain cancer, a recent study showed that patients with at least 90% EOR had an 8-year overall survival rate of 91%, whereas patients with less than 90% EOR had an 8-year overall survival rate of 60%. There is mounting evidence that more extensive surgical resection is associated with longer life expectancy in high-grade glioma, as well. Unfortunately, safely maximizing the extent of resection, that is, removing cancerous regions while sparing healthy brain tissue, remains a challenge, in part due to the difficulty of differentiating tumor from normal brain tissue. Consequently, suboptimal surgical outcomes are common for brain tumor patients. A clinical study showed that among patients with safely resectable tumors, radiographically complete resection was achieved in only 23.5% of patients. In breast cancer, secondary surgeries also occur at a very high rate (10-45% rate depending on the hospital) as a residual tumor being identified post-surgery. In skin cancer the rate is at about 10%. Accordingly, devices and methods for improving EOR are desirable.

SUMMARY

This section provides a general summary of the disclosure, and is not a comprehensive disclosure of its full scope or all of its features.

The present technology provides a biopsy device for analyzing biological samples. The devices include a hollow body extending from a first end to a second end. The body defines a sample collecting portion. A first opening at the first end of the body is operable to receive a source of negative pressure and a second opening at the second end of the body operable to receive a biological sample. The body also includes an optically transparent region disposed in a region corresponding to the sample collecting portion. The optically transparent region is configured to transmit electromagnetic radiation therethrough from an imaging device capable of imaging the biological sample when disposed in the sample collecting portion.

The present technology also provides an imaging system that includes a biopsy device and an imaging device for imagining a biological sample when disposed in the biopsy device. The biopsy device includes a body extending from a first end to a second end. The body defines a sample collecting portion. A first opening at the first end of the body is operable to receive a source of negative pressure and a second opening at the second end of the body operable to receive a biological sample. The body also includes an optically transparent region disposed in a region corresponding to the sample collecting portion. The optically transparent region is configured to transmit electromagnetic radiation therethrough from an imaging device capable of imaging the biological sample when disposed in the sample collecting portion. The imaging device can be a stimulated Raman scattering (SRS) device, a coherent anti-Stokes Raman scattering (CARS) device, a confocal Raman device, a confocal reflection device, a confocal fluorescence device, an optical coherent tomography (OCT) device, a two-photon excited fluorescence (TPEF) device, a second harmonic generation (SHG) device, or a third harmonic generation (THG) device.

Additionally, the present technology provides a method for removing tissue from a subject. The method includes removing a biological sample with a biopsy device from the subject. The biopsy device includes a body extending from a first end to a second. The body defines a sample collecting portion. A first opening at the first end of the body is operable to receive a source of negative pressure and a second opening at the second end of the body operable to receive a biological sample. The body also includes an optically transparent region disposed in a region corresponding to the sample collecting portion. The optically transparent region is configured to transmit electromagnetic radiation therethrough from an imaging device capable of imaging the biological sample when disposed in the sample collecting portion. Therefore, the biological sample is collected in the sample collection portion of the biopsy device. The method also includes imaging the biological sample while retaining the biological sample in the sample collection portion of the biopsy device to obtain an optical image of the biological sample and displaying the optical image on a screen.

The present technology further provides kits that contain at least one disposable biopsy device. The at least one biopsy device includes a body extending from a first end to a second end. The body defines a sample collecting portion. A first opening at the first end of the body is operable to receive a source of negative pressure and a second opening at the second end of the body operable to receive a biological sample. The body also includes an optically transparent region disposed in a region corresponding to the sample collecting portion. The optically transparent region is configured to transmit electromagnetic radiation therethrough from an imaging device capable of imaging the biological sample when disposed in the sample collecting portion. The at least one biopsy device is sterile and packaged.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6A is a graph of Raman spectra;

FIG. 6B is an stimulated Raman scattering (SRS) image displayed in blue and green;

FIG. 6C is an stimulated Raman scattering (SRS) image displayed in pink and purple;

FIG. 7A shows a stimulated Raman scattering (SRS) image and an hematoxylin and eosin (H&E) image of a mouse brain;

FIG. 7B shows SRS and H&E images of normal or minimally hypercellular cortex tissue;

FIG. 7C shows SRS and H&E images of an infiltrating glioma;

FIG. 7D shows SRS and H&E images of a high density glioma;

FIG. 8A shows a magnetic resonance image (MRI) of a glioblastoma;

FIG. 8B shows hypercellularity and nuclear atypia of a viable tumor in both stimulated Raman scattering (SRS) and hematoxylin and eosin (H&E) microscopy;

FIG. 8E shows an MRI of a oligodendroglioma;

FIG. 8F shows SRS and H&E images of hypercellular tissue in an oligodendroglioma;

FIG. 8G shows SRS and H&E images blood vessels;

FIG. 8H shows SRS and H&E images of perneuronal satellitosis;

FIG. 14C is a top view of the biopsy device of FIG. 14A;

FIG. 14D is a cross-sectional view of the biopsy device of FIG. 14C taken along line 14D;

FIG. 21 is an illustration of a first combination device according to certain aspects of the current technology;

FIG. 22 is an illustration of a second combination device according to certain aspects of the current technology;

FIG. 29B shows images of tissue in various transitions.

Corresponding reference numerals indicate corresponding parts throughout the several views of the drawings.

DETAILED DESCRIPTION

Figure 1A:
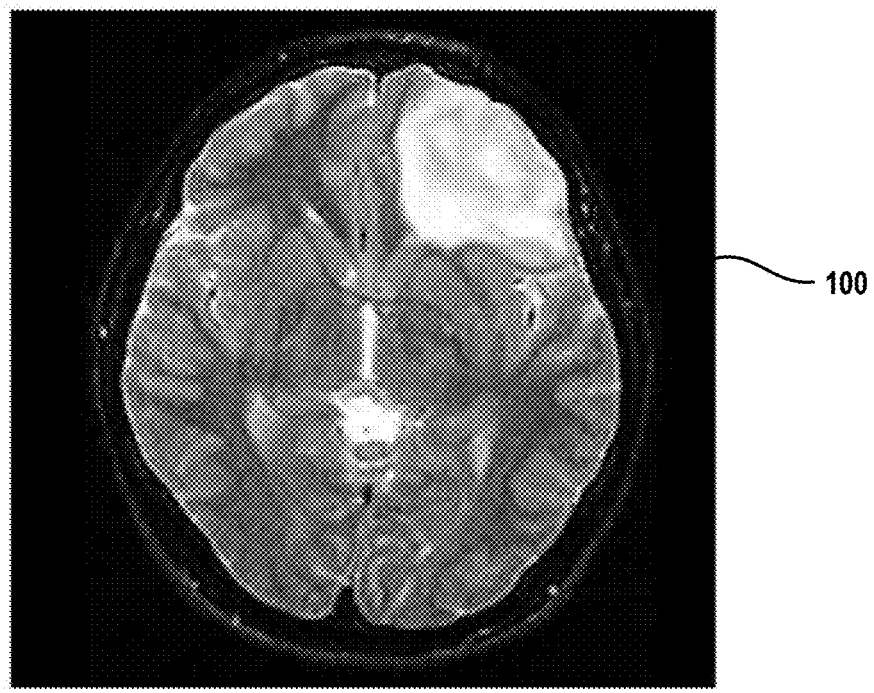
FIG. 1A shows an pre-operative MRI scan of a brain tumor.

Example embodiments will now be described more fully with reference to the accompanying drawings.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

While gross differences between tumor and non-infiltrated tissues are often imperceptible, the cytoarchitectural features of tumor infiltrated brain are distinctive. However, detecting these differences with routine histologic techniques requires that the tissue be thinly sectioned and stained. Frozen section histology is currently the fastest way to obtain histopathologic data that typically takes at least about 30 minutes from biopsy collection biopsy to diagnosis, but the diagnostic accuracy is lower than permanent section histology. Permanent section histology typically takes 2-3 days from biopsy collection to diagnosis, in part due to freezing artifacts. While frozen section histology is used in surgery for diagnosis in cases where pre-operative biopsy was not performed, the long processing times make it often impractical for guiding completeness of resection during the surgical procedure.

Multiple optical imaging modalities have been developed to image tissue without physical sectioning of the tissue. For example confocal microscopy based on intrinsic, extrinsic, fluorescent reflecting, or Raman active species uses a confocal pin hole to suppress out-of-focus signals. Clinically, fluorescent imaging of 5-aminolevulinic acid (5-ALA) is important as it shows some sensitivity and specify for tumors. Using confocal imaging may further increase the sensitivity and specificity, especially at the tumor margin. Multi-photon techniques such a two-photon excited fluorescence (TPEF), second harmonic generation (SHG), third harmonic generation (THG), and coherent Raman scattering (CRS) including coherent anti-Stokes Raman scattering (CARS) and stimulated Raman scattering (SRS), rely on intrinsic optical sectioning due to nonlinear excitation profiles. Optical coherent tomography (OCT) relies on coherent detection to measure a depth-dependent signal and photoacoustic detection relies on a time delay of signals from different depths. Accordingly, imaging can be performed with a modality that is based on intrinsic spectroscopy contrast.

Many of these imaging modalities further rely on species, components, or factors that are intrinsic to a sample for signal generation, rather than on dyes or other contrast agents. These intrinsic species, components, or factors are all rapid and non-destructive techniques that can be used to analyze the molecular composition of a sample on a microscopic level. Like spontaneous Raman scattering, CRS microscopy relies on the intrinsic vibrational properties of molecules, such as lipids, proteins and DNA, to generate contrast in images. The coherent nature of signal generation in SRS microscopy provides amplification of up to 100,000× over spontaneous Raman, enabling imaging speeds of up to a video rate (30 frames/s) and highly sensitive detection under ambient lighting conditions (e.g., in an operating room).

Changing clinical practice by introducing these novel techniques includes improving clinical outcomes, while minimizing an impact on an existing clinical workflow. According, in certain aspects, the biopsy devices, systems, and methods for performing tissue imaging can improve clinical practice while minimizing the impact on clinical workflow.

Similar to intraoperative magnetic resonance imaging (MRI), intraoperative optical imaging may be performed after debulking a tumor core as a surgeon perceives that he or she is approaching the boundaries of the tumor. Optical imaging will help to identify occult residual tumor and resection will be continued as needed and deemed safe. Thus, even though optical imaging has a limited imaging depth, a combination of resection and imaging will have substantially unlimited imaging depth. Also, satellite lesions might be known from pre-operative MRI. Removal of such lesions will also benefit from the combination of resection and imaging.

Hand-held versions of optical imaging systems in accordance with certain aspects of the present disclosure allow imaging in situ, because no tissue needs be removed from a patient for dye staining and section with such versions. Image quality associated with previous hand-held versions may be of diminished quality. Alternatively, if image quality is most important to surgeons and/or pathologists, optical imaging can be performed ex vivo on biopsy samples taken at one or at a plurality of positions of a surgical cavity in real time. Benefits of ex vivo imaging over in situ imaging include improved signal strength due to limited laser power that is safe for use in vivo, and improved collection efficiency due to decreased back-scattered signals and motion artifacts. Reducing the size of an imaging lens for intraoperative use in small surgical cavities might also limit image quality for in situ imaging. If a biopsy device is used toward the end of tumor debulking, no additional tissue necessarily has to be biopsied and ex vivo imaging may be conducted without any disadvantages.

In certain aspects, the present disclosure contemplates devices and methods for obtaining and imaging a biological sample, such as a tissue biopsy. A method may include, for example, obtaining a tissue biopsy sample with a biopsy device and inserting the biopsy device into an imager for ex vivo imaging. In a variation, the biopsy device and imager are combined as a single instrument that may be used in situ. Unlike previous in situ imaging methods and devices, the current methods and devices implement an aspiration of tissue into a sample collection portion of the biopsy device prior to imaging. This aspiration reduces motion artifacts by providing an area that does not move with respect to imaging optics. Moreover, in certain aspects, transmission imaging is enabled by providing a thin sample preparation, which permits the use of larger laser power for imaging, relative to traditional methods and devices, by treating the tissue as an ex vivo specimen. As such, advantages of in situ and ex vivo imaging are combined. In another variation, the biopsy device and imager/imaging device are combined as a single instrument that may be used ex vivo. Here, a tissue biopsy can be obtained with a traditional instrument and then loaded into a sample collection portion of an imager by suction.

In other aspects, the present disclosure contemplates a biopsy device. The biopsy device comprises a hollow body that has a first end and a second end. The hollow body defines a major longitudinal axis meaning the elongate body is substantially straight and symmetrical. However, it is understood that in some embodiments the hollow body may not be symmetrical, such as, for example, when the biopsy device is to be accepted by an imaging device in a specific direction and/or orientation. The hollow body defines a sample collecting portion. A first opening at the first end of the elongate body is operable to receive a source of negative pressure and a second opening at the second end of the elongate body operable to receive a biological sample. The elongate body also includes an optically transparent region disposed in a region corresponding to the sample collecting portion, the optically transparent region being configured to transmit electromagnetic radiation therethrough from an imaging device capable of imaging the biological sample when disposed in the sample collecting portion. In yet other aspects, the present disclosure contemplates an imaging system that includes the biopsy device as set forth above and further includes an imaging device. The imaging system provides an optical signal that is collected form a biological sample in transmission or reflection modes. The imaging device is capable of providing images having compositional and/or structural information about a biological sample contained within the biopsy device. Accordingly, a medical practitioner can distinguish normal tissue from abnormal tissue, i.e., tissue containing malignant cancer cells, and determined whether to remove additional tissue from an area where a biological sample was taken during a surgical procedure. As one or a plurality of biological samples are removed with the biopsy device and analyzed in the imaging device, a medical practitioner can determine the boundaries of a tumor. This determination allows the medical practitioner to remove only tissue that needs to be removed while preserving normal tissue. Optionally, the imaging device may be registered with a surgical navigational system for recording coordinates and/or orientations of the image. A display may then show both navigational and histological information about the biological sample.

Accordingly, in certain aspects, the present technology provides, devices, systems and methods for using an ex vivo optical imager and a consumable biopsy tip that slides onto an end of a surgical suction device (e.g., a neurosurgical suction device), which allows tissue to be pulled into a narrow tissue sample collection region, which corresponds to an imaging portion of the device, by manually controlling negative pressure (e.g., vacuum) supplied from a stationary source of negative pressure or vacuum. Such a stationary source of negative pressure may be a building's vacuum system and can be accessed from a wall in a room of the building. The building may be, for example, a hospital, clinic, or office building. After a biopsy is acquired from a subject, the biopsy device may be loaded directly into an ex vivo optical imager. No sample processing is needed, and histological data appears within a short time frame, by way of example, in certain aspects, less than or equal to about 5 minutes and in other aspects, optionally less than or equal to about 1 minute. A user of the biopsy device, such as a surgeon, can take multiple biopsies from a tissue cavity using a new tip each for each biopsy. The size of the sample collection imaging portion can be kept to a minimum, so as to minimize biopsy volume.

The biopsy devices of the present disclosure may be associated with an imaging system. The imaging system may include one or more imaging devices and associated processing units, including hardware and software. One or more images may be obtained by using the imaging device to create an image of the biological sample collected and retained within the biopsy device. With the current technology, surgeons can detect the presence of a tumor in histologic images. However, some surgeons may choose to consult a pathologist to interpret images. As images are digital, systems can be integrated with a building's telepathology infrastructure. Alternatively, it is possible to use image interpretation algorithms for data analysis.

The present technology also provides systems and methods for bridging the gap between microscopic and macroscopic imaging and keeping track of multiple images, by registering a biopsy or imaging device with a surgical navigational system and recording coordinates and/or orientations of each biopsy or image. For example, as images are acquired, they may be loaded into a navigation system and a split screen can then display both the navigational information and the histological data.

By also keeping track of the orientation of the biopsy with respect to microscope images it is possible to identify tissue areas to be removed or spared. For example, fiber tracks can be seen in an optical image (e.g., based on myelin sheets surrounding axons that appear as either lines or circles in CRS images). By placing the optical image in a specific orientation in the macroscopic image it is possible to highlight fiber tracks that might be spared. In another embodiment, a tumor margin may appear in the optical image. The orientation can then be used to guide a surgeon toward an area where more tumor tissue can be safely removed.

Tissue Imaging Techniques

Figure 1B:
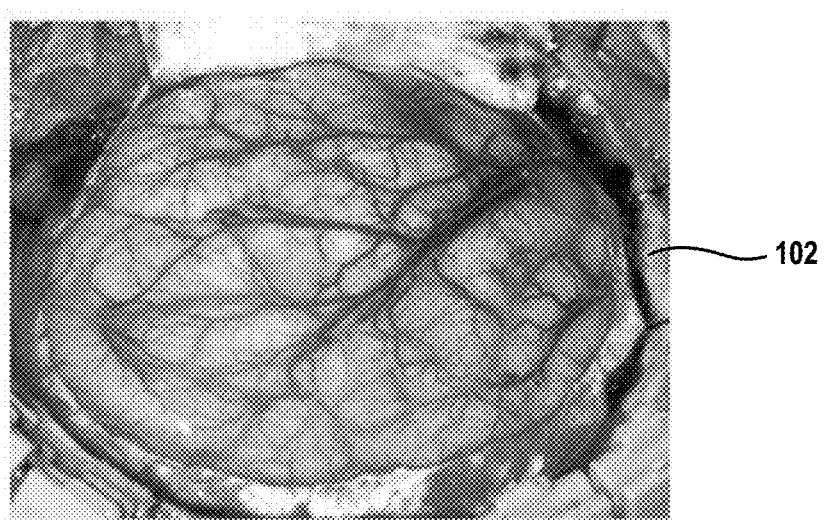
FIG. 1B shows a gross image of a brain with a tumor.

FIG. 1A shows a pre-operative MRI scan 100 of a patient with a brain tumor. FIG. 1B shows a gross image of the exposed brain 102 of the same patient after the patient's scull is opened. As can be seen in FIG. 1B, it is difficult to visually differentiate between normal brain tissue and a brain tumor. The limiting factor in achieving optimal surgical results when removing a tumor is knowing when all of a respectable tumor has been removed because cancerous and non-cancerous brain tissue can appear undistinguishable by a bare eye. It is therefore desirable to use advanced imaging modalities to guide resection.

Raman scattering involves scattering of an excitation photon by a molecule while exciting a molecular vibration. Each type of molecular bond has a specific stiffness (e.g., a C=C bond is stiffer than a C—C bond) and associated mass (e.g., C—C is heavier than C—H) and thus a specific vibrational frequency. A dispersed Raman scattering spectrum is determined by molecular vibrations of a sample and thus derived from the chemical composition of the sample.

Spontaneous Raman spectroscopy can be successfully applied for detecting tumor infiltration in a neurosurgical setting. Spontaneous Raman spectroscopy is often limited to point acquisition due to long integration times, and often lacks the spatial resolution of Coherent Raman Scattering imaging and relies on spectral analysis for diagnosis. By analogy, nuclear magnetic resonance (NMR), the underlying spectroscopy in MRI, is widely used in research applications, but has limited clinical use. In both cases, great diagnostic information is provided for tissue architecture, but doctors prefer images over point spectra for medical decision making.

Figure 2:
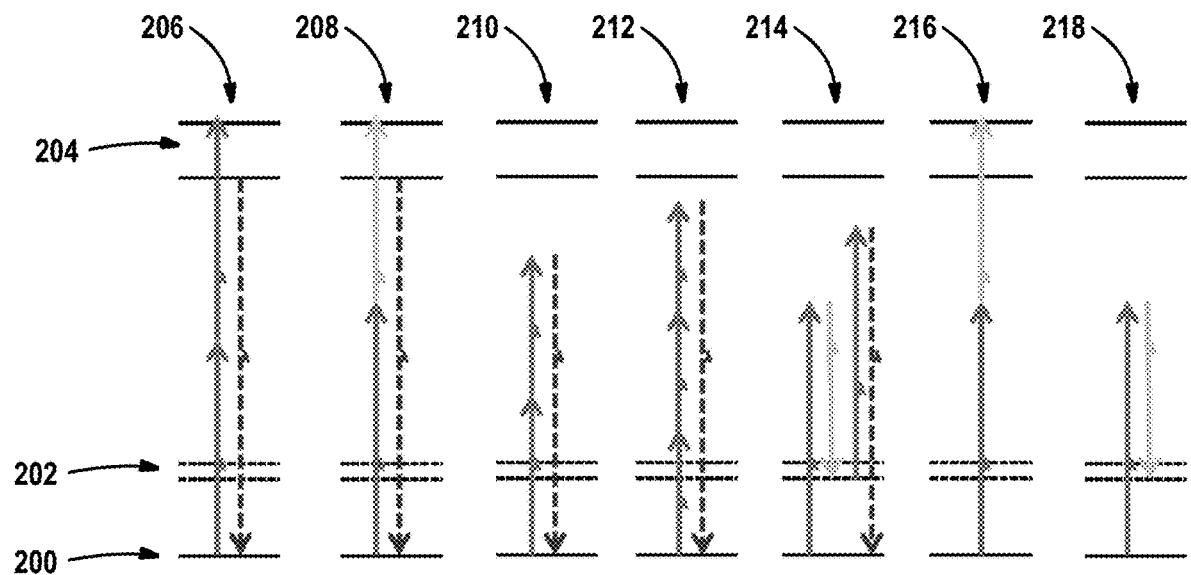
FIG. 2 shows energy diagrams of various multi-photon microscopy (MPM) and spectroscopy methods.

Coherent Raman Scattering (CRS), including coherent anti-Stokes Raman scattering (CARS) and stimulated Raman scattering (SRS), allows amplification of a spontaneous Raman signal. FIG. 2 shows an energy diagram for a CARS 214 and SRS process 218. In both CARS 214 and SRS 218, a sample is excited with a pump and Stokes beams are configured such that a difference frequency matches the frequency of a molecular vibration frequency. In SRS 218 a molecular population is excited from a ground state 200 to a vibrational excited state 202 by passing through a virtual state. As a result, a pump photon is generated and a Stokes photon is absorbed. In CARS 214, a second pump photon is scattered to generate a new photon at the anti-Stokes frequency.

SRS 218 is excited under the same illumination conditions as CARS 214, but differs in detection. CARS 214 is similar to fluorescence in that emission is detected at a wavelength different from the wavelength of excitation beams. SRS 218 is similar to absorption in that the absorption of one excitation beam (e.g., stimulated Raman loss) is measured in the presence of a second beam. While highly sensitive, SRS 218 detection can include extracting a relatively small signal from a laser background with a high-frequency phase-sensitive detection scheme (e.g., lock-in detection). SRS 218 provides a unique capability for chemical specificity as excitation spectra are identical to those of spontaneous Raman. Another advantage of SRS 218 is that it works under ambient light conditions without special optical shielding.

CARS 214 can be detected in transmission or reflection modalities (so-called epi detection) of a sample. SRS 218 is the loss or gain of excitation beams and is thus often detected in transmission. However, if samples are thick, a forward propagating SRS 218 signal is back-scattered and can be detected in a reflection mode. Nonetheless, best signal strength and image quality are typically obtained if samples are thin relative to a mean-free scattering path.

FIG. 2 also shows other multi-photon microscopy (MPM) and spectroscopy methods. In two-photon excited fluorescence (TPEF) 206, two exciting photons are absorbed simultaneously to excite a molecular population from the ground state 200 to an electronically excited state 204, from where it relaxes under a fluorescence emission, which is the signal detected in TPEF microscopy. Two-color two-photon excited fluorescence (TCTPEF) 208 excitation involves simultaneous absorption of two photons with different wavelengths. Either the absorption 216 or the fluorescence emission 208 is measured as the signal in microscopy. TPEF 206 and TCTPEF 208 can either result from an intrinsic tissue species, component or factor, or from extrinsic dyes of fluorophores. TPEF 206 and TCTPEF 208 are typically detected in reflection mode as sample emission is isotropic. Fluorescence signals can also be excited by means of one-photon excitation. Out-of-focus light is then rejected with a confocal pinhole. In second-harmonic generation (SHG) 210 and third-harmonic generation (THG) 212, signal emission is at exactly twice or three times an excitation wavelength. SHG 210 is well known, for example, for imaging collagen. THG 212 measures the nonlinear refractive index and can be used in brain tissue for characterizing tumor infiltration. THG 212 images have some similarity to those of CRS but lack the nuclear specific contrast. Accordingly, in various aspects the current technology includes devices for performing these spectroscopy methods. In various embodiments, the imaging device is selected from a group consisting of: an SRS device, a CARS device, a confocal Raman device, a confocal reflection device, a confocal fluorescence device, an OCT device, a TPEF device, an SHG device, and a THG device.

Figure 3:
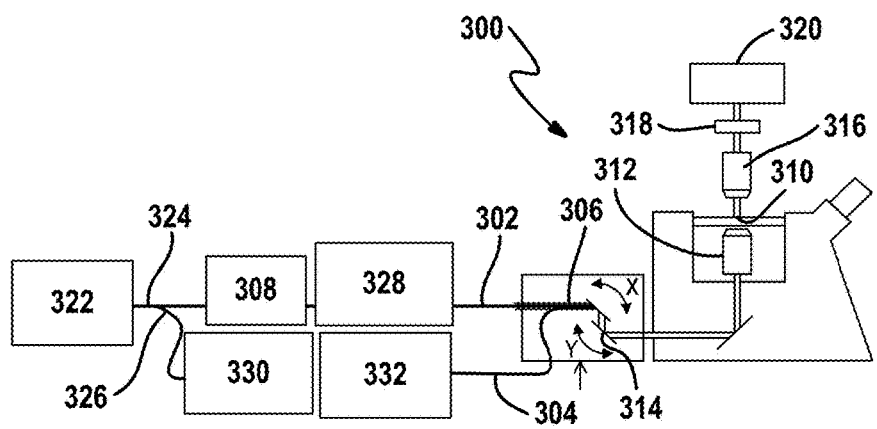
FIG. 3 shows a schematic for an exemplary coherent Raman scattering (CRS) microscopy systems.

FIG. 3 shows a schematic of an exemplary CRS microscope system 300. In the system 300, a pump 302 and a Stokes beam 304 are overlapped with a dichroic mirror 306 to produce collinear beams. Typically, excitation is achieved with pulsed lasers that have a high peak power at a moderate average power to excite a nonlinear CRS signal without causing damage to a sample. Therefore, the system 300 also includes a delay line 308 in at least one of the beam paths for adjusting a relative delay of two trains of pulses such as to temporally overlap the pulses in the sample. The collinear beams are focused into a sample 310 using an objective lens 312. With galvano scan mirrors 314 a common focal volume is scanned through the sample 310 in a deterministic fashion (typically under computer or electronic control). In the case of SRS, a signal is collected with a condenser lens 316 in transmission, optically filtered with an optical filter 318 and detected with a detector 320 to produce a signal as a pixel. A computer or electronics, which generated scan pattern, are used to remap the pixel into an image. Good image quality can be achieved by using a high numerical aperture (NA) objective lenses that typically have a field of view (FOV) of 400 μm. Larger area images can be acquired by coupling a beam-scanned image acquisition with a motorized state. For example mosaic imaging allows stitching multiple XY images into a larger image. For example each individual field of view may be a 400 μm×400 μm area with 1M Pixels (i.e., 1000×1000 pixels) and stitching a 5×5 mosaic would cover a 2 mm×2 mm area with 25M pixels. Alternative strip tiling can be used where the galvano scan mirror 314 only acquires data along a single axis and another axis is from the motorized stage. In this example it is possible to scan a 400 μm×2 mm strip in a single acquisition.

Historically, SRS has been perceived as difficult and costly to implement and operate in a clinical setting, primarily because of the need for two tightly synchronized, tunable, ultrashort (picosecond) laser pulse trains. Here, in certain variations, the present technology may employ a custom dual-wavelength fiber laser source that is robust, due to light guiding by the fiber core, and relatively inexpensive, due to economy of scale of the telecommunications industry, can be implemented. A prototype system with a custom dual-wavelength fiber laser source can be installed in, for example, an operating room and operated by users without extensive training in microscopy.

Different laser sources may be used to provide excitation beams for CRS. Many academic labs use solid-state optical parametric oscillator (OPO)-based systems to generate a synchronized two pulse train 302 and 304. Other approaches included electronic synchronization of two independent lasers by either feedback on a cavity length or pulse-on-demand solutions. In the fiber-laser based implementation of a CRS microscope, optical synchronization as in the OPO system can be employed, which is very robust. The laser source is based on the fact that a frequency difference of two major fiber gain media, Erbium (Er) and Ytterbium (Yb), overlaps with a high wavenumber region of Raman spectra. Specifically, an Erbium (Er)-doped oscillator 322 produces a train of pulses 324 that is then split by an optical splitter 326. One arm is amplified in an Er-doped fiber amplifier 328 to produce the first train of pulses 302. It is possible to further include a second harmonic generation unit after the fiber amplifier 328 to double the frequency of the output of the amplifier 328 to provide the first train of pulses 302. The second arm is frequency shifted in a frequency shifting unit 330, for example, by using a super-continuum and a narrowband filter that can be tunable. A frequency shifted output is then amplified in an Ytterbium (Yb)-doped amplifier 332 to provide the second train of pulses 304.

In various embodiments, the system 300 is configured to achieve: (1) an average power of from about 50 to about 500 mW for a pump beam at from about 600 nm to about 1000 nm with a 0.5-10 ps pulse duration a repetition rate of from about 10 MHz to about 100 MHz; (2) an average power of from about 50 mW to about 1000 mW for a tunable Stokes beam from about 900 nm to about 1100 nm; and (3) a timing jitter of less than or equal to about 100 fs. The system 300 can generate images in less than or equal to about 5 seconds, in less than or equal to about 2 seconds, or in less than or equal to about 1 seconds. Wavelength tuning for multi-color acquisition is typically performed in between frames. Large-area mosaic images can then be acquired in less than or equal to about 5 minutes, less than or equal to about 4 minutes, less than or equal to about 3 minutes, less than or equal to about 2 minutes, or less than or equal to about 1 minutes. In one embodiment, the system 300 is configured to achieve: (1) an average power of 300 mW for a fixed-wavelength pump beam at 790 nm with a 2 ps pulse duration and 80 MHz repetition rate; (2) an average power of about 500 mW for the tunable Stokes beam from 1010 nm to 1045 nm; and (3) a timing jitter of less than or equal to about 50 fs. This system 300 corresponds to Raman coverage from 2800 $cm^{-1}$ to 3100 $cm^{-1}$. With such a system 300, it is possible to generate two-color 25 MPixel SRS images of 2 mm×2 mm regions from fresh surgical specimens with a 0.6 nm resolution in under 1 minute.

Figure 4:
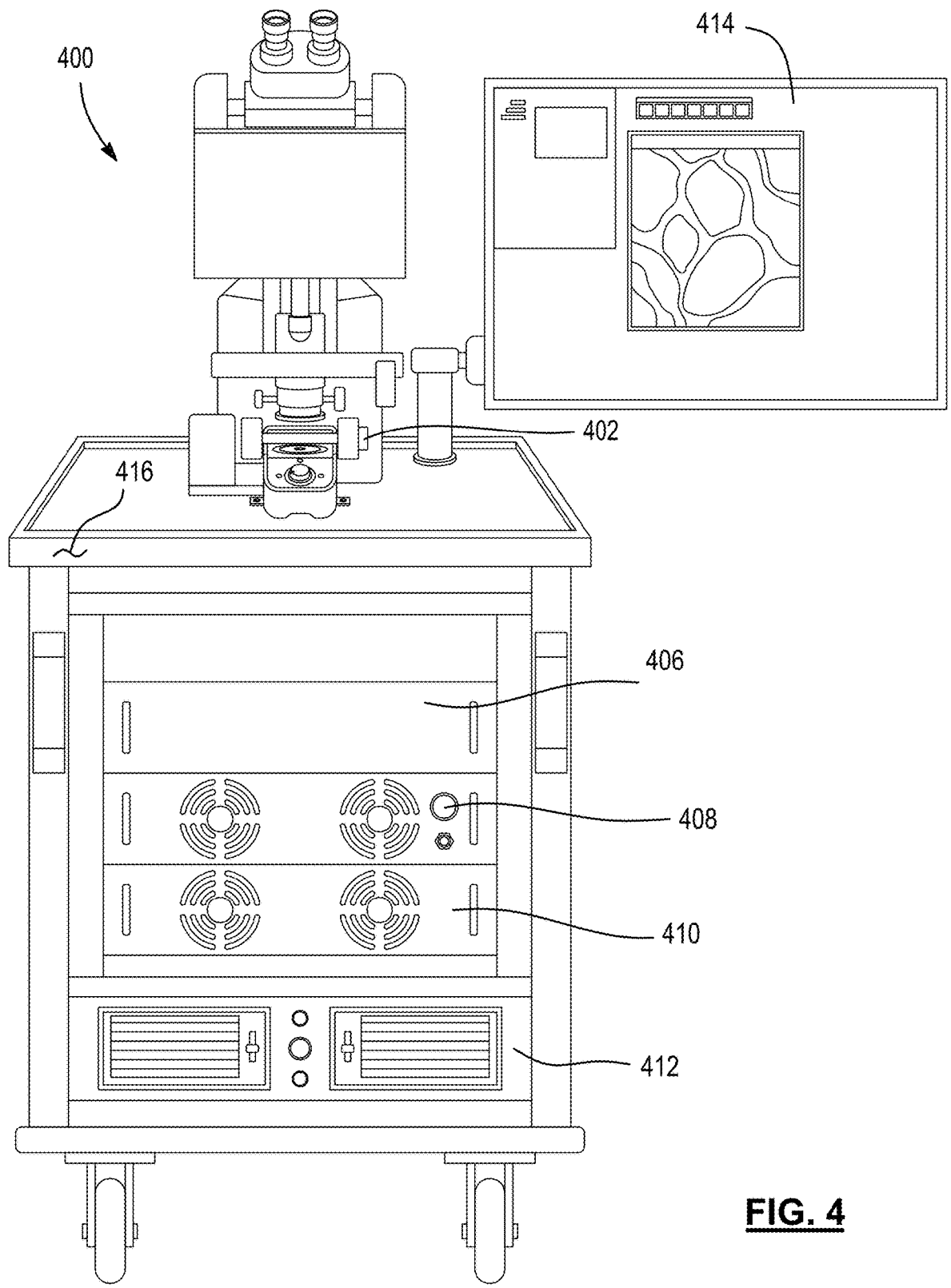
FIG. 4 shows an exemplary fiber-laser based coherent Raman scattering (CRS) microscope.

An example of a fiber-laser based multi-modal SRS microscope 400 is shown in FIG. 4. The microscope 400 is built on an on an Olympus microscope body 402 and a beam-scanning unit 404 that seamlessly integrates a laser source 406 through fiber delivery technology. A laser and the microscope 400 are controlled through control electronics 408 (laser) and 410 (microscope) from a computer 412. Imaging data are displayed on a screen 414. In one embodiment, imaging software is based on an open-source microscopy platform μ-Manager. It allows full control of the imaging, laser and stage parameters and provides an algorithm for multi-color mosaic imaging. All components (400-414) can be mounted in to a mobile cart 416 to provide a fully integrated multi-modal SRS microscope.

Figure 5:
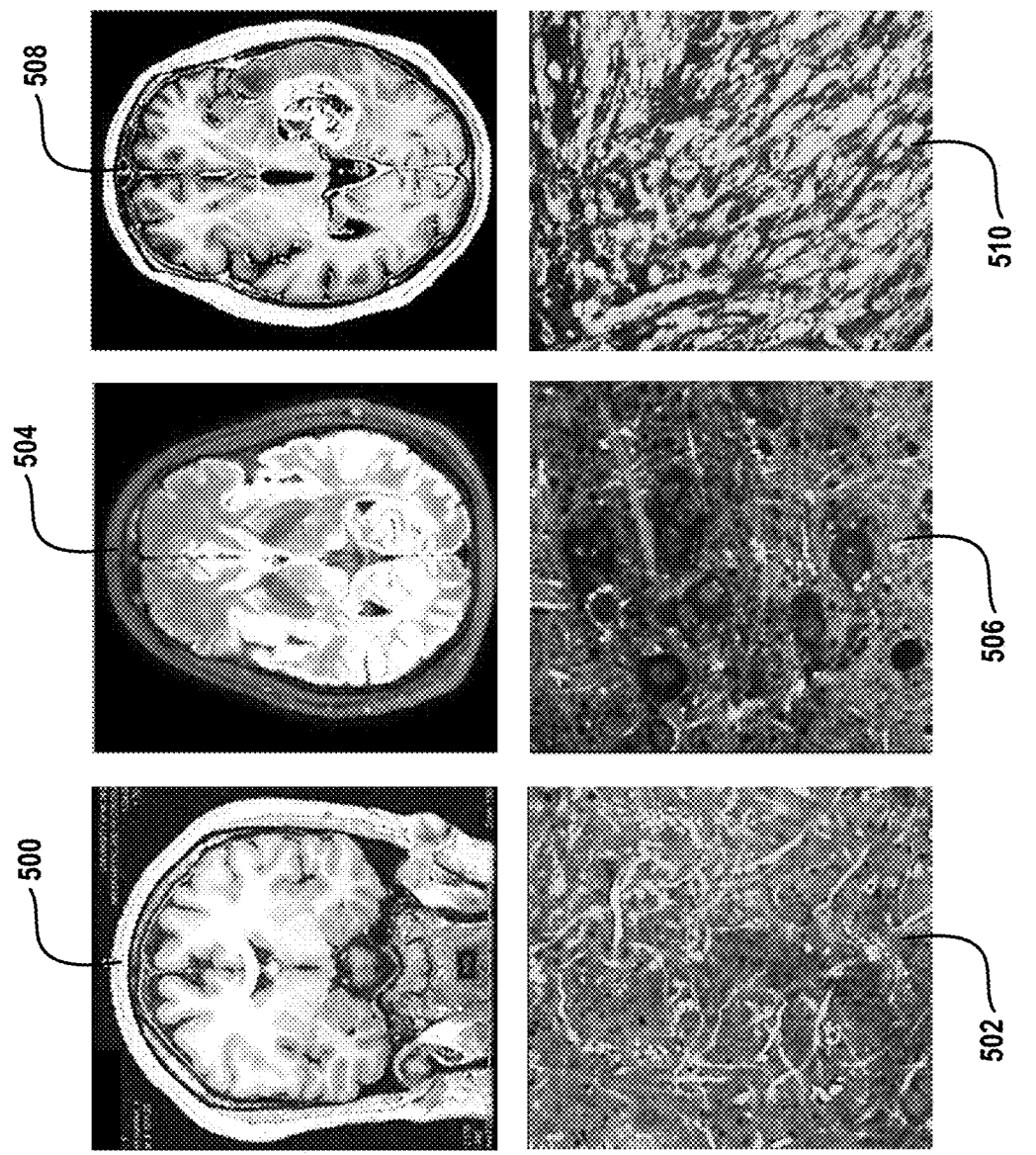
FIG. 5 shows stimulated Raman scattering (SRS) images of brain tissue from a fiber-laser based SRS system.

FIG. 5 shows SRS images from a fiber-laser based SRS prototype system from a patient with epilepsy undergoing temporal lobectomy 500, a patient with low-grade oligodendroglioma 504, and a patient with high-grade gliomas 508. Corresponding SRS images show a normal human cortex 502 characterized by sparse cellularity and many axons, a human brain with low-grade oligodendroglioma 506 with characteristic tumor cells with round nuclei and abundant cytoplasm, and a human brain with high-grade gliomas 510 with densely packed cells in a pseudopallisading pattern. Importantly, there are differences in the microscopic appearance of normal and tumor-infiltrated brains.

Figure 6D:
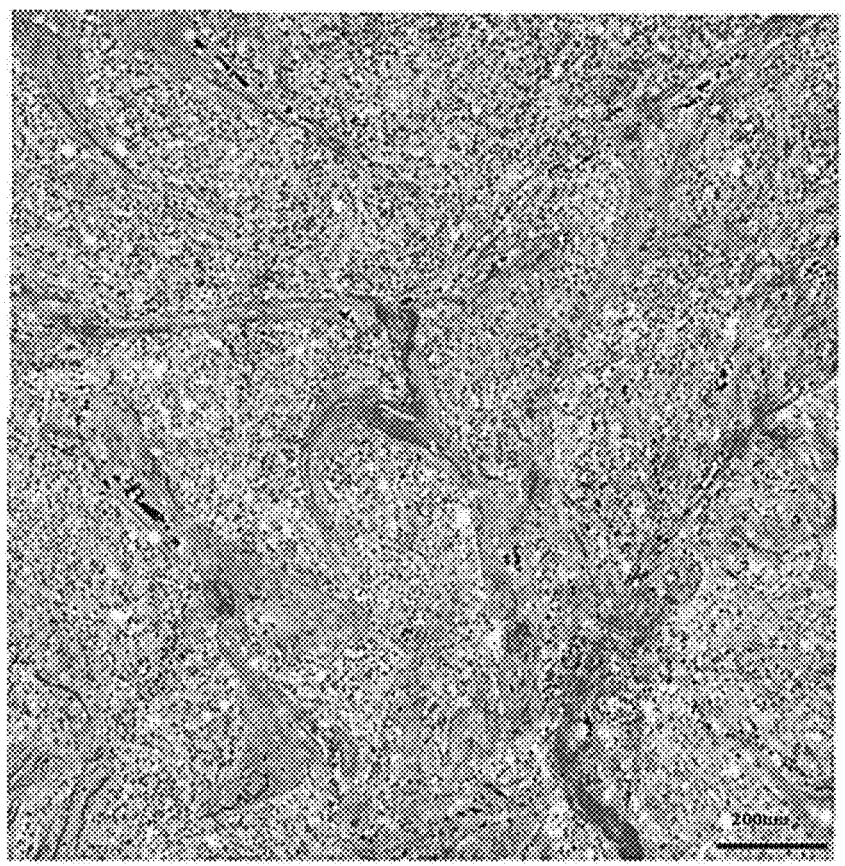
FIG. 6D is a large-area stitched SRS image.

SRS microscopy generates images that highlight similar morphological features as hematoxylin and eosin (H&E), the most commonly used stains in neuropathology. FIG. 6A shows Raman spectra of common molecules, such as lipids 600, proteins 602 and DNA 604, in tissue. By imaging tissue at multiple Raman shifts (such as, for example, at 2850 cm$^{-1}$ and 2930 cm$^{-1}$ or 2850 cm$^{-1}$, 2930 cm$^{-1}$ and 2960 cm$^{-1}$) and using spectral unmixing techniques, multicolor SRS images can be generated that can be displayed in different pseudo colors, such as, for example, blue and green in 606 of FIG. 6B or a pink and purple as in 608 of FIG. 6C to mimic H&E staining. SRS images of the CH$_2$-vibration (2845 cm$^{-1}$) show lipid-rich structures, such as myelinated axons and extracellular matrix 610. SRS images of the CH$_3$-vibration (2930 cm$^{-1}$) show protein- and DNA-rich structures such as nuclei and collagen fibers 612. FIG. 6D shows stitched image of a 1.5 mm×1.5 mm region of a low-grade glioma.

SRS microscopy is validated for tumor margin delineation in brain cancer. FIGS. 7A-7D show comparisons of SRS images and H&E histology images in a human glioma xenograft mouse model. Thin frozen sections are first imaged with SRS and then stained with H&E, allowing comparison of the methods on identical tissue. FIG. 7A shows a full section of a mouse brain. FIG. 7B shows a high-magnification view of normal or minimally hypercellular cortex tissue (with less than 25% tumor infiltration). FIG. 7C shows an infiltrating glioma (with 25%-75% tumor infiltration) with normal white matter bundles (asterisk), tumor-infiltrated bundles (arrow), and dense tumor cells (arrowhead). FIG. 7D shows high-density glioma (with greater than 75% tumor infiltration). These images are used to populate a web-based survey to quantitatively compare SRS and H&E microscopy. The inter-method agreement is excellent (k=0.98) between SRS and standard H&E staining for characterizing the degree of tumor infiltration.

Figure 8C:
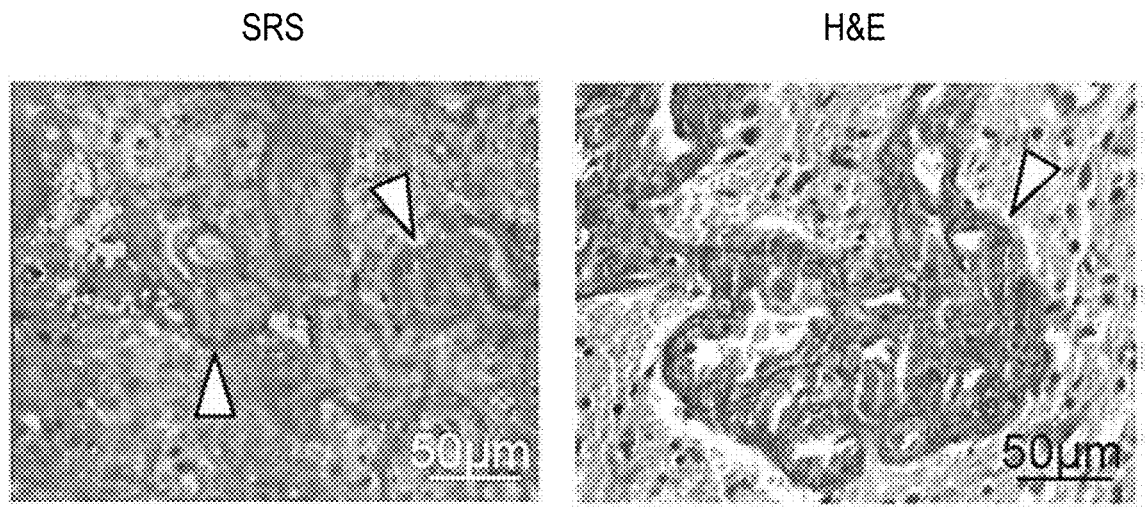
FIG. 8C shows SRS and H&E images of vascular complexes.
Figure 8D:
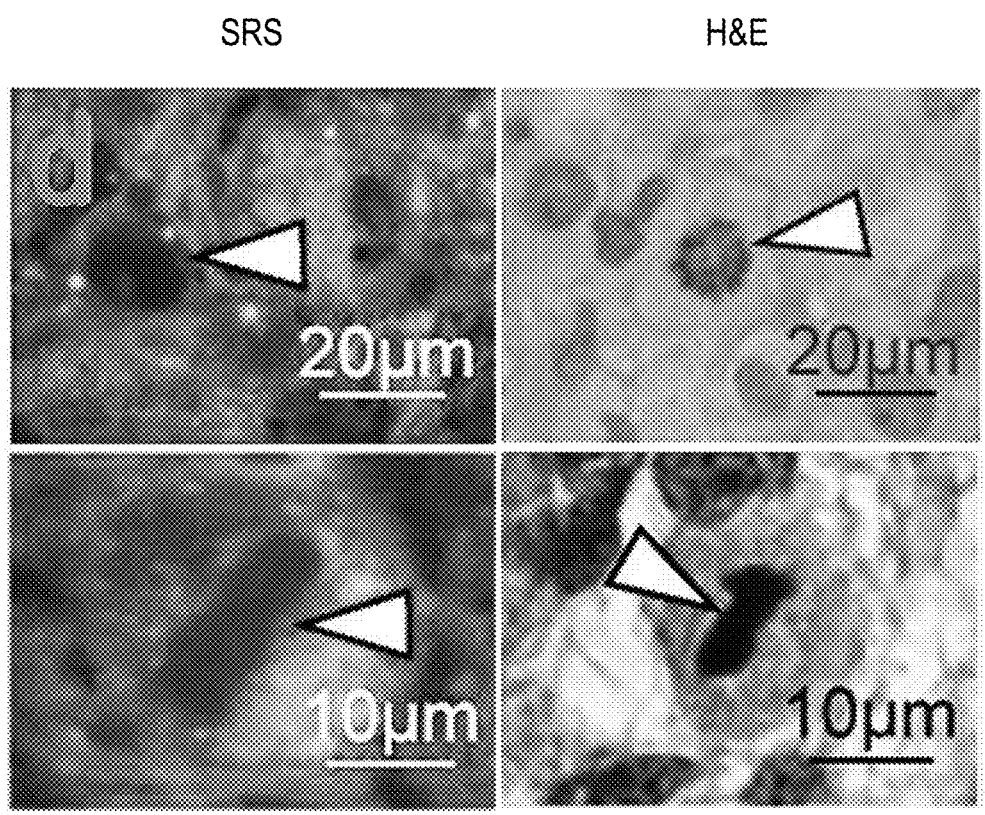
FIG. 8D shows SRS and H&E images of mitotic figures.

SRS is also validated in fresh unprocessed surgical specimens 60 from 22 neurosurgical patients. SRS detected tumor infiltration in near-perfect agreement with standard H&E light microscopy. The unique chemical contrast specific to SRS microscopy enables tumor detection by revealing quantifiable alterations in tissue cellularity, axonal density and protein:lipid ratio in tumor-infiltrated tissues FIGS. 8A-8H show comparisons of SRS images and H&E histology images in a human surgical specimen. FIG. 8A shows an MRI image of a glioblastoma (GBM; arrowhead) demonstrating ring enhancement that is imaged by SRS and H&E. FIG. 8B shows that hypercellularity and nuclear atypia of viable tumor is apparent on both SRS (left) and H&E (right) microscopy. In FIG. 8C, microvascular proliferation creates tortuous vascular complexes evident on SRS microscopy (left, arrowheads) and highlighted with periodic acid Schiff staining (right, arrowhead). As shown in FIG. 8D, mitotic figures are also visible (arrowheads) with SRS microscopy (left) and H&E staining (right). An MRI image of a non-enhancing, low-grade oligodendroglioma is shown in FIG. 8E. As shown in FIG. 8F, the oligodendroglioma consists of hypercellular tissue with nests of "fried-egg" morphology (arrowheads) causing minimal axonal disruption on SRS imaging (left), as confirmed through neurofilament immunostaining (right). In FIG. 8G, "chicken wire" blood vessels (arrowheads) are imaged with SRS (left) and H&E (right) microscopy. In FIG. 8H, perineuronal satellitosis is visible in both SRS (left) and H&E (right) microscopy.

Biopsy Devices and Imaging

It is desirable to use SRS, or other optical imaging or spectroscopy techniques, in conjugation with a biopsy device that allows for taking a tissue biopsy, as small as possible, but diagnostically relevant volume (to minimize risk for neurological deficits), from the surface of the exposed surgical cavity to access without time delay a degree of tumor infiltration and whether to continue resection. For the acquisition of the images in FIG. 5, this was accomplished using standard neuro-surgical biopsy forceps (e.g., B. Braun, Bethlehem, Pa.) using a cutting mechanism. Small pieces of tissue were mounted between a microscope slide and a No 1.5 coverslip using a 240 μm spacer (Grace Biolabs Inc., Bend, Oreg.) and held in compression. Although in this variation, image quality is excellent, sample processing was somewhat cumbersome thus making it somewhat less desirable to integrate into a neurosurgery workflow.

Adapting standard neuro-surgical instruments, such as forceps, to include optical windows for imaging would be very hard and expensive because of the many moving parts, the concern to achieve a thin and flat sample, and the need to minimize the amount of tissue to be biopsied.

Instruments have been developed for core needle biopsy (CNB) and for fine needle aspiration biopsy (FNA). These needle-based devices are designed to piece and cut into the patient toward the desired tissue or sample to obtain a biopsy specimen. The motivation for optical imaging or spectroscopy is to reduce rates of false biopsies or to increase yields of diagnostic tumor for molecular techniques. Needles are typically made from metal and have a sharp edge for cutting a sample or penetrating skin or other tissue. Needles are not normally used in open surgical procedures because of risks associated with sharp edges.

An approach for taking biopsies from a tissue surface with minimal risk to the patient is known as touch or squash-prep. While this approach allows for cytological examination, tissue architecture is often not preserved, which can significantly limit the diagnostic accuracy of the technique.

Instruments used in neurosurgery typically rely on negative pressure, i.e., suction, and are often combined with ultra-sound for breaking-up dense tissue (e.g., Cavitron Ultrasonic Surgical Aspirator; CUSA). Here, the goal is to remove tissue effectively. In certain aspects, it is desirable to employ a biopsy device that relies on suction rather than cutting or compression to extract a biopsy specimen. Such a system better preserves the cytoarchitecture and integrity of the biological sample removed from a subject for rapid histological analysis, while enabling integration of the biopsy device into an existing surgical workflow. Also, it is desirable to keep a collection channel thin enough for optical imaging and to keep a sampling volume small enough to avoid neurological deficit that might cause significant distortions and loss of diagnostically relevant tissue architecture.

To address the need for improved instrumentation and methods for taking and imaging biopsy specimens during open surgical procedures, the present technology provides biopsy tips, devices and methods for decreasing tissue distortion and simultaneously providing quality real time images that provide compositional and/or structural information about a tissue.

Accordingly, rectangular glass capillaries with various channel heights and widths (commercially available from VitroCom) were connected to suction devices to generate biopsy devices. The biopsy devices are powered by any stationary or mobile source of negative pressure, i.e., suction, used in the art, such as suction provided by a building's vacuum system that circulates in and through the building's walls, a vacuum pump, or a freestanding system that generates suction autonomously (such as a NEPTUNE® 2 waste management system commercially available from Stryker® Surgical as a non-limiting example). Such devices are used to suck up brain tissue. Efficient suction of tissue is achieved when the channel has a height of greater than or equal to about 200 µm; however, building-supplied suction is powerful enough to suck up or aspirate tissue into a 100 µm channel without ultra-sound aspiration.

Figure 13A:
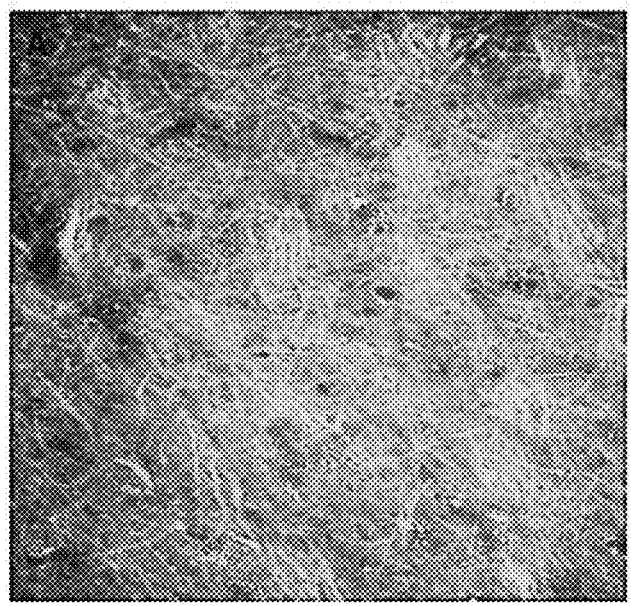
FIG. 13A shows a two-color stimulated Raman scattering (SRS) image acquired in a rectangular glass capillary with 200-μm channel height, 4-mm channel width, and 200-μm wall thickness.

Tissue samples are acquired in the biopsy device, which was then analyzed in the fiber-laser based SRS microscope 400 shown in FIG. 4 and imaged with transmission SRS. Sufficient image quality is achieved when the height of the channel is equal to or less than about 500 µm, equal to or less than about 400 µm, equal to or less than about 300 µm equal to or less than about 200 µm equal to or less than about 100 µm. FIG. 13A shows a two-color SRS image acquired in a rectangular glass capillary with 200-um channel height, 4-mm channel width, and 200-um wall thickness. Surprisingly there was no apparent loss in image quality or any signs of tissue distortion or interference from blood compared to more cumbersome sample preparations using a coverslip, cover slide and double-sided stick tape used to acquire the images of FIG. 5. Also, additional liquid was not required for refraction index matching. The images do not indicate sample drift, stage hysteresis, wobble or nonlinear motion resulting in non-overlapping color channels.

Figure 9:
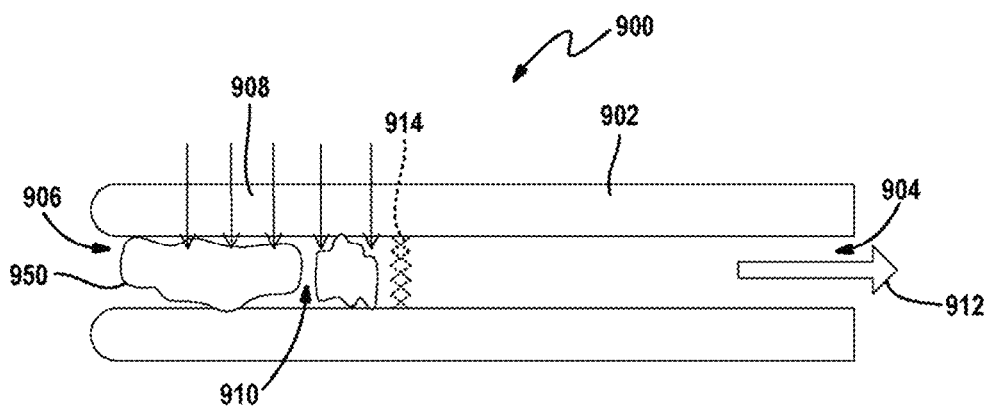
FIG. 9 is an illustration of a biopsy device.

FIG. 9 shows an illustration of a biopsy device 900 for receiving a biological sample 950. The device 900 comprises a body 902 with a first opening 904 and a second opening 906 and at least a portion of an at least partially optically transparent wall 908. The body 902 defines a channel 910 for receiving the biological sample 950, such as a tissue. A source of negative pressure 912 is applied to the first opening 904, which causes the biological sample 950 to be drawn through the second opening 906 and into the channel 910. Images of the biological sample 950 are obtained through the portion of at least partially optically transparent wall 908. In some embodiments, the biopsy device 900 further comprises an optional backstop or perforated wall 914. The backstop or wall comprises a plurality of holes or pores that permits negative pressure to transverse the backstop or wall 914. The backstop or wall 914 blocks tissue from shooting through the biopsy device 900 and maintains the tissue at a region of the device 900 suitable for imaging.

In one embodiment, the device has a region with a cross-sectional geometry that is at least partially rectangular. This geometry simplifies imaging of the tissue without repeated auto-focusing to focus different regions of the device and/or reduces optical aberrations. On the one hand, it is advantageous to minimize an amount of tissue to be removed during biopsy and to keep the channel narrow. On the other hand, it is advantageous to obtain tissue volumes that are as large as possible to improve diagnostic accuracy. This trade-off is application specific. For example at a region of a device where a sample is imaged has a dimension (an "x-dimension") orthogonal to both the axis in which imaging is performed and the axis along which the pressure is applied in the range of from about 100 µm to about 15 mm, from about 500 µm to about 10 mm, or from about 1 mm to about 5 mm. In various embodiments, the x-dimension is about 100 µm, about 200 µm, about 500 µm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. A region of the device where the sample is imaged has a dimension along an axis in which imaging is performed (a "y-dimension") in a range of from about 50 µm to about 1000 µm. In various embodiments, the y-dimension is equal to or less than about 1000 µm, equal to or less than about 500 µm, equal to or less than about 400 µm, equal to or less than about 300 µm equal to or less than about 200 µm equal to or less than about 100 µm. In some embodiments, the y-dimension is from about 10 µm to about 1000 µm, from about 50 µm to about 400 µm, from about 100 µm to about 300 µm, or from about 150 µm to about 250 µm. Accordingly, in various embodiments, the dimension of the device along an axis in which imaging is performed is about 500 µm, about 450 µm, about 400 µm, about 350 µm, about 300 µm, about 350 µm, about 300 µm, about 250 µm, about 200 µm, about 150 µm, or about 100 µm. A region of the device where the sample is imaged has a dimension orthogonal to the axis in which imaging is performed and along which the pressure is applied (a "z-dimension") in the range of from about 100 µm to about 30 mm, from about 1 mm to about 20 mm, from about 1 mm to about 15 mm, or from about 5 mm to about 10 mm. In various embodiments, the z-dimension is about 100 µm, about 200 µm, about 500 µm, about 1 mm, about 2 mm, about 3 mm, about 4 mm, about 5 mm, about 6 mm, about 7 mm, about 8 mm, about 9 mm, about 10 mm, about 15 mm, about 20 mm, about 25 mm, or about 30 mm. Therefore, in various embodiments, the device has a region with x:y:z-dimensions of from about 100 µm:50 µm:100 µm to about 15 mm:1000 µm:30 mm or from about 1 mm:100 µm:1 mm to about 10 mm:250 µm: 15 mm. In one embodiment, the device has a region with x:y:z dimensions of about 10 mm:200 µm:15 mm.

Figure 10:
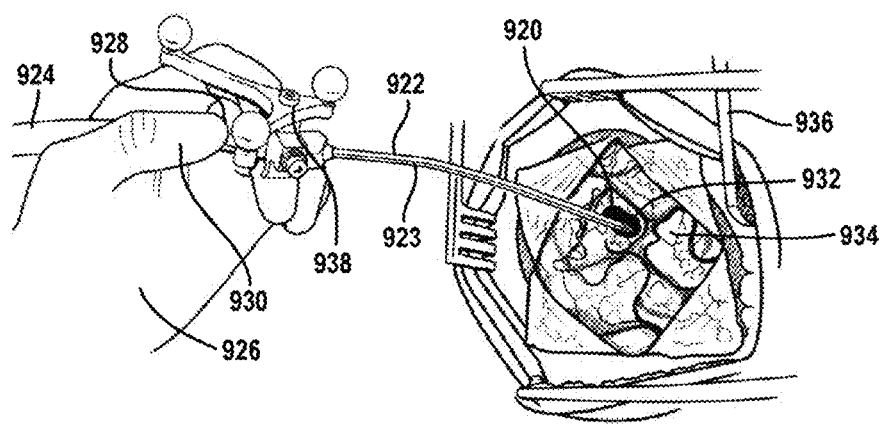
FIG. 10 is an illustration of a biopsy tip attached to a surgical suction device.

In various embodiments, the source of the negative pressure is a building's vacuum system that is accessible through a wall of a room, a freestanding system that generates suction autonomously, or a pump. In another embodiment, the device is configured as a biopsy tip 920 that interfaces with a surgical suction device 922 as shown in FIG. 10. The suction device 922 comprises a longitudinal body 923, which can be rigid or flexible. The biopsy tip 920 can be attached to a surgical suction device 922 that is connected to a source of suction or negative pressure 924 such as a wall that provides access to a building's vacuum system or a pump. The suction device 922 is held by the surgeon's hand 926. As shown in FIG. 10, in some embodiments the suction device 922 includes an opening or aperture 928 that provides a low resistance path from the source of suction 924 to the ambient environment. By partially or completely covering the opening, e.g., by the surgeon's thumb 930, it is possible to finely control an amount of suction applied to the opening of the biopsy tip 920. The suction device 922 and biopsy tip 920 can, for example, be used to take a biopsy from a surgical cavity 932 of exposed brain tissue 934 while holding back skin with surgical clamps 936. The suction device 922 may further include passive or active markers 938 for navigational tracking of the suction device 922 and/or biopsy tip 920, as described further below. Alternatively, a passive or active marker for navigational tracking (e.g., optical or electromagnetic) may also be included as part of each biopsy tip. Different features of the markers could then be used to encode for different biopsy tips.

Imaging can the performed either by imaging the entire assembly (suction device 922 and biopsy tip 920) or by removing the biopsy tip 920 from the suction device 922 and loading only the biopsy tip 920 into the imager separately. In the earlier case, the imaging system is preferably sterile. In the latter case, the surgeon could load another biopsy tip to quickly take multiple additional samples. In another embodiment, surgical resection could be performed with the biopsy tip 920 connected to the suction device 922. When the surgeon reaches a point where a tissue pathology needs to be determined, the last bit of tissue the surgeon sucked up could be used as the sample for imaging.

Figure 11:
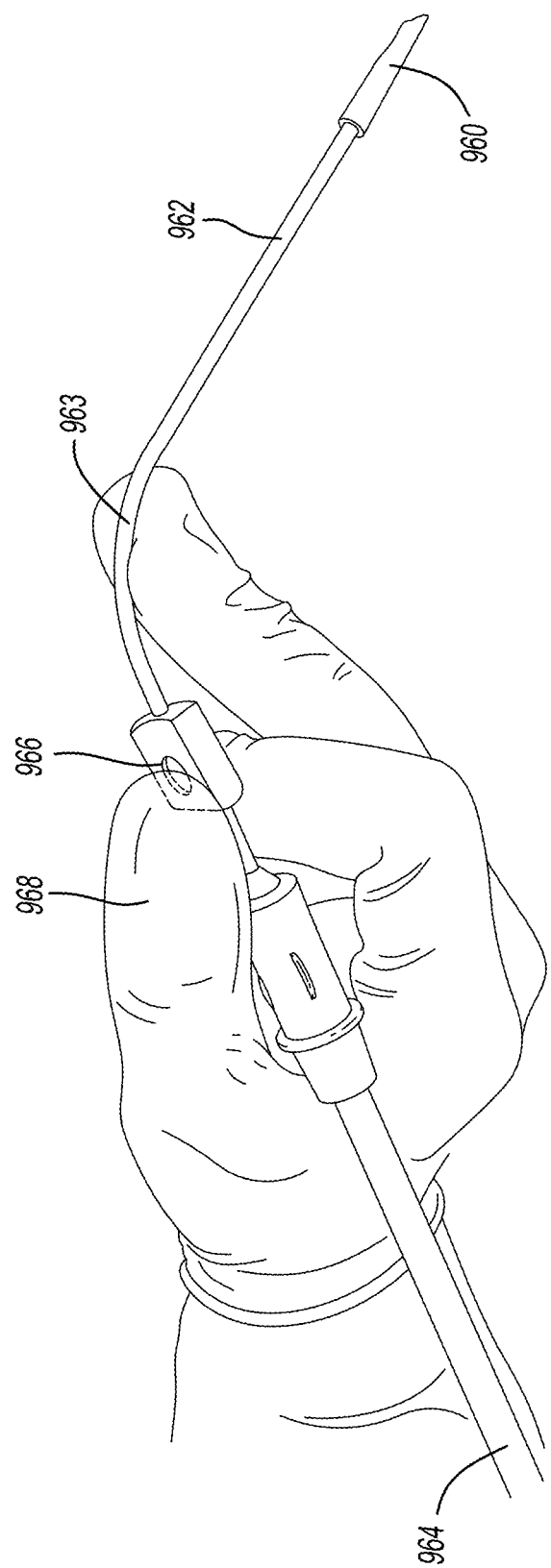
FIG. 11 is a photograph of a biopsy tip attached to a suction device.

FIG. 11 shows a photograph of an exemplary a biopsy tip 960 attached to a standard (V. Mueller; San Diego, Calif.) neurosurgical suction device 962. The suction device 962 has a longitudinal body 963 that is either rigid or flexible. The suction device 962 is attached to a stationary source of negative pressure, such as a hospital's vacuum system, by a conduit or tube 964. The suction may be regulated both by valves and pressure regulators associated with vacuum system and also regulated locally at the site of surgery by a surgeon closing an aperture or opening 966 in the suction device 962 with his or her thumb 968.

In various embodiments, the entire biopsy tip is composed of at least partially optically transparent material and images can be obtained from samples in the biopsy tip in reflection or transmission modes. In other embodiments, only a single portion of the biopsy tip is at least partially optically transparent and imaging is performed in a reflection mode. In yet other embodiments, portions of the biopsy tip on two opposing sides of a sample are at least partially optically transparent while other portions of the biopsy tip are non-transparent and imaging can be performed in either reflection or transmission modes.

In various embodiments, imaging is performed with beams with wavelengths in a spectral range of 790 nm and 1010-1050 nm and "optically transparent" is understood as being transparent to these wavelengths. In other embodiments, excitation beams may have wavelengths in the ranges of from about 0.4 μm to about 10 μm, or from about 0.7 μm to about 10 μm, or from about 0.7 μm to about 2.1 μm, or from about 0.7 μm to about 1.6 μm, from about 0.4 μm to about 1.1 μm, or from about 0.5 μm to about 1.1 μm and "optically transparent" is understood as being at least partially optically transparent to these wavelengths. "Partially optically transparent" refers to a material having an optical transmission of greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, greater than or equal to about 90%, greater than or equal to about 95%, greater than or equal to about 98%, or greater than or equal to about 99%. Anti-reflection coatings can be used to achieve improved transmission relative to transmission that can be achieved without anti-reflection coatings.

The biopsy device is composed of any material that is characterized by having optical properties suitable for imaging. Preferably, the material a low probability of splintering, does not cause optical aberrations, is not birefringent, capable of withstanding excitation laser power, and either not Raman active in the region where imaging is performed or Raman active in the spectral region where imaging is performed. As used herein, "Raman-active" refers to a material that generates a Raman shift (Stokes or anti-Stokes) at a particular spectral region, such as from about 2800 cm$^{-1}$ to about 3100 cm$^{-1}$. Signal from the material may cause an undesirable background signal with respect to the tissue images and it is preferred to use a material that is not Raman active in the spectral region in such cases. In another embodiment, the Raman signal from the material does not interfere with the tissue imaging because it is out of focus and the material can be Raman active. In this case, the imaging system can be configured to also image in or near the material to provide spectral calibration and or field flattening. In various embodiments, as non-limiting examples, materials for imaging include glass, quartz, plastics, polysiloxanes, polydimethylsiloxane (PDMS), polysiloxane-urea/urethane copolymers, polyurethanes, polyureas, polyethers, polyesters, polyacrylates and polymethacrylates (including poly(methyl methacrylate) (PMMA), poly-(ethylmethacrylate) (PEMA), or (poly)-butyl methacrylate-co-methyl methacrylate (PBMMA)), polycarbonates, polystyrenes, polyamides, polyvinyl esters or polyolefins such as, for example, polyethylene, poly-butadiene, ethylene-olefin copolymers, styrene-butadiene copolymers, cyclic olefin copolylmer (COC), such as TOPAS® COC commercially available from Topas Advanced Polymers, poly-chloro-trifluoro-ethylene (PCTFE), such as ACLAR® PCTFE commercially available from Honeywell, and polyethylene terephthalate when the materials are configured to exhibit the optical properties described above. Combinations or derivatives of suitable materials can also be used when the combination exhibits the desired optical properties.

Figure 13B:
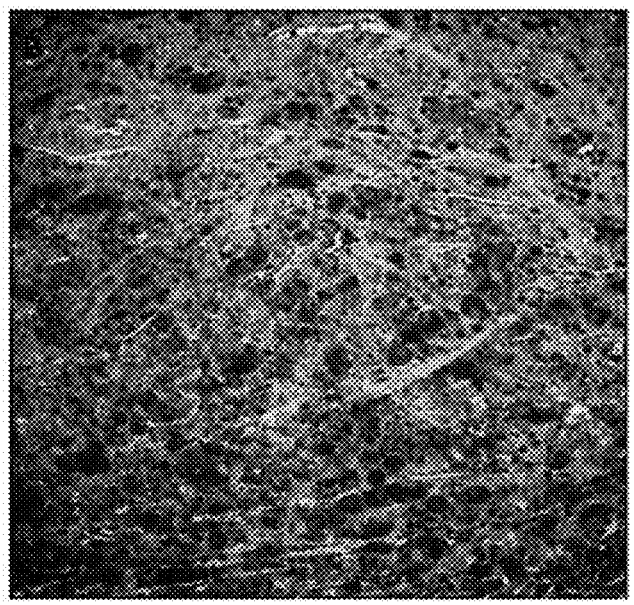
FIG. 13B is a stimulated Raman scattering SRS image of a brain tissue mounted in a channel.

CRS imaging can be performed when a biopsy tip is composed of a plastic for mounting the sample. FIG. 13B shows a two-color SRS image of human brain tissue with a 200 μm clear plastic channel. While there is some out-of-focus SRS signal from the plastic, it is easily subtracted and the image quality as good as compared to more cumbersome sample preparation methods using a coverslip, cover slide and double-sided stick tape as used to acquire the images of FIG. 5 or the rectangular glass capillary used in generating the image of FIG. 13A. Accordingly, the biopsy device may be composed of glass, a plastic, or any of the suitable materials described herein.

A Raman signal in the high-wavenumber region of Raman spectra, where all of the examples of clinically relevant CRS imaging provided herein have been performed, is typically from C—H-type vibrations. In one embodiment the biopsy device may be composed of a material where a portion of hydrogen atoms have been replaced with deuterium atoms to generate a material that is less Raman active in the spectral region of interest.

In other embodiments, Raman activity outside of the spectral region of interest may be a welcomed side effect because the signal could be used for spectral calibration of the imaging system, for imaged based auto-focus and/or for field flattening.

Figure 12A:
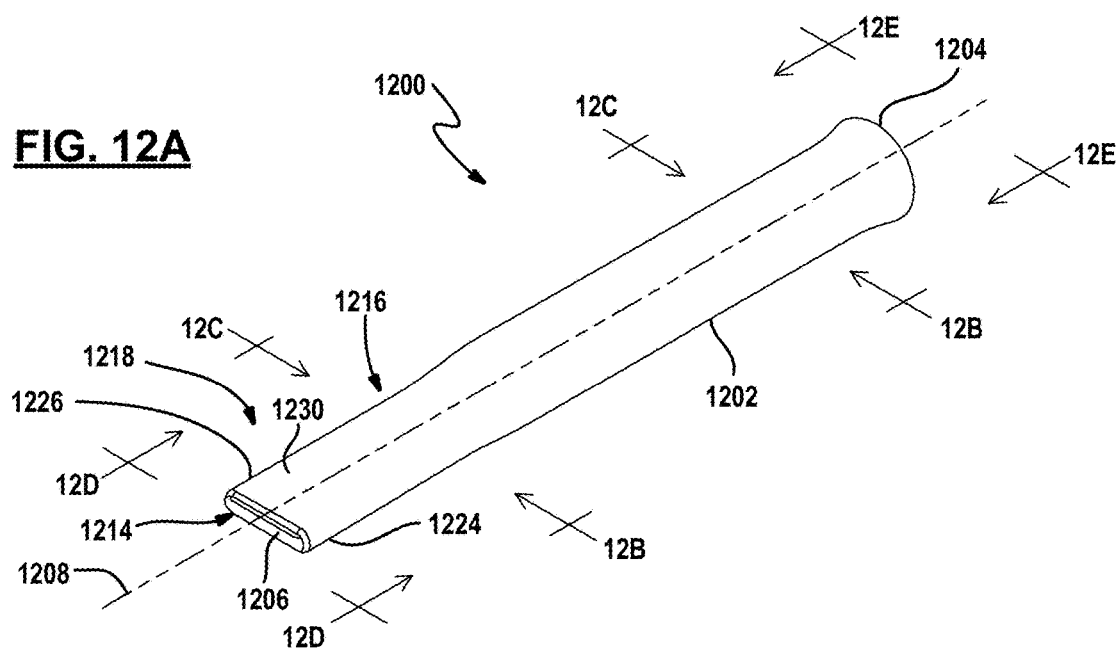
FIG. 12A is an illustration of a biopsy device configured as a biopsy tip.
Figure 12B:
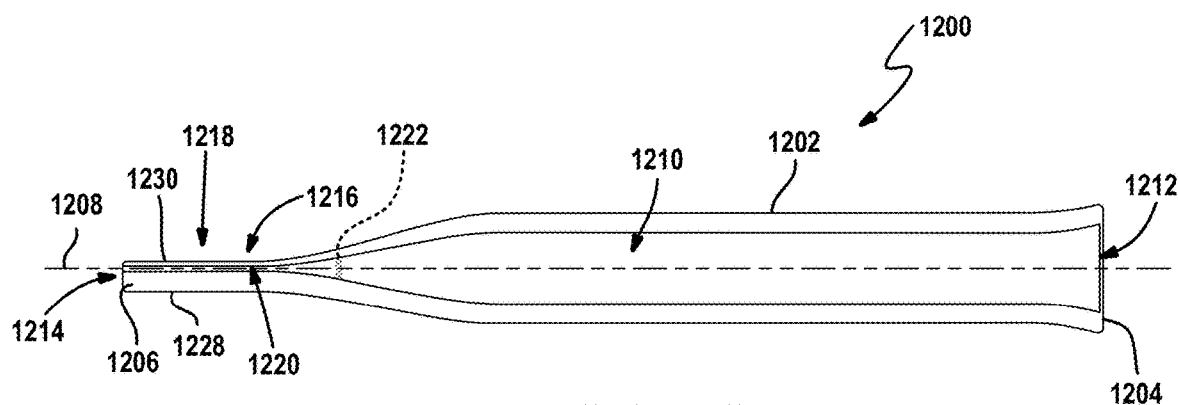
FIG. 12B is a cross-section view of the biopsy device of FIG. 12A taken along line 12B.
Figure 12C:
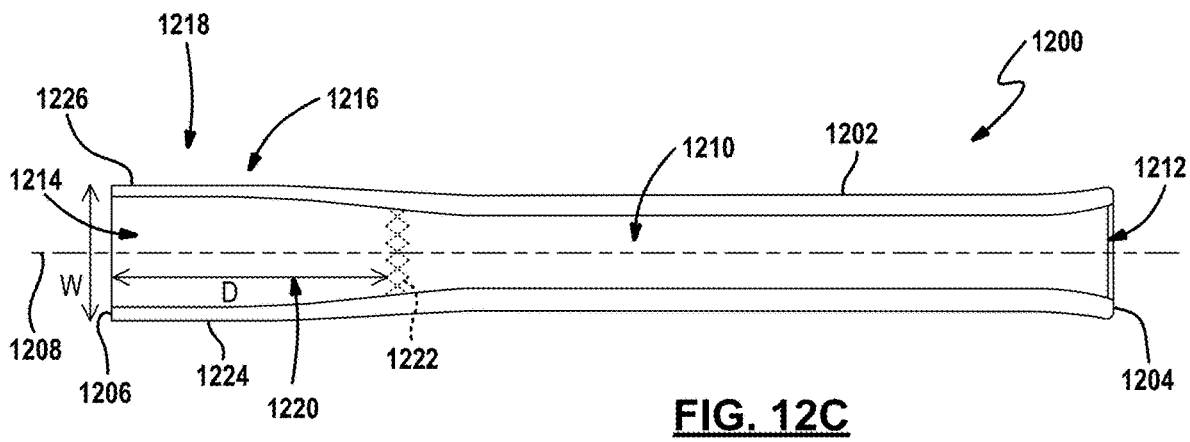
FIG. 12C is a cross-section view of the biopsy device of FIG. 12A taken along line 12C.
Figure 12D:
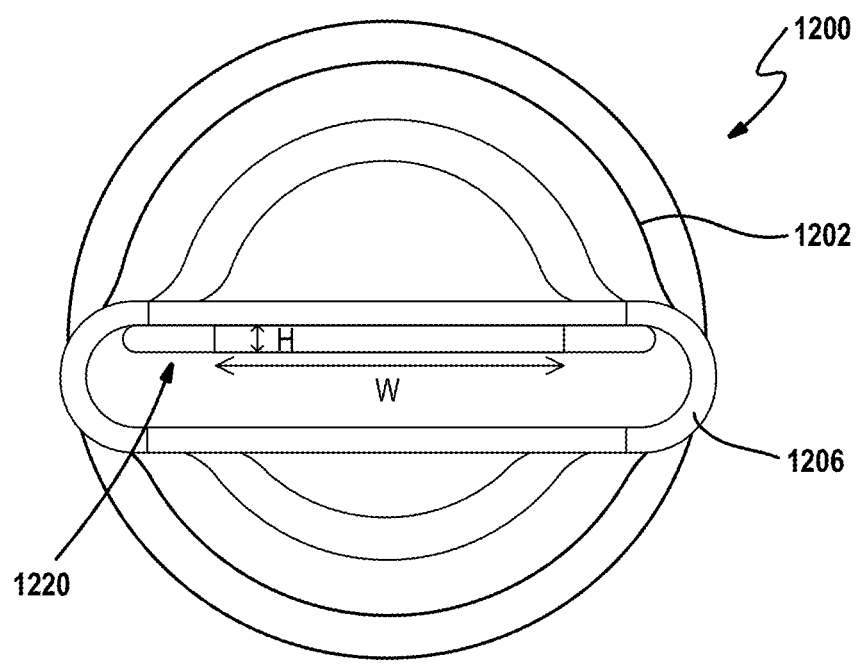
FIG. 12D is a perspective view of the biopsy device of FIG. 12A taken along line 12C.
Figure 12E:
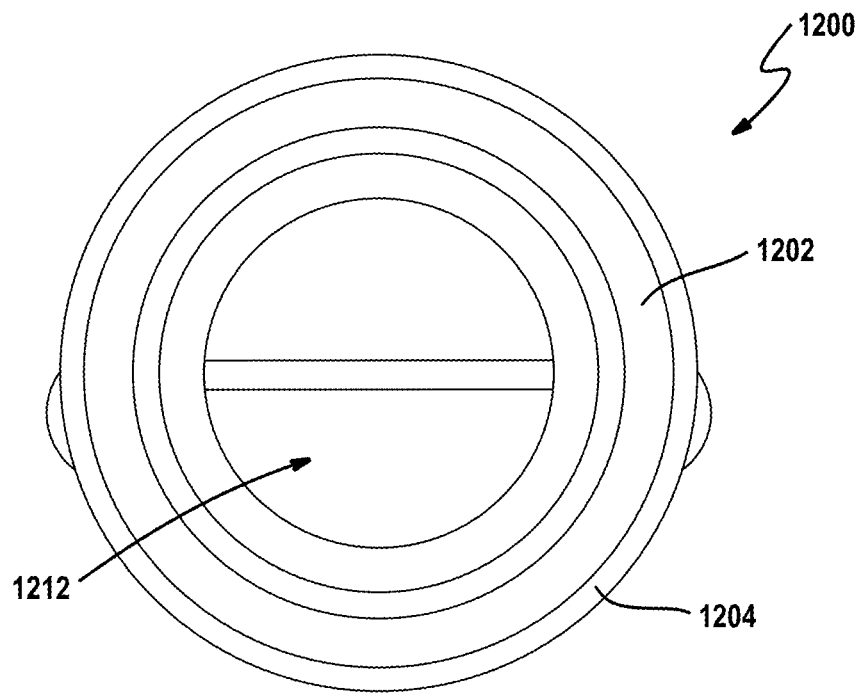
FIG. 12E is a perspective view of the biopsy device of FIG. 12A taken along line 12E.

FIGS. 12A-12E show detailed three-dimensional drawings of an exemplary biopsy device 1200. FIG. 12B is a cross-section view of the biopsy device 1200 of FIG. 12A taken along line 12B. FIG. 12C is a cross-section view of the biopsy device 1200 of FIG. 12A taken along line 12C. FIG. 12D is a perspective of the biopsy device 1200 of FIG. 12A taken along line 12D. FIG. 12E is a perspective of the biopsy device 1200 of FIG. 12A taken along line 12E.

The biopsy device 1200, which is configured as a biopsy tip, comprises a hollow body 1202, also referred to as the "body", extending from a first end 1204 to a second end 1206, such as an opposite second end 1206. In some embodiments, the hollow body 1202 defines a central longitudinal axis 1208. In other embodiments, the hollow body 1202 is curved or acentric. The body 1202 comprises a central bore or hollow interior 1210 that extends from a first opening 1212 at the first end 1204 to a second opening 1214 at the second end 1206. The body 1202 also defines a sample collecting portion 1216 at or adjacent to the second end 1206. In some embodiments, the body 1202 defines a tapered region that comprises the sample collecting portion 1216. As used herein, the "sample collecting portion" is a portion of the device 1200 where a biological sample is located during imaging. In other words, during use, a biological sample is drawn into the biopsy device 1200 and maintained at the sample collecting portion 1216. Therefore, the "sample collecting portion" is also referred to as a "sample imaging portion." As shown in FIGS. 12A-12C, the sample collecting portion 1216 is positioned at or adjacent to the second end 1206. However, in other embodiments, the sample collecting portion is positioned at a middle region or the near the first end 1204 of the biopsy device 1200. Therefore, the location or position of the sample collecting portion or sample imaging portion 1216 is not limiting.

The body 1202 can have a length from the first end 1204 to the second end 1206 of from about 1 cm to about to about 20 cm, or from about 2 cm to about 15 cm, or from about 3 cm to about 10 cm. In some embodiments, the body 1202 has a length of about 1 cm, about 2 cm, about 3 cm, about 4 cm, about 5 cm, about 6 cm, about 7 cm, about 8 cm, about 9 cm, about 10 cm, about 12 cm, about 14 cm, about 16 cm, about 18 cm, or about 20 cm. The body 1202 can have a width from a first side orthogonal to the first and second ends 1204, 1206 to a second side orthogonal to the first and second ends 1204, 1206 of from about 2 mm to about 30 mm, or from about 3 mm to about 20 mm, or from about 5 mm to about 10 mm. In some embodiments, the body 1202 has a width of about 2 mm, about 3 mm, about 4 mm, about 5 mm, about 6 mm, about 7, mm, about 8 mm, about 9 mm, about 10 mm, about 12 mm, about 14 mm, about 16 mm, about 18 mm, or about 20 mm. Therefore, in various embodiments, the biopsy device 1202 has a length and width that are substantially equal. In other embodiments, the body 1202 has a length that is longer than the width; providing an elongate hollow body 1202. Moreover, the body 1202 of the biopsy device 1200 may be symmetrical or asymmetric. For example, an asymmetric body 1202 is utilized in some embodiments where the device 1200 must be inserted into an imaging device in a specific orientation.

The first opening 1212 is operable to receive, a source of negative pressure. For example, a stationary vacuum source (e.g., a building's vacuum system) or a pump may be suitable sources of negative pressure, which is extended to the biopsy device 1200 by a conduit or tube extending from a wall of the building or from the pump. In some embodiments, the conduit or tube providing the negative pressure is coupled to an end of a surgical suction device (such as, for example, the suction device 922 of FIG. 10 or the suction device 962 of FIG. 11) and the biopsy device 1200 is removably coupled to an opposing end of the surgical suction device. The biopsy device 1200 is removably coupled to the tube or surgical suction device by any means known in the art, including, for example, by interference or press fit, luer fit, bayonet slots, or threading. In embodiments where the biopsy device 1200 is coupled to the tube or suction device by interference or press fit, the body 1202 can flare outward at the first end 1206 to promote coupling as shown in FIGS. 12A-12C.

The second opening 1214 is operable to receive a biological sample from a patient. The patient may be a human or non-human mammal, such as, for example, a horse, dog, or cat. However, it is understood that the patient can be any animal undergoing a medical procedure. The biological sample is a piece of tissue or biopsy that is sucked or drawn through the second opening 1214 and into the sample collecting portion 1216 of the device 1200 in conjunction with use of negative pressure or suction. In various embodiments, the tissue is a sample of an organ from a subject, such as, for example, a brain, breast, liver, lung, prostate, colon, stomach, or pancreas. However, it is understood that the tissue can be any tissue collected by a medical practitioner that requires compositional and/or structural analysis. As described herein, in various embodiments the tissue is a sample of brain, which may be infiltrated to some extent by a tumor or malignant cancer cells. Although the sample collecting portion 1216 is positioned near the second end 1206 in some embodiments, the second end 1216 of the body 1202 is not configured to piece, cut or stab into a tissue in order to receive a biological sample for imaging. Instead it is configured to suck up or draw tissue from the surface of a surgical cavity.

The biopsy device 1200 also includes an optically transparent region 1218 that is disposed, positioned, or located in a region corresponding to the sample collecting portion 1216. The optically transparent region 1218 is at least partially transparent (as defined above) to an excitation beam and to an optical signal generated by a biological sample after interacting with an excitation beam. The optically transparent region 1218 is positioned such that an imaging device can capture an image of a biological sample in the sample collecting portion 1216 through the optically transparent region 1218. Accordingly, the optically transparent region 1218 is configured to, or capable to, transmit electromagnetic radiation therethrough from an imaging device capable of imaging a biological sample when disposed in the sample collecting portion 1216. In some embodiments, the entire biopsy device 1200 comprises the optically transparent region 1218. In other words, in these embodiments the entire device body 1202 is optically transparent. In other embodiments, only a portion of the body 1202 is optically transparent, such as a portion adjacent to the sample collecting portion 1216. The optically transparent region 1218 is composed of any material known in the art that is optically transparent, such as optically clear glasses or plastics, as described above. Moreover, the optically transparent region 1218 may or may not be Raman active in a predetermined region depending on a user's preference.

The central bore 1210 defines a collection channel 1220 at the sample collecting portion 1216. The collection channel 1220 is substantially planar and has a cross-sectional geometry. Any cross-sectional geometry that allows for sample collection and imaging may be used. As a non-limiting example, and as shown in FIGS. 12A-12E, the cross-sectional geometry may be rectangular. Therefore, the cross-section geometry of the biopsy device 1200 may be different at the sample collecting portion 1216 than at the remaining portions of the biopsy device 1200. As shown in FIG. 12D, the collection channel 1220 has a height H and a width W, and as shown in FIG. 12C, the collection channel 1220 has a depth D. In other embodiments, the collection channel 1220 has a top surface, or ceiling, that is substantially planar and an opposing bottom surface, or floor, that is substantially planar. However, walls orthogonal to the top and bottom surfaces may be concave or convex. However, in such embodiments similar constraints for the height H, width W and depth D are applicable. In many embodiments, the height H is configured such that a sufficient amount or level of negative pressure or suction is provided at the second end 1208 for aspirating a biological sample into the collection channel 1220 and such that an image of the biological sample can be captured with a sufficient quality and resolution. The forcefulness of the negative pressure or suction is determined primarily by the degree of negative pressure being applied. Pressures are typically measured by gauge pressure, which is the pressure above or below ambient atmospheric pressure. The atmospheric pressure that indicates as zero on ordinary pressure gauges is 760 mmHg, which is normal pressure at sea level. Negative pressure is therefore, defined as pressure less than atmospheric pressure or pressure less than zero (atmospheric) on a pressure gauge. In some embodiments the negative pressure or suction is from about 10 mmHg to about 550 mm Hg, from about 10 mmHg to about 50 mmHg, from about 50 mmHg to about 100 mmHg, from about 100 mm Hg to about 150 mmHg, from about 150 mm Hg to about 200 mmHg, from about 200 mmHg to about 250 mmHg, from about 250 mmHg to about 300 mmHg, from about 300 mmHg to about 350 mmHg, from about 350 mmHg to about 400 mmHg, from about 400 mm Hg to about 450 mmHg, from about 450 mmHg to about 500 mmHg, from about 500 mmHg to about 550 mmHg. In some embodiments, the negative pressure or suction is above 550 mmHg. Accordingly, the level of pressure or suction, in various embodiments, is about 10 mmHg, about 25 mmHg, about 50 mmHg, about 75 mmHg, about 100 mmHg, about 150 mmHg, about 200 mmHg, about 250 mmHg, about 300 mmHg, about 350 mmHg, about 400 mmHg, about 450 mmHg, about 500 mmHg, about 550 Hg, or higher. In some embodiments, the level of pressure is about 180 mmHg, which is about the level of negative pressure or suction supplied by a hospital's static vacuum system that is accessible through ports on the hospital's walls, which can also be duplicated by a pump.

An image has a sufficient quality and resolution when a surgeon or other medical practitioner can analyze the image and determine the composition of the image's corresponding sample. In other words, the image has a sufficient quality and resolution when a surgeon or other medical practitioner can readily, i.e., during a surgical procedure, determine whether a sample of tissue is infiltrated with cancer cells. As described above, the height H is equal to or less than about 500 μm, equal to or less than about 400 μm, equal to or less than about 300 μm equal to or less than about 200 μm equal to or less than about 100 μm. In some embodiments, the height H is from about 10 μm to about 500 μm, from about 50 μm to about 400 μm, from about 100 μm to about 300 μm, or from about 150 μm to about 250 μm. Accordingly, in various embodiments, the height H is about 500 μm, about 450 μm, about 400 μm, about 350 μm, about 300 μm, about 350 μm, about 300 μm, about 250 μm, about 200 μm, about 150 μm, or about 100 μm. The width W is from about 100 μm to about 15 mm, from about 500 μm to about 10 mm, or from about 1 mm to about 5 mm. In various embodiments, the width W is about 10 μm, about 200 μm, about 500 μm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. However, as shown in FIG. 12C, the width W may slightly decrease as the collection channel 1224 extends from the second end 12008 of the device 1200 to the first end 1206 of the device. The depth D is from about 100 μm to about 30 mm, from about 1 mm to about 20 mm, or from about 5 mm to about 15 mm, or from about 5 mm to about 10 mm. In various embodiments, the depth D is about 100 μm, about 200 μm, about 500 μm, about 1 mm, about 2 mm, about 3 mm, about 4 mm, about 5 mm, about 6 mm, about 7 mm, about 8 mm, about 9 mm, about 10 mm, about 15 mm, about 20 mm, about 25 mm, or about 30 mm. For example, when the width W and depth D are both 4 mm, an image can be developed with an area of up to 4 mm×4 mm. The device 1200 allows an axial resolution that is higher than each dimension of the sample collecting portion 1216 along an axis in which imaging is performed.

In some embodiments, the sample collecting portion 1216 of the device 1200 optionally further comprises a backstop or perforated wall 1222. The backstop or wall 1222 comprises a plurality of holes or pores that permits negative pressure to transverse the backstop or wall 1222. The backstop or wall 1222 blocks a biological sample from shooting through the biopsy device 1200 and maintains the biological sample within the sample collecting portion 1216 of the device 1200 for imaging. The optional backstop or perforated wall 1222 is positioned within the central bore 1210 of the body 1202 at or near a distance equal to the depth D of the collection channel 1220 from the second end 1206 of the device 1200.

The sample collecting portion 1216 of the biopsy device 1200 includes the collection channel 1220 and the optically transparent region 1218 of the device body 1202. As shown in FIGS. 12A-12D, the sample collecting portion 1216 is substantially planar with relatively short ends 1224, 1226 with sizes dependent on the channel height H. The sample collecting portion 1216 also has a first substantially planar surface 1228 and a second substantially planar surface 1230 that are substantially orthogonal to the ends 1224, 1226. At least one of the first planar surface 1228 or the second planar surface 1230 is configured with optically transparent region 1218 of the device body 1202. In embodiments where a biological sample positioned in the collection channel 1220 is to be imaged in transmission mode, both the first surface 1228 and the second surface 1230 are include an optically transparent material to define the optically transparent region 1218. In embodiments where a biological sample positioned in the collection channel 1220 is to be imaged in reflection mode, at least one of the first surface 1228 or the second surface 1230 includes an optically transparent material to define the optically transparent region 1218. In other words, when both the first surface 1228 and the second surface 1230 are include an optically transparent material to define the optically transparent region 1218 a biological sample in the collection channel 1220 can be imaged in either transmission mode or reflection mode and when only one of the first surface 1228 or the second surface 1230 includes an optically transparent material to define the optically transparent region 1218 a biological sample in the collection channel 1220 can only be imaged in reflection mode. The thickness of the body 1202 at the first surface 1228 and at the second surface 1230 are configured to permit excitation beams to focus on and interact with a biological sample positioned in the collection channel 1220. In various embodiments, the first surface 1228 has a thickness that is substantially equal to the thickness of a microscope slide and the second surface 1230 has a thickness that Is substantially equal to the thickness of a No. 1.5 coverslip. Accordingly, an excitation light path and collection light path are included in the body 1202 of the device 1200 at the sample collecting portion 1216. In various embodiments, the body 1202 of the biopsy device 1200 at the excitation and collection light paths are individually from about 50 μm to about 2 mm, or from about 75 μm to about 1.5 mm, or from about 100 μm to about 1 mm, or from about 150 μm to about 500 μm, or from about 200 μm to about 150 μm.

In some embodiments, the biopsy device 1200 further comprises a regulator or pressure controlling regulator for controlling the amount or level of negative pressure provided by the biopsy device 1200. The regulator can be an aperture or a valve disposed on the elongate body 1202 permitting fluid communication between an external surface and the central bore 1210 or interior portion of the biopsy device 1200. For example, a an aperture can be partially covered by a finger or thumb to control the amount of negative pressure in the central bore 1210 or a valve can be turned to control the amount of negative pressure in the central bore 1210. In some embodiments, the regulator is a member of a surgical suction device to which the biopsy device attaches. In other embodiments, the amount of negative pressure in the central bore 1210 is controlled by a pressure controlling regulator positioned on a suction device to which the biopsy device 1200 is removably coupled. As non-limiting examples, the suction device can be the suction device 922 of FIG. 10 or the suction device 962 of FIG. 11, as described above. The pressure controlling regulator on the suction device can be an aperture or a valve as described above.

As discussed further below, a biopsy device, such as the biopsy device 1200, can be used with navigational equipment for recording coordinates of a biological sample or biopsy to provide recorded coordinates corresponding to a location of collection of the biological sample or biopsy. By displaying pre-operative or intra-operative macroscopic imaging data at the recorded coordinates, a surgeon or other medical practitioner can determine if the region where the biological sample was taken is infiltrated with malignant cancer cells. By repeating this process, the surgeon or medical practitioner can determine the border of a tumor so that tissue comprising the tumor or tumor cells can be safely removed while minimizing removal of normal, healthy tissue.

In embodiments where the entire device 1200 is composed from an at least partially optically transparent material such as a clear plastic or glass, it can be manufactured in a single step by injection molding, extrusion or three-dimensional printing. In other embodiments, the device 1200 can be manufactured in a two-step process including injection molding, extrusion or three-dimensional printing and a secondary process, such as squeezing, melting, thermobinding, and/or gluing. Therefore, the biopsy device 1200 can be a unitary monolithic structure. The biopsy device 1200 could also be assembled from two or more pieces that are combined either mechanically, by glue, and/or thermo-annealing. For example the bottom or floor of the collection channel 1220 can be injection molded to form a first unit and a second unit can then be thermo-annealed to the first unit to form the top or ceiling of the collection channel 1220. This method can be advantageous in a situation where injection molding cannot provide a desired aspect ratio.

The various embodiments, the biopsy device 1200 is configured to be removably coupled to a surgical suction device that transmits negative pressure provided by a pump or vacuum system through the device 1200. Accordingly, the biopsy device 1200 can receive a biological sample in the collection channel 1220 of the sample collecting portion 1216 and be directly analyzed in an imaging device to provide compositional and/or structural and optionally navigational information about the sample within second or minutes, for example, in about 20 minutes or less, in about 15 minutes or less, in about 10 minutes or less, in about 5 minutes or less, in about 4 minutes or less, in about 3 minutes or less, in about two minutes or less, or in about 1 minute or less. In some embodiments, the information is provided immediately or in from about 10 seconds to about 20 minutes, from about 10 seconds to about 15 minutes, from about 10 seconds to about 10 minutes, from about 10 seconds to about 5 minutes, or from about 10 seconds to about 2 minutes. Accordingly, the information can be provided in about 10 seconds, about 20 seconds, about 30 seconds, about 40 seconds, about 50 seconds, about 1 minute, about 1.5 minutes, about 2 minutes, about 2.5 minutes, about 3 minutes, about 3.5 minutes, about 4 minutes, about 4.5 minutes, about 5 minutes, about 6 minutes, about 7 minutes, about 8 minutes, about 9 minutes, about 10 minutes, about 12 minutes, about 15 minutes, about 18 minutes, or about 20 minutes.

A second, modular biopsy device 1250 is shown in FIGS. 14A-14G. The biopsy device 1250 comprises a body 1252 that extends from a first end 1254 to an opposing second end 1256. The body 1252 defines a suction-coupling portion 1258 at or near the first end 1254 and a sample collecting portion 1260 at or near the second end 1256. The suction-coupling portion 1258 defines a central bore 1262 that extends from a first opening 1264 at the first end 1254 to the sample collecting portion 1260. The suction-coupling portion 1258 is operable to receive a source of negative pressure by way of the first opening 1264.

The sample collecting portion 1260 comprises a surface 1266 and walls 1268 orthogonal to the surface 1266. A second surface 1270 is disposed on the walls 1268 of the sample collecting portion 1260. The second surface 1270 is planar or substantially planar and is at least partially optically transparent. By substantially planar, it is meant that the second surface 1270 may deviate from being planar, i.e., may be convex or concave. In some embodiments, the second surface 1270 is a microscope slide. The second surface 1270 can be coupled to the walls 1268 by any means known in the art, such as with clamps, an adhesive, or seating in grooves, as non-limiting examples. When the second surface 1270 is disposed on the walls 1268, the sample collecting portion 1260 defines a collection channel 1272 that extends from a second opening 1274 at the second end 1256 to the suction-coupling portion 1258. The collection channel 1272 is in fluid communication with the central bore 1262, such that when negative pressure (such as the negative pressures described above) is applied to the first opening 1264, air and material, such as biological material is aspirated through the second opening 1274 and the collection channel 1272. In various embodiments, the collection channel 1272 is coupled to the central bore 1262 by way of a hollow intermediate section 1276. As described further below, the body 1252 also optionally includes a positioning surface 1278 that is used for aligning the at least partially optically transparent second surface 1270 with a detection window. Moreover, the biopsy device 1250 may include a backstop or perforated wall in the collection channel 1272 that stops biological material from shooting through the central bore 1262. The backstop or perforated wall may be permanently disposed in the collection channel 1272 or it may be inserted and removed from the collection channel 1272 as desired, such as, for example, by sliding through the walls 1268 or first surface 1266. When a biological sample is aspirated into the collection channel 1272 of the sample collecting portion 1260 of the biopsy device 1250, light may pass through the second surface 1270 and interact with the biological sample.

Figure 14A:
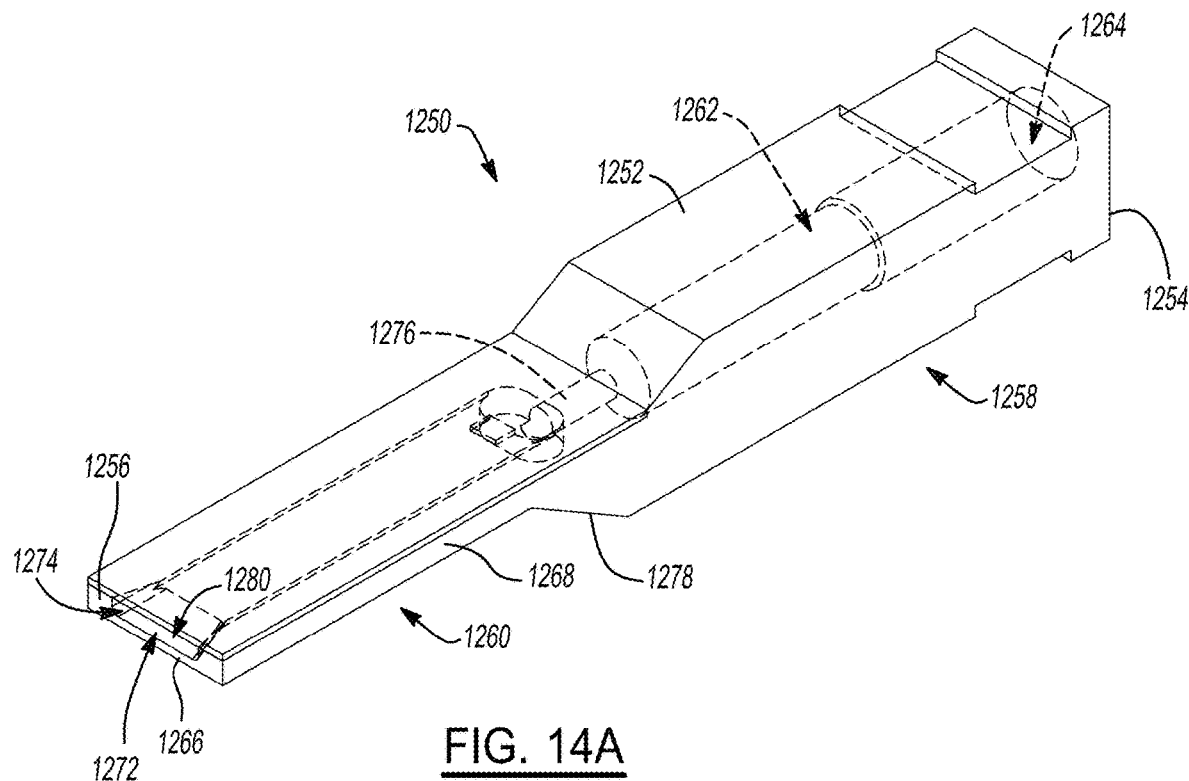
FIG. 14A is a perspective view of a biopsy device according to certain aspects of the current technology.
Figure 14B:
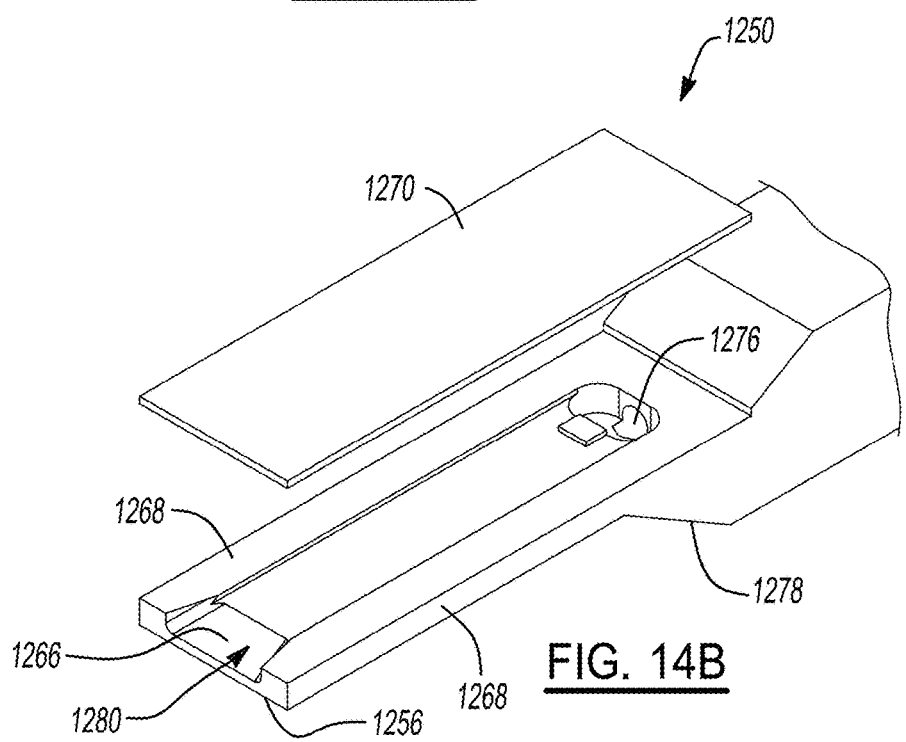
FIG. 14B is an exploded illustration of the biopsy device according to FIG. 14A.
Figure 14E:
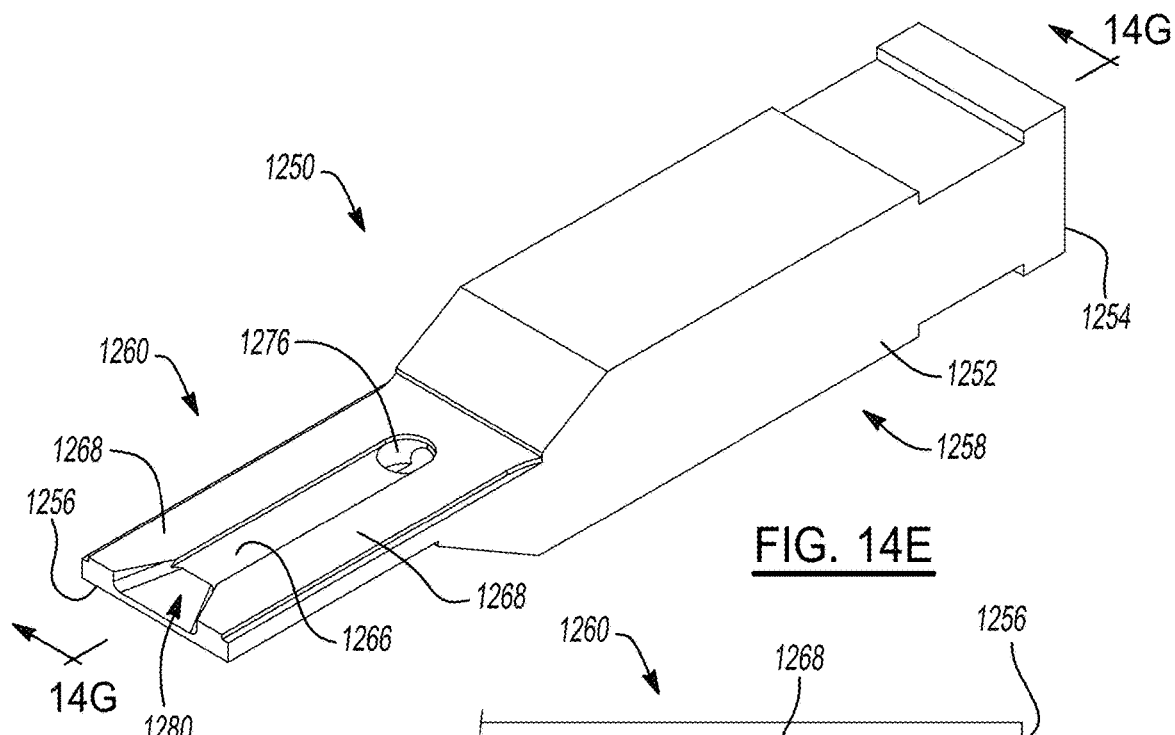
FIG. 14E is a perspective view of a lower portion of the biopsy device of FIG. 14A.
Figure 14F:
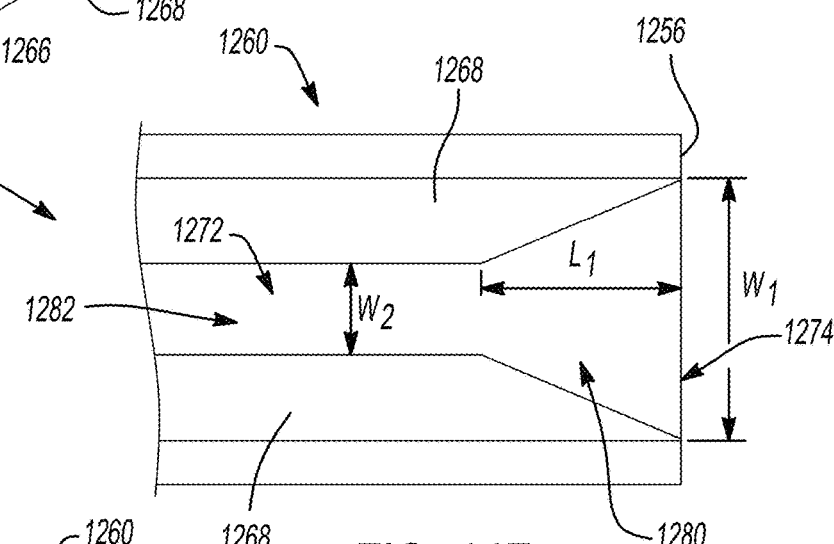
FIG. 14F is a partial top view of the biopsy device of FIG. 14E.
Figure 14G:
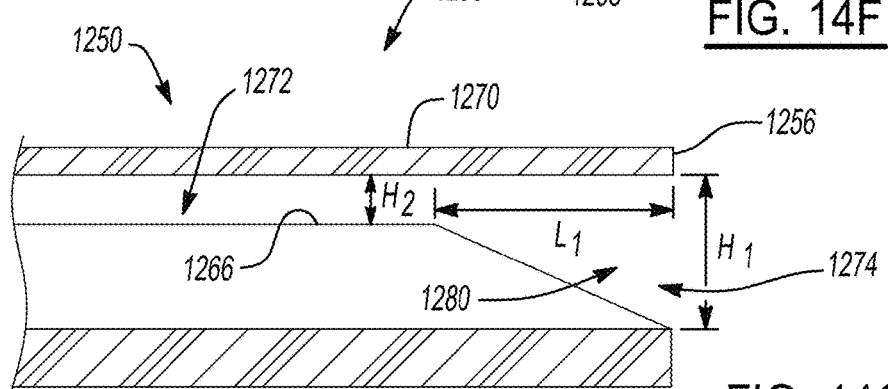
FIG. 14G is a cross-sectional side view of the biopsy device of FIG. 14E taken along line 14G.

In order to provide sufficient aspiration of biological material through the biopsy device 1250, the sample collecting portion 1260 includes a funnel-like sample introduction section 1280 that is configured to allow biological tissue to flow freely, i.e., without clumping or clogging, the collection channel 1272. The sample introduction section 1280 includes surfaces that guide biological material into the collection channel 1272. Accordingly, the sample introduction section 1280 includes the second opening 1274, and the second opening 1274 has a first width that gradually decreases to a second width within the sample introduction section 1280. Moreover, the second opening 1274 has a first height that gradually decreases to a second smaller height within the sample introduction section 1280. As shown in FIG. 14F, the walls 1268 slant inward from the second end 1256 of the biopsy device 1250 to a middle section 1282 of the collection channel 1272, such that the collection channel 1272 has a first width $W_1$ at the second opening 1274 that decreases for a length $L_1$ in the direction from the second end 1256 toward the first end 1254 to a second width $W_2$. In various embodiments, the first width $W_1$ is from about 100 µm to about 10 mm, such as a width of about 100 µm, about 500 µm, about 1 mm, about 2 mm, about 3 mm, about 4 mm, about 5 mm, about 6 mm, about 7 mm, about 8 mm, about 9 mm, or about 10 mm and the second width $W_2$ is from about 50 µm to about 8 mm, such as about 50 µm, about 100 µm, about 250 µm, about 500 mm, about 750 µm, about 1 mm, about 2 mm, about 3 mm, about 4 mm, about 5 mm, about 6 mm, about 7 mm, or about 8 mm. the length $L_1$ can be a length of from about 100 µm to about 20 mm, such as a length of about 100 µm, about 500 µm, about 1 mm, about 2 mm, about 3 mm, about 4 mm, about 5 mm, about 6 mm, about 7 mm, about 8 mm, about 9 mm, about 10 mm, about 15 mm, or about 20 mm. As shown in FIG. 14G, the surface 1266 slopes toward the second surface 1270 from the second end 1256 of the biopsy device 1250 toward the first end 1254, such that the collection channel 1272 has a first height $H_1$ at the second opening 1274 that decreases for a length $L_1$ in the direction from the second end 1256 toward the first end 1254 to a second height $H_2$. In various embodiments, the first height $H_1$ is from about 10 µm to about 5 mm, such as a height of about 10 µm, about 50 µm, about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, or about 5 mm and the second height $H_2$ is from about 5 µm to about 2 mm, such as about 5 µm, about 10 µm, about 50 µm, about 100 µm, about 200 µm, about 300 µm, about 400 µm, about 500 µm, about 600 µm, about 700 µm, about 800 µm, about 900 µm, about 1 mm, or about 2 mm.

Figure 15A:
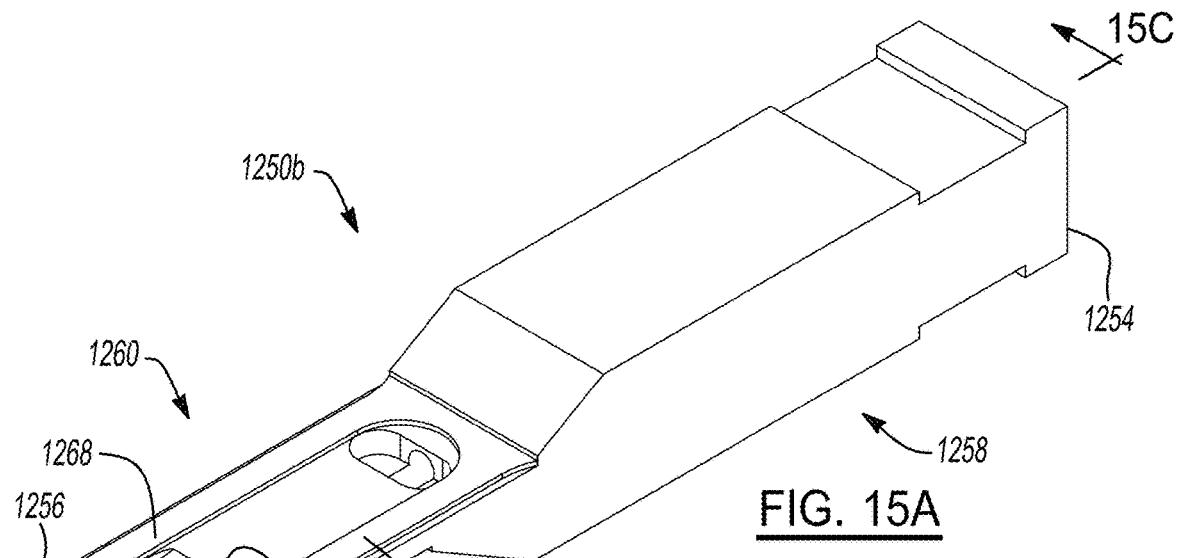
FIG. 15A is an illustration of a biopsy device according to various aspects of the current technology.
Figure 15B:
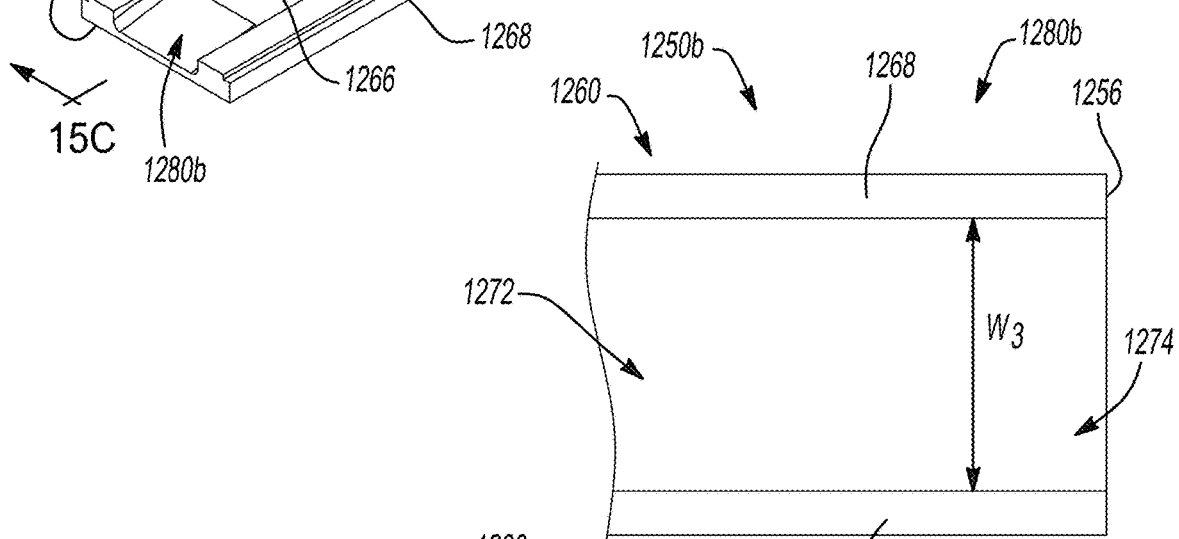
FIG. 15B is a cross-sectional top view of the biopsy device of FIG. 15A.
Figure 15C:
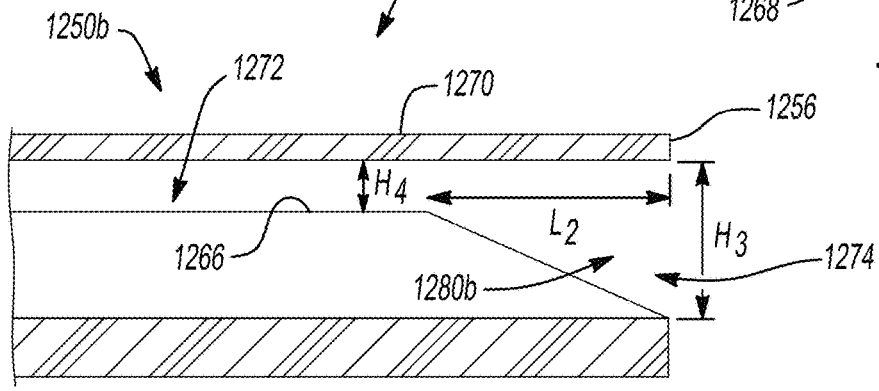
FIG. 15C is a cross-sectional side view of the biopsy device of FIG. 15A taken along line 15C.

FIGS. 15A-15C show a biopsy device 250b that is similar to the biopsy device 250 of FIGS. 14A-14G. However, the biopsy device 250b has a sample introduction section 1280b that differs from the sample-introduction section 1280. As shown in FIG. 15B, the walls 1268 are substantially straight, such that the collection channel 1272 has a single width W3 of from about 100 µm to about 10 mm, such as a width of about 100 µm, about 500 µm, about 1 mm, about 2 mm, about 3 mm, about 4 mm, about 5 mm, about 6 mm, about 7 mm, about 8 mm, about 9 mm, or about 10 mm. As shown in FIG. 15C, the surface 1266 slopes toward the second surface 1270 from the second end 1256 of the biopsy device 1250 toward the first end 1254, such that the collection channel 1272 has a first height $H_3$ at the second opening 1274 that decreases for a length $L_2$ in the direction from the second end 1256 toward the first end 1254 to a second height $H_4$. In various embodiments, the first height $H_3$ is from about 10 µm to about 5 mm, such as a height of about 10 µm, about 50 µm, about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, or about 5 mm and the second height $H_4$ is from about 5 µm to about 2 mm, such as about 5 µm, about 10 µm, about 50 µm, about 100 µm, about 200 µm, about 300 µm, about 400 µm, about 500 µm, about 600 µm, about 700 µm, about 800 µm, about 900 µm, about 1 mm, or about 2 mm. The length $L_2$ can be a length of from about 100 µm to about 20 mm, such as a length of about 100 µm, about 500 µm, about 1 mm, about 2 mm, about 3 mm, about 4 mm, about 5 mm, about 6 mm, about 7 mm, about 8 mm, about 9 mm, about 10 mm, about 15 mm, or about 20 mm.

Figure 16A:
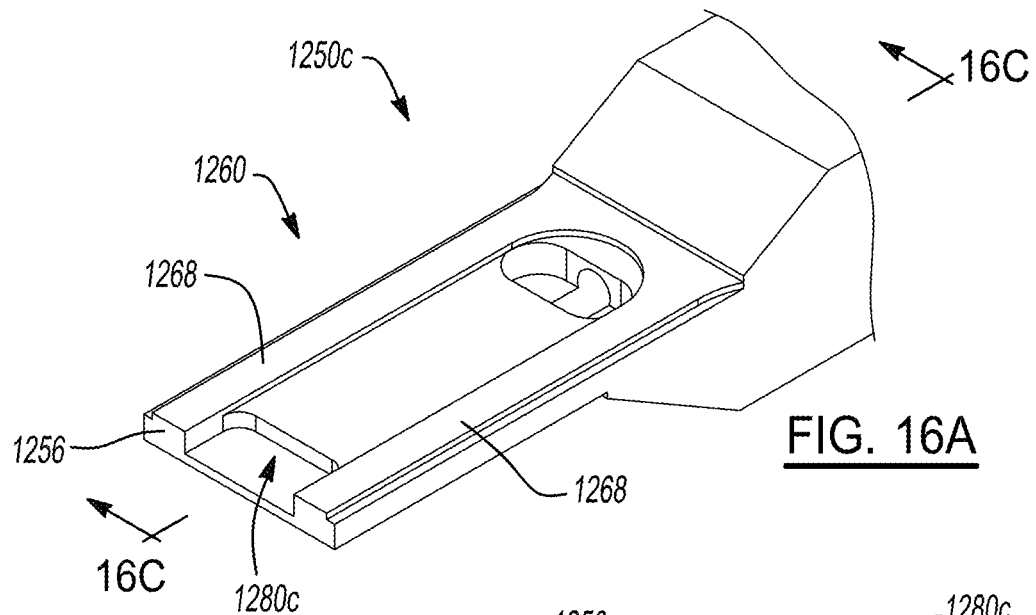
FIG. 16A is an illustration of a biopsy device according to certain aspects of the current technology.
Figure 16B:
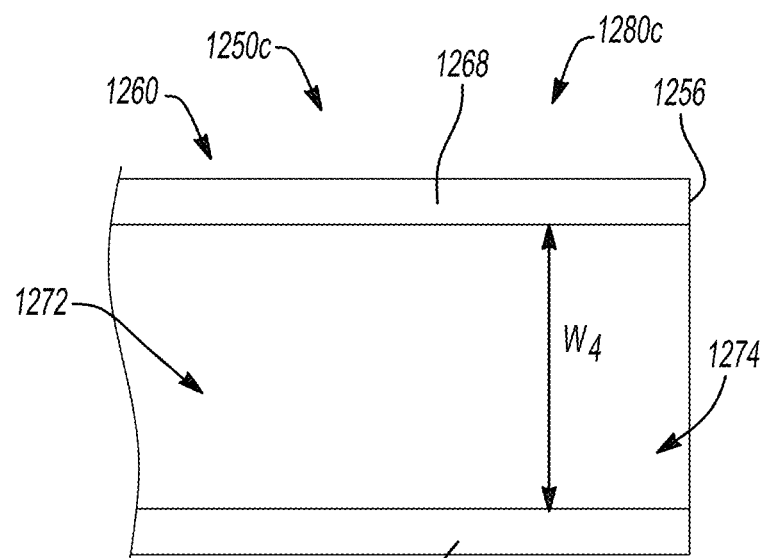
FIG. 16B is a cross-sectional top view of the biopsy device of FIG. 16A.
Figure 16C:
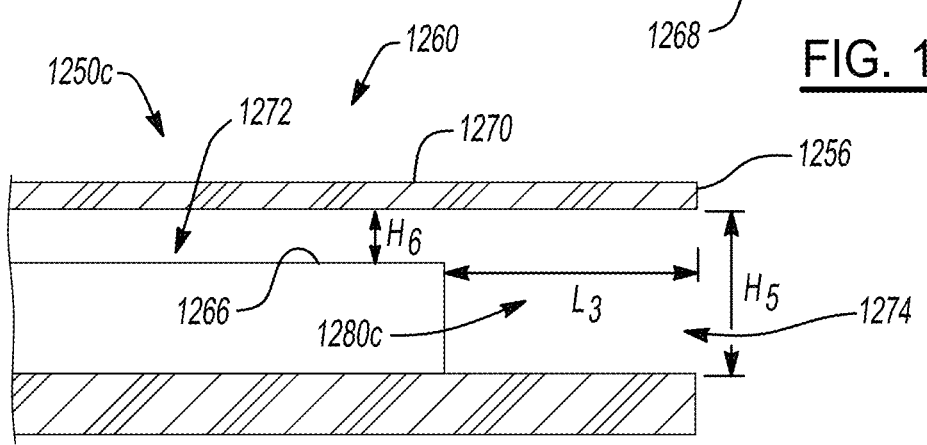
FIG. 16C is a cross-sectional side view of the biopsy device of FIG. 16A taken along line 16C.

FIGS. 16A-16C show a biopsy device 1250c that is similar to the biopsy device 250 of FIGS. 14A-14G. However, the biopsy device 1250c has a sample introduction section 1280c that differs from the sample-introduction section 1280. As shown in FIG. 16B, the walls 1268 are substantially straight, such that the collection channel 1272 has a single width W4 of from about 100 µm to about 10 mm, such as a width of about 100 µm, about 500 µm, about 1 mm, about 2 mm, about 3 mm, about 4 mm, about 5 mm, about 6 mm, about 7 mm, about 8 mm, about 9 mm, or about 10 mm. As shown in FIG. 16C, the collection channel 1272 has a height $H_5$ from the second opening 1274 that extends toward the first end 1254 for a length $L_3$. After the length $L_3$, the height of the collection channel 1272 abruptly decreases to a height $H_6$. In various embodiments, the height $H_5$ is from about 10 µm to about 5 mm, such as a height of about 10 µm, about 50 µm, about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, or about 5 mm and the second height $H_6$ is from about 5 µm to about 2 mm, such as about 5 µm, about 10 µm, about 50 µm, about 100 µm, about 200 µm, about 300 µm, about 400 µm, about 500 µm, about 600 µm, about 700 µm, about 800 µm, about 900 µm, about 1 mm, or about 2 mm. The length $L_3$ can be a length of from about 100 µm to about 20 mm, such as a length of about 100 µm, about 500 µm, about 1 mm, about 2 mm, about 3 mm, about 4 mm, about 5 mm, about 6 mm, about 7 mm, about 8 mm, about 9 mm, about 10 mm, about 15 mm, or about 20 mm.

Figure 17A:
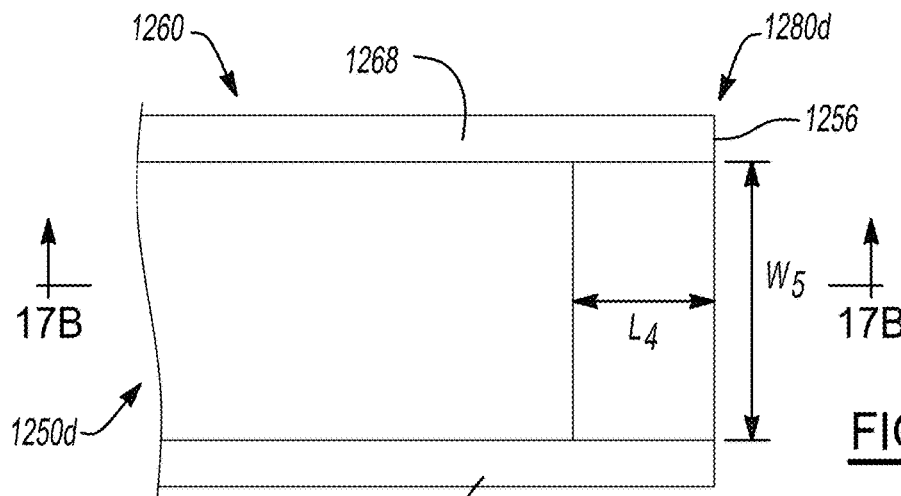
FIG. 17A is a sectional top view of a sample introduction section of a section of a biopsy device according to certain aspects of the current technology.
Figure 17B:
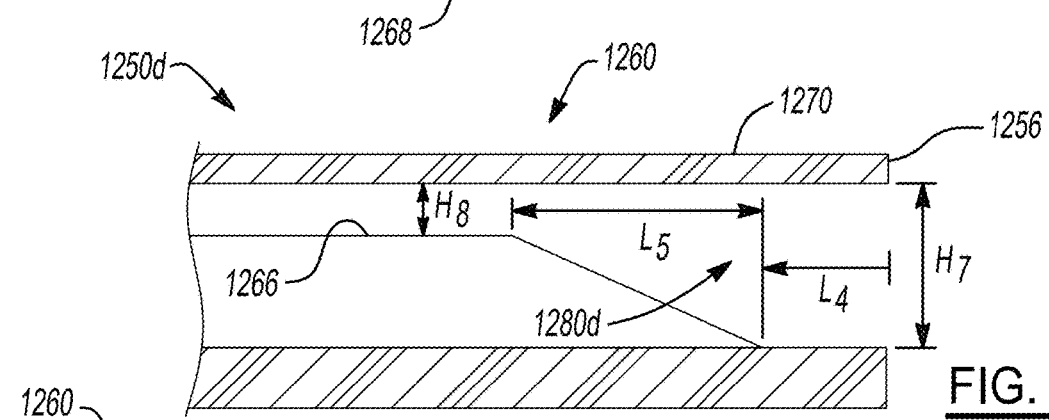
FIG. 17B is a cross-sectional side view of the sample introduction section of FIG. 17A taken along line 17B.

It is understood that the geometries of the foregoing sample introduction sections are not limiting. FIGS. 17A-17B and 18A-18B show additional non-limiting examples of sample introduction sections. In particular, FIGS. 17A-17B show a sample introduction section 1280d from a biopsy device 1250d. As shown in FIG. 17A, the walls 1268 are substantially straight, such that the collection channel 1272 has a single width W5 of from about 100 µm to about 10 mm, such as a width of about 100 µm, about 500 µm, about 1 mm, about 2 mm, about 3 mm, about 4 mm, about 5 mm, about 6 mm, about 7 mm, about 8 mm, about 9 mm, or about 10 mm. As shown in FIG. 17B, the collection channel 1272 has a height $H_7$ from the second opening that extends toward the second end for a length $L_4$. After the length $L_4$, the surface 1266 slopes toward the second surface 1270 to a height $H_8$ over a length $L_5$. In various embodiments, the height $H_7$ is from about 10 µm to about 5 mm, such as a height of about 10 µm, about 50 µm, about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, or about 5 mm and the height $H_8$ is from about 5 µm to about 2 mm, such as about 5 µm, about 10 µm, about 50 µm, about 100 µm, about 200 µm, about 300 µm, about 400 µm, about 500 µm, about 600 µm, about 700 µm, about 800 µm, about 900 µm, about 1 mm, or about 2 mm. The lengths $L_4$ and $L_5$ can independently be lengths of from about 100 µm to about 20 mm, such as lengths of about 100 µm, about 500 µm, about 1 mm, about 2 mm, about 3 mm, about 4 mm, about 5 mm, about 6 mm, about 7 mm, about 8 mm, about 9 mm, about 10 mm, about 15 mm, or about 20 mm.

Figure 18A:
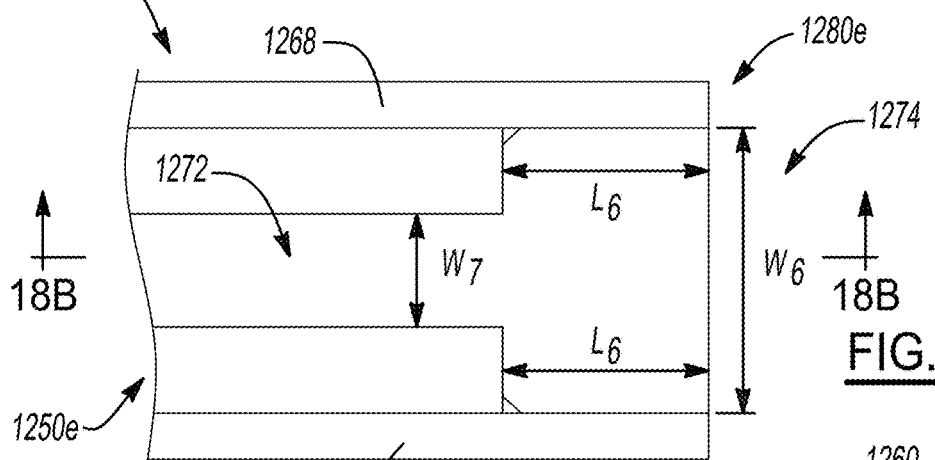
FIG. 18A is a sectional top view of a sample introduction section of a section of a biopsy device according to certain aspects of the current technology.
Figure 18B:
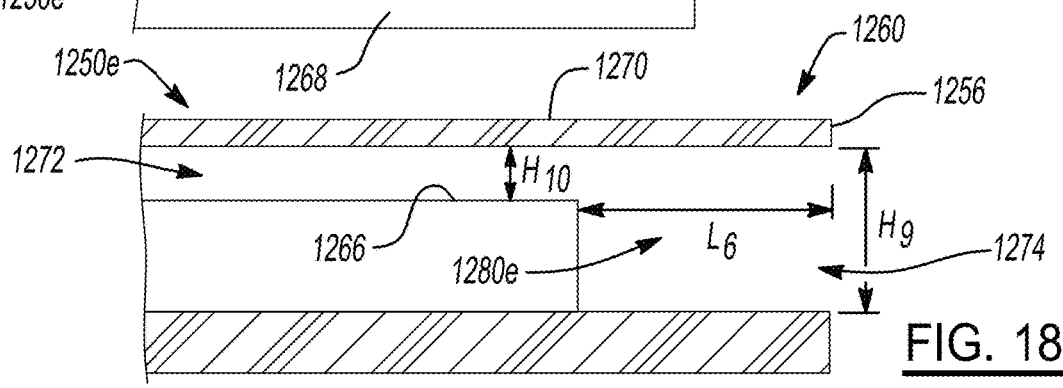
FIG. 18B is a cross-sectional side view of the sample introduction section of FIG. 18A taken along line 18B.

FIGS. 18A-18B show a sample introduction section 1280e from a biopsy device 1250e. As shown in FIG. 18A, the walls 1268 are substantially straight for a length $L_6$ extending from the second opening 1274 toward the first end 1254. Throughout the length $L_6$, the collection channel 1272 has a first width $W_6$. After the length $L_6$, the walls 1268 jut inward to define a second width $W_7$. In various embodiments, the first width $W_6$ is from about 100 µm to about 10 mm, such as a width of about 100 µm, about 500 µm, about 1 mm, about 2 mm, about 3 mm, about 4 mm, about 5 mm, about 6 mm, about 7 mm, about 8 mm, about 9 mm, or about 10 mm and the second width $W_7$ is from about 50 µm to about 8 mm, such as about 50 µm, about 100 µm, about 250 µm, about 500 mm, about 750 µm, about 1 mm, about 2 mm, about 3 mm, about 4 mm, about 5 mm, about 6 mm, about 7 mm, or about 8 mm. The length $L_6$ can be a length of from about 100 µm to about 20 mm, such as a length of about 100 µm, about 500 µm, about 1 mm, about 2 mm, about 3 mm, about 4 mm, about 5 mm, about 6 mm, about 7 mm, about 8 mm, about 9 mm, about 10 mm, about 15 mm, or about 20 mm. As shown in FIG. 18B, the collection channel 1272 has a height $H_9$ from the second opening 1274 that extends toward the first end 1254 for a length $L_6$. After the length $L_6$, the height of the collection channel 1272 abruptly decreases to a height $H_{10}$. In various embodiments, the height $H_9$ is from about 10 µm to about 5 mm, such as a height of about 10 µm, about 50 µm, about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, or about 5 mm and the height $H_{10}$ is from about 5 µm to about 2 mm, such as about 5 µm, about 10 µm, about 50 µm, about 100 µm, about 200 µm, about 300 µm, about 400 µm, about 500 µm, about 600 µm, about 700 µm, about 800 µm, about 900 µm, about 1 mm, or about 2 mm.

One possible challenge when using the biopsy devices 1250-1250e is that optics in a corresponding imaging system can be contaminated by biological fluids or tissues (e.g., by blood), thus resulting in a degradation of image quality. This degradation of image quality can be avoided by cleaning the biopsy device 1250-1250e prior to insertion into an imaging device. Alternatively the biopsy device 1250-1250e can be configured to be inserted into an outer carrier vial that provides a physical separation between the second opening 1274 and the external environment, but which includes an optically transparent region that enables imaging of aspirated tissue inside the biopsy device 1250-1250e.

Figure 19A:
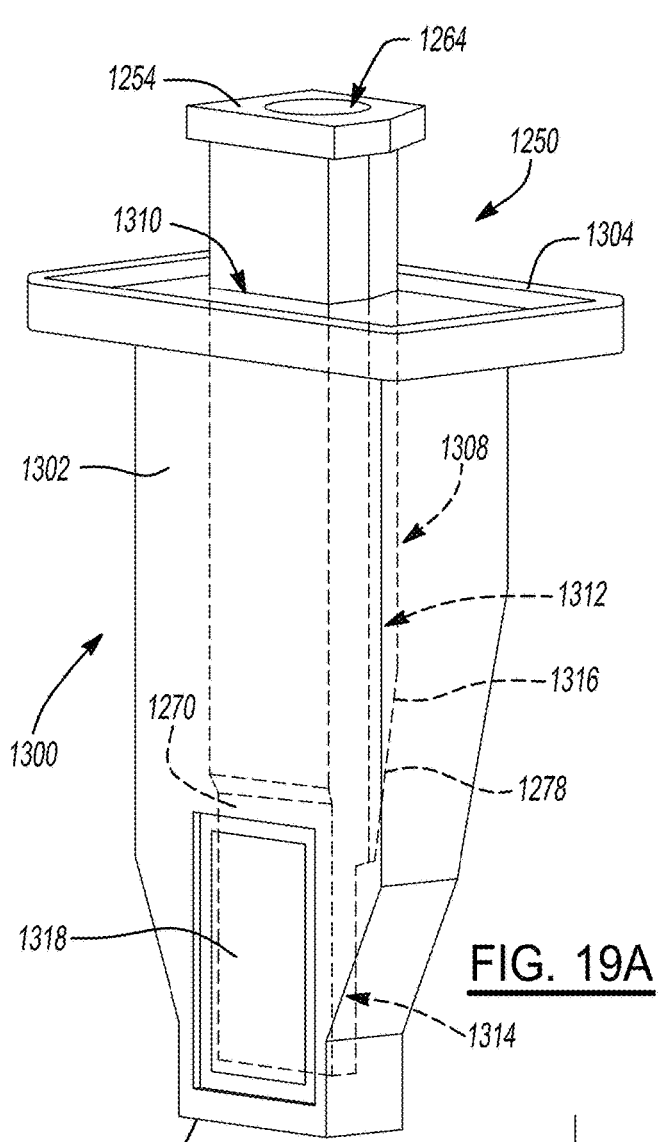
FIG. 19A is an illustration of a biopsy device inserted into an outer carrier vial according to certain aspects of the current technology.
Figure 19B:
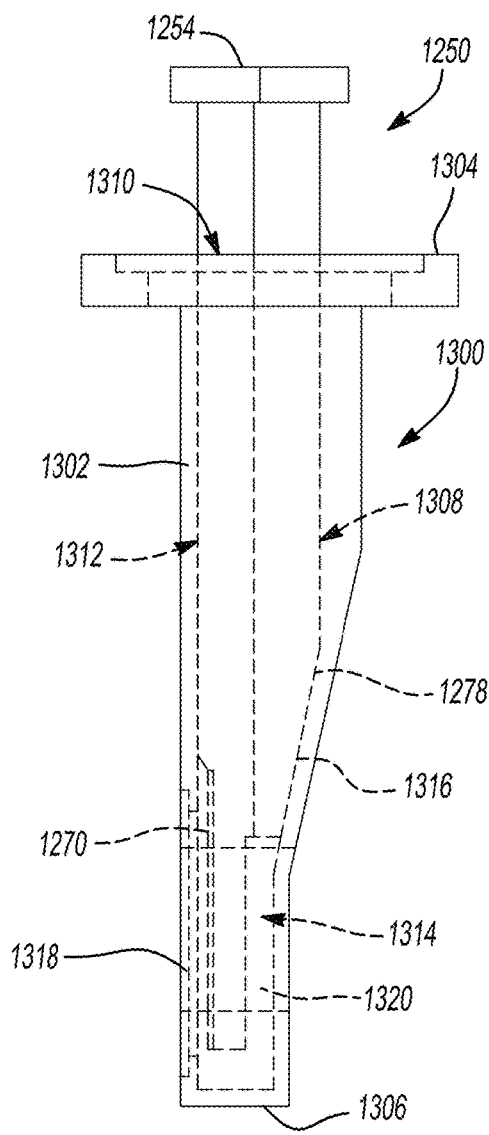
FIG. 19B is a perspective side view of the biopsy device inserted into an outer carrier vial of FIG. 19A.

Such an outer carrier vial 1300 is shown in FIGS. 19A and 19B with the biopsy device 1250 of FIGS. 16A-16G inserted therein. Nonetheless, it is understood that any of the biopsy devices described herein may be accommodated by the outer carrier vial 1300 or corresponding embodiment thereof. The outer carrier vial 1300 is optionally machinable or may be fabricated by molding polymeric materials, for example. The outer carrier vial 1300 comprises an elongate body 1302 that extends from a first end 1304 to a second opposing end 1306. The elongate body 1302 defines a hollow interior compartment 1308 that extends from an opening 1310 at the first end 1304 toward the second end 1306, but which does not extend through the second end 1306 to define a second opening.

The hollow interior compartment 1308 includes a fitting section 1312 and an imaging section 1314. Whereas the biopsy device 1250 includes a positioning surface 1278, the fitting section 1312 includes an opposing position surface 1316. The imaging section 1314 includes a detection window 1318 that is at least partially optically transparent. In various embodiments, the imaging section has more than enough space to accommodate at least a portion of the sample collecting portion 1260 of the biopsy device 1250, such that a space 1320 is defined about the sample collecting portion 1260. Therefore, prior to insertion, the outer carrier vial 1300 may be at least partially filled with water or oil for imaging, such that after the biopsy device 1250 is inserted into the hollow interior compartment 1308 of the outer carrier vial 1300, the water or oil fills the space 1320. Although the water or oil, i.e., immersion fluid, may be contaminated by a biological sample, imaging and/or detecting devices remain clean.

When the biopsy device 1250 is inserted into the hollow interior compartment 1308 of the outer carrier vial 1300, the positioning surface 1278 of the biopsy device 1250 engages the opposing positioning surface 1316 of the fitting section 1312. When the positioning surface 1278 is engaged with the opposing positioning surface 1316, the detection window 1318 of the outer carrier vial is aligned with the at least partially optically transparent second surface 1270 of the biopsy device 1250. Accordingly, for the purpose of imaging or detecting, light from a detection or imaging device may pass through the detection window 1318 of the outer carrier vial 1310, through the at least partially transparent second surface 1270 of the biopsy device 1250, and interact with a biological sample disposed within the collection channel 1272. The space 1320 about the sample collecting portion 1260 of the biopsy device 1250 may be filled with an immersion fluid. Additionally or alternatively, immersion fluid may be disposed on the detection window 1318 of the outer carrier vial 1310 so that the biological sample can be analyzed and/or imaged.

In various embodiments, a biopsy device, such as a biopsy device configured as a biopsy tip according to the current technology, is disposable, sterilely packaged, and configured to be removably coupled to a standard surgical suction device. In this manner, the biopsy tip is replaceable. Accordingly, the present technology provides kits comprising at least one sterilized and individually or collectively packaged biopsy devices. In various embodiments, the kit contains biopsy devices each with collection channels having the same dimensions in the collections channels and optically transparent regions. In other embodiments, the kit contains biopsy devices with a variety of collection channel sizes and/or optically transparent regions. The biopsy devices in the kit are configured to be removably coupled to a surgical suction device, remove a sample of tissue from a patient, and be directly analyzed in an imaging device to provide compositional and/or structural and optionally navigational information about the sample tissue. Moreover, some kits contain biopsy devices with optically transparent portions that are active in a Raman spectral range and/or biopsy devices with optically transparent portions that are non-active in a Raman spectral range, wherein the Raman spectral range is described above. Accordingly, the kit can contain any variation of biopsy device provided by the current technology, wherein the biopsy devices in the kit are all the same or different. The kit may also include at least one outer carrier vial to utilize in conjunction with the biopsy tips for imaging purposes as described above. The kit may also include a container of immersion fluid and/or a unique label.

In other embodiments, the biopsy tip is sterilizeable and reusable. In yet other embodiments, the biopsy tip includes a regulator for controlling the negative pressure that is transmitted by the biopsy tip.

Imaging Systems

Any of the biopsy devices described herein can be used in conjunction with an ex vivo imaging system.

Figure 20:
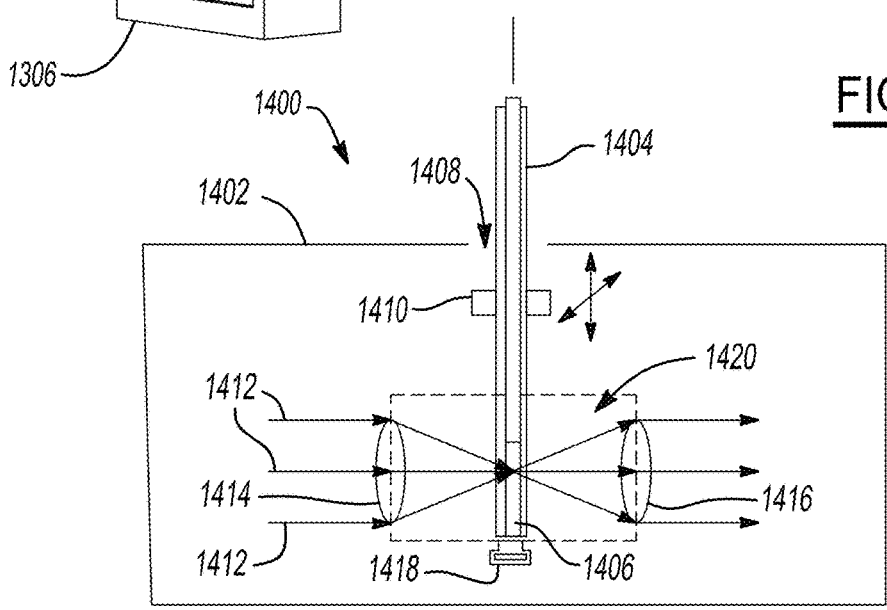
FIG. 20 is an illustration of a system for analyzing a biopsy sample.

FIG. 20 shows a system 1400 comprising an ex vivo imager 1402 and a biopsy device 1404, such as any of the biopsy devices described above. One end of the biopsy device 1404 contains a tissue sample 1406. The end is inserted into an opening or slot 1408 of the imaging device 1402. In various embodiments, and as shown in FIG. 20, the biopsy device 104 is clamped in place with a one-, two-, or three-dimensional stage 1410 to allow for focusing and or large-area scan imaging. Stage motor drivers can be configured to be synchronized with other control elements, such as wavelength tuning, imaging and start and stop triggers. Excitation light 1412 is focused onto the sample 1406 though the portion of at least partially transparent wall of the biopsy device 1404 using excitation focusing optics 1414, such as an objective lens. Signal from the sample 1406 can either be collected in transmission using emission optics 1416, such as a condenser, or collected in reflection using the excitation focusing optics 1414. The system 1400 may further include a switch or button 1418 that automatically starts the acquisition when activated by an inserted biopsy device 1404. The switch or button 416 may be a mechanical or light-based switch or button. The imager 1402 may further include a sealed cavity 1420 that allows for an immersion fluid (e.g., water). In some embodiments, the system 1400 includes a fluid exchange system for the immersion fluid. In yet other embodiments, the system 1400 may further include means for washing, cleaning, and/or wiping an outside surface of the biopsy device 1404 (e.g., from blood), such as to keep the immersion fluid and imaging optics clean. In some embodiments, the means for washing is be a brush positioned at the opening 1408 where the biopsy device 1404 is inserted. In another embodiment, the means for washing is a separate cleaning chamber, which may include ultra-sonic cleaners. In yet another embodiment, the means for washing is a cloth or tissue that is used to manually wipe a surface of the biopsy device 1404. The combined use of the biopsy device 1404 together with the imager 1402 eliminates any sample processing steps and allows seamless integration of optical imaging (e.g., with SRS or CARS) into a clinical workflow.

Users, such as medical practitioners, view images developed by the current technology on a graphical user interface (GUI). In practice, image acquisition is triggered by inserting an end of a biopsy device containing a biological sample into an imager or by the user. Algorithms may automatically perform autofocus, multi-color tiling, field flattening, color channel overlapping, stitching, and H&E pseudo-coloring procedures. In some embodiments, the GUI may only serves as a display with zoom, pan, and image rotate functions (i.e., it could run on a tablet device). An SRS signal derived from the material of the imaging tip can serve as a guide signal for autofocus, i.e., be sample independent, as well as for field flatness correction and intrinsic spectral calibration.

In another example, the ex vivo imager may include a plurality of openings or slots for loading multiple biopsy devices. A medical practitioner could load the biopsy devices each containing a biological sample, e.g., in a pre-defined order, as they are taken from a patient. The imager then automatically loads each sample, individually and consecutively, and images them individually and consecutively. In another embodiment, the biopsy device is configured to allow loading of multiple biological samples in a biopsy device, e.g., by loading multiple biological samples in a single biopsy device one after the other or by having multiple biopsy devices that can be loaded separately. The ex vivo imager is then configured to image multiple biopsy samples automatically.

In yet another example, the ex vivo imager may be configured to read a label printed on the biopsy device. As non-limiting examples, such labels can be bar-codes, QR codes, numbers (e.g., "1," "2," etc.), letters (e.g., "A", "B," etc.), unique serial numbers, or a combination thereof (e.g., "Biopsy 1," "Biopsy 2," etc.). In one embodiment this label reading can be implemented by including a bar-code scanner or QR code scanner that can read a bar-code or QR code on the biopsy device when the biopsy device is loaded in a first position in the imager and can image the sample when the biopsy device is loaded in a second position in the imager. In another embodiment label reading can be implemented by including a white light chamber in the imager that can read a label on the biopsy device when loaded in a first position and can image a sample when the biopsy device is loaded in a second position. In yet another embodiment the imaging optics of the ex vivo imager can be configured to image a label, QR code or bar-code (e.g., by transmission or reflection imaging). One advantage of including a unique label on the biopsy device is that it can allow for keeping track of multiple biopsies. For example, the label can be added to the image meta-data to provide identification by the same instrument or other instruments (e.g., surgical navigation system) when datasets are archived or merged.

In another embodiment, an imaging system can be configured to image tissue samples contained in a biopsy device as described above and be also configured to provided regular white-light imaging of the tissue sample. For example, the tissue sample for white-light imaging can be tissue sections or touch/squash preparations stained with H&E or intra-vital dyes. This dual functionality provides extended usability. The white-light imaging can be implemented by the same image formation mechanism (e.g., beam-scanned imaging) or by two separate mechanisms (e.g., beam-scanned imaging for imaging the biopsy device and camera-based imaging for the white-light imaging). In another embodiment an imaging system can be configured to include a white-light camera for macroscopic imaging of the tissue sample and a second imaging system for microscopic imaging of the tissue sample. For example, the macroscopic imaging system can then be used to determine an outline of the tissue sample and thus determine the scan area for the microscopic imaging by means of image registration between these two modalities. This procedure allows for scanning the perimeter of a tissue sample at high-resolution.

In another embodiment, the above-described biopsy devices and an imaging systems can be used as an integrated device. The common principle is that the tissue is aspirated into the sample collection portion of the device using a source of negative pressure. Such a combined device can either be used in situ by proving the optical imaging with a miniaturized imager or ex vivo by using a traditional biopsy instrument to remove the tissue sample from the patient and then loading it into the imager using negative pressure.

FIGS. 21 and 22 show examples of a combined imager and biopsy device, referred to herein as "combination devices." In particular, FIG. 21 shows a first combination device 1450 and FIG. 22 shows a second combination device 1452. Both the first combination device 1450 and second combination device 1452 are capable of transmission imaging. The combination devices 1450, 1452 commonly comprise a body 1454 that defines a collection channel 1456 that extends from a first opening 1458 at a first end 1460 of the body 1454 to a second opening 1462 at an opposing second end 1464 of the body 1454. Whereas the collection channel 1456 of the first combination device 1450 includes an angled turn, e.g., about 90°, near the second end 1464, the collection channel 1456 of the second combination device 1452 is substantially straight. Both combination devices 1250, 1452 include a lens 1468 and a detector 1470 integrated into the body 1454. When a biological sample 1472 is aspirated into the collection channel 1456 of the first combination device 1450 by way of negative pressure 1480, a scanning mechanism 1474 emits light 1476 through the lens 1468, which focuses the light through biological sample 1472 and substantially straight through to the detector 1470. When a biological sample 1472 is aspirated into the collection channel 1456 of the second combination device 1452 by way of negative pressure 1480, a scanning mechanism 1474 emits light 1476 through the lens 1468, which reflects and focuses the light through the biological sample 1472 and to the detector 1470. In both combination devices 1450, 1452 the detector 1470 is positioned in transmission of the sample. However, it is understood that the combination devices 1450, 1452 are exemplary and that additional configurations may be adapted. For example, the collection channel 1456 could be configured to provide both forward looking optics and aspiration or a signal could be collected in reflection. These examples show the use of a miniaturized GRIN lens for imaging, but other optics may be used. The examples also show the use of a fiber scanner as a mechanism to provided imaging but other mechanisms such as galvano or MEMS scan mirrors can also be used.

The combination devices 1450, 1452 can be used in situ to provide histological information to a user, and after this histological information has been obtained, the biological sample 1472 may be recovered and used for an ex vivo analysis, such as a genetic analysis. Put another way, at least two tests may be performed on a biological sample obtained by the combination devices 1450, 1452.

Combining Microscope and Macroscopic Imaging Data

A common challenge in either in vivo or ex vivo imaging is that imaging information is on a microscopic scale compared to features that can be identified by eye. There is a need for presenting both microscopic and macroscopic data in a useful fashion. Examples of macroscopic imaging modalities are bare eyes, surgical microscopes, ultra-sound system, MRI or CT. With the present technology, it is possible to quickly acquire multiple images a the tissue cavity. Therefore, there is need for technology for keeping track from where images where taken. The present technology addresses these needs.

Figure 23:
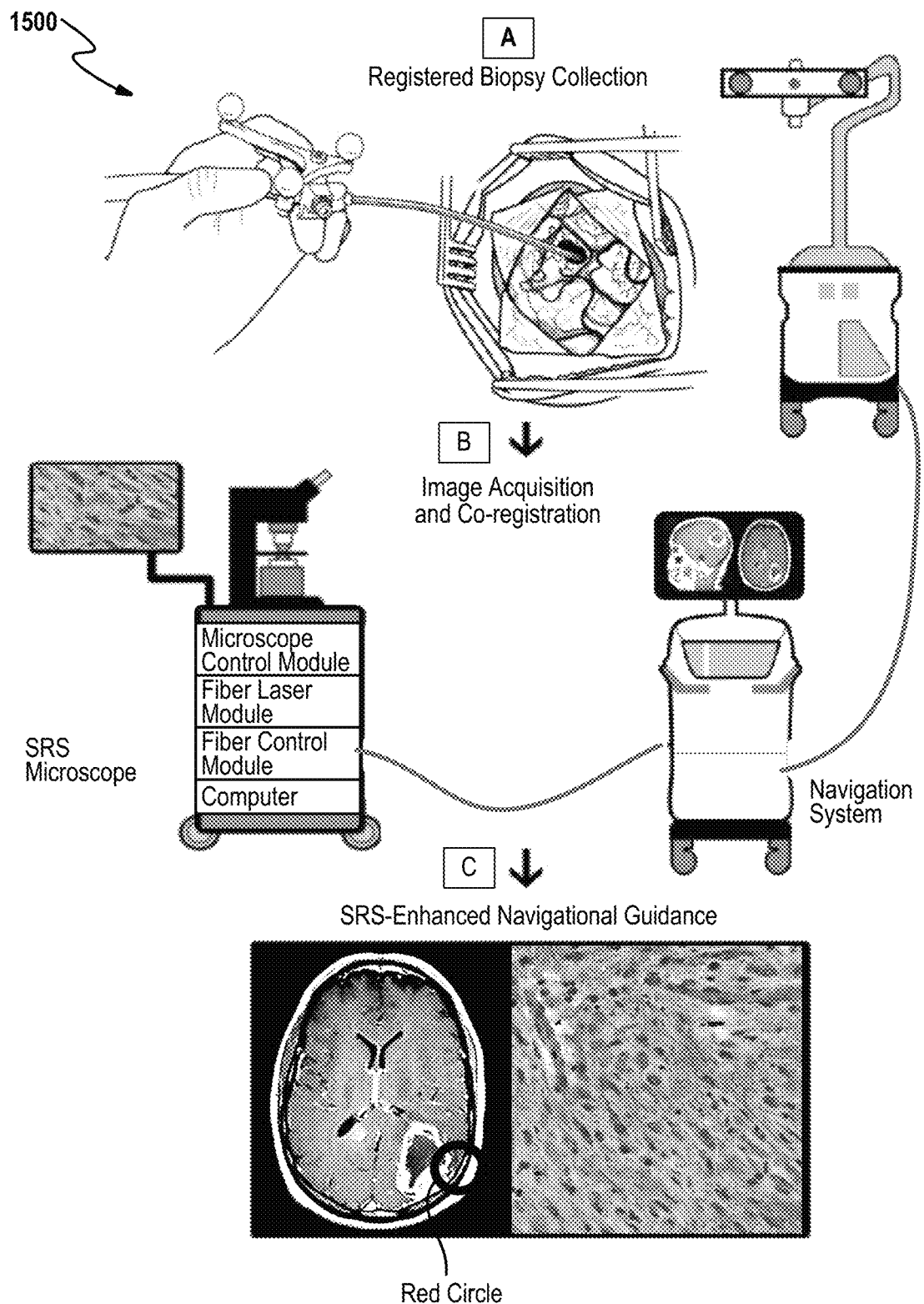
FIG. 23 shows an exemplary workflow for the use of a biopsy device and imager according to the present technology.

FIG. 23 shows an example of a clinical workflow 1500 for the use of a biopsy device and an ex vivo imager according to certain variations described herein. It comprises the steps of: (A) registered biopsy collection, (B) image acquisition and co-registration, and (C) SRS-enhanced navigational guidance. Samples are collected with instruments that are trackable by the navigation system and positional coordinates at the biopsy site (red circle) are recorded. An excised tissue sample is imaged via an ex vivo imager and co-registered into the MRI/CT-based navigational dataset. Finally, a merged dataset with MRI and SRS information can be used to navigate within an operative field based on both structural data based on MRI and histologic data based on microscopic imaging. For example, multiple biopsies could be displayed in the context of the same MRI/CT-based navigation dataset. This workflow allows a surgeon or other medical practitioner to go back to the same position where the tissue was collected and continue resection if needed.

Figure 24:
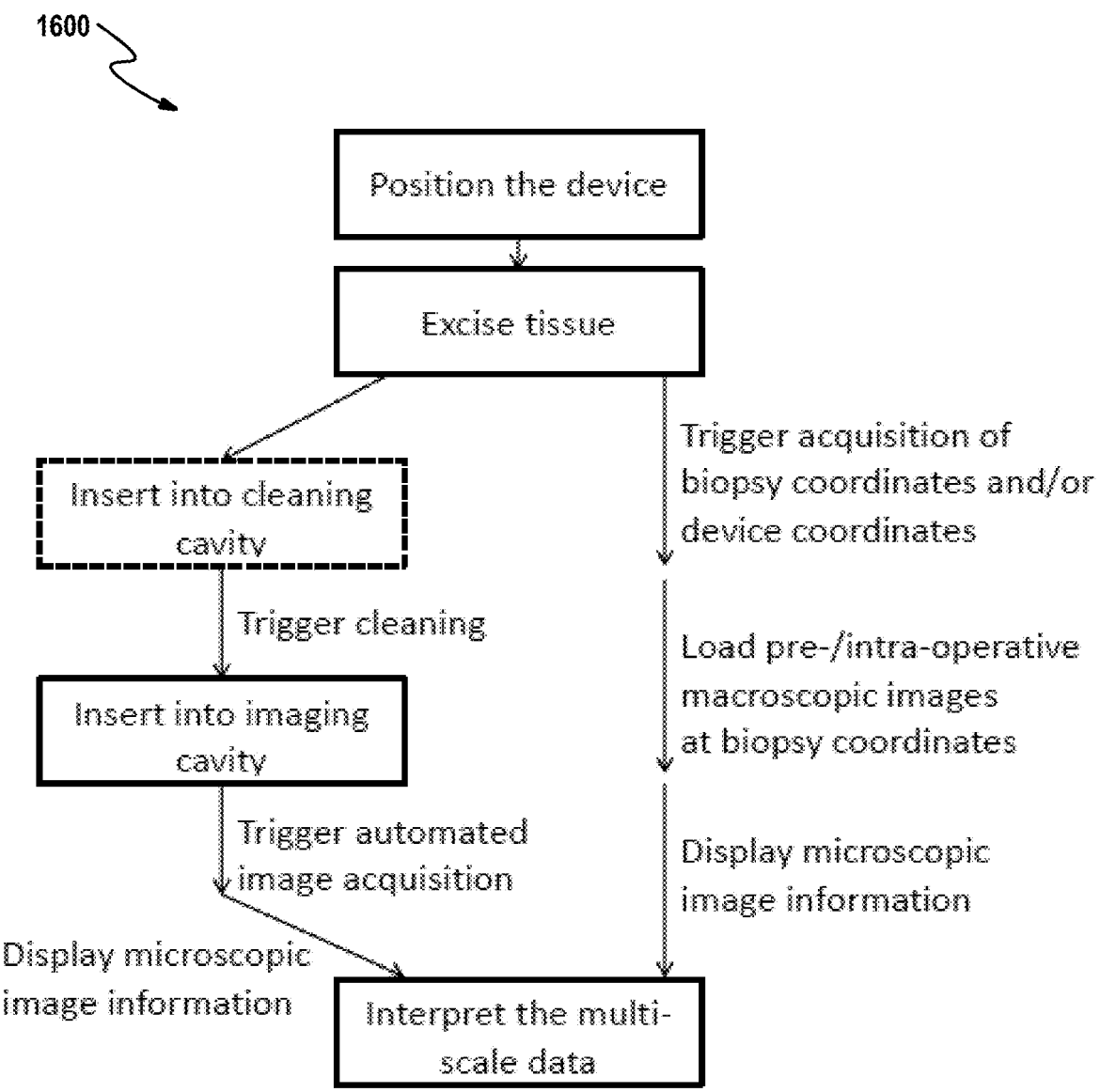
FIG. 24 is a block diagram showing an exemplary workflow using ex vivo real-time histology.

FIG. 24 shows a block diagram of an exemplary workflow 1600 using ex vivo real-time histology. A medical practitioner positions a tracked biopsy device over an area of interests. Excising the tissue (e.g., by suction, compression, or cutting) triggers acquisition of the coordinates at which the tissue was taken. This process can either be automatic (e.g., triggered by a switch inside biopsy device or by conformational changes of the tracking markers that can be recognized by the navigational system) or be performed manually by the practitioner (e.g., by a foot paddle). The system 1600 may then load and display pre-operative macroscopic images at the biopsy coordinates. In the meantime the biopsy device containing the tissue sample may be washed, e.g., of blood, etc., and is then inserted into an imaging cavity, which triggers the acquisition of microscopic image data. Once complete, the microscopic image data is displayed side by side with macroscopic image data. The microscopic image data will remain saved inside the macroscopic data set and additional biopsies will be added as they are acquired.

Figure 25:
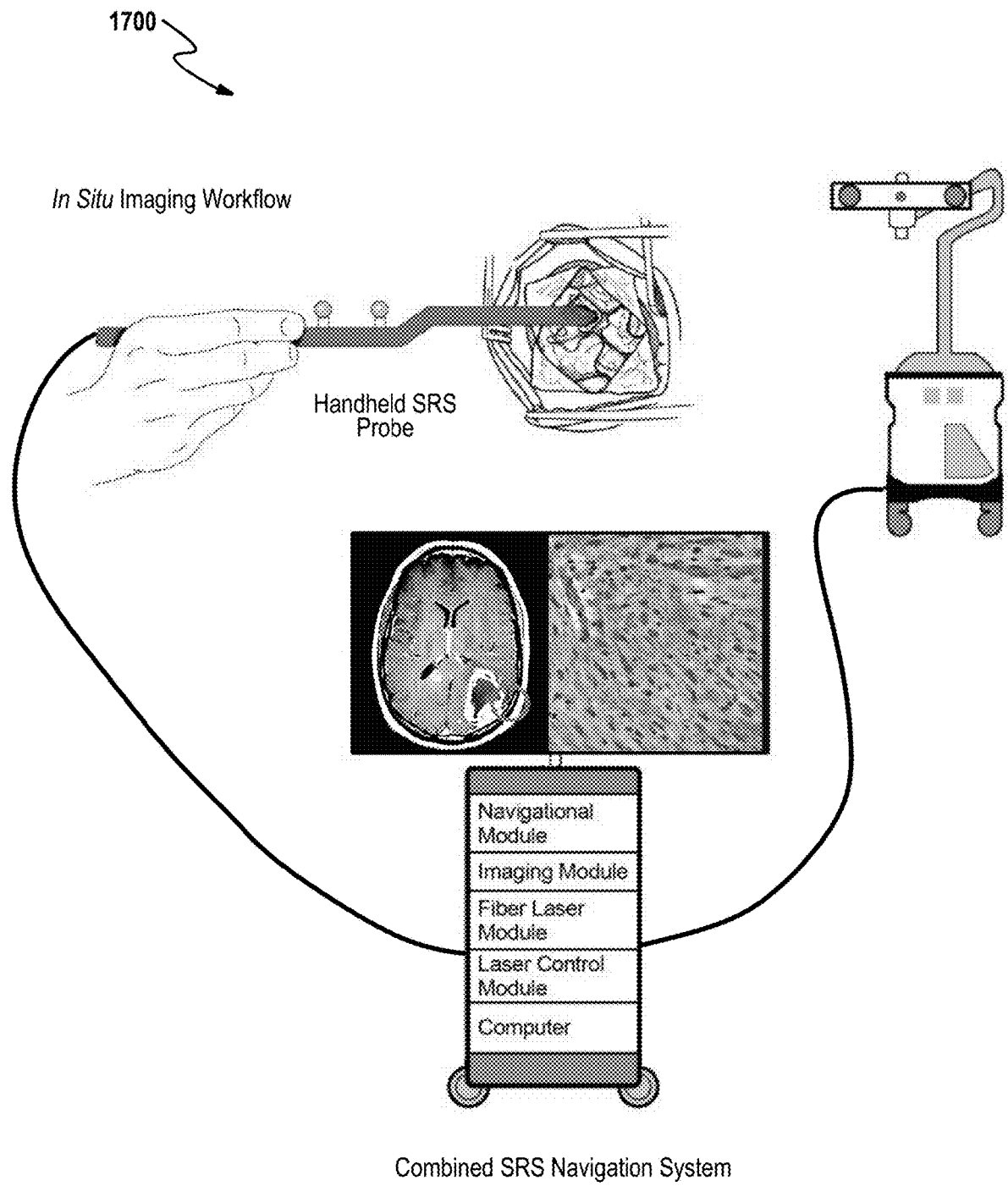
FIG. 25 shows an exemplary clinical workflow for in vivo real-time histology that enables navigation based on magnetic resonance imaging (MRI) and stimulated Raman scattering (SRS) data simultaneously.

FIG. 25 shows an exemplary clinical workflow 1700 for in vivo real-time histology that enables navigation based on MRI and SRS data simultaneously. A handheld probe, tracked by a navigation system, collects histologic images, which are co-registered to an MRI-based navigational dataset in real time. A merged dataset with MRI and SRS information can be used to navigate within an operative field based on both structural data based on MRI and histologic data based on SRS imaging. The handheld probe is used to scan a cavity in regions where tumor infiltration is suspected to ensure that densely infiltrated tissue is removed and non-infiltrated regions are preserved.

In certain variations, a handheld SRS probe is registered to a navigational system, typically used in glioma surgery. SRS images, along with their coordinates in the registered stereotactic space, are automatically stored during acquisition. At the conclusion of scanning, the navigational system is capable of displaying both histologic information of the nearest-acquired SRS image along with the position in a navigational model. The surgeon could then identify regions in the cavity having residual tumor and determine if additional resection can be safely carried out.

Figure 26A:
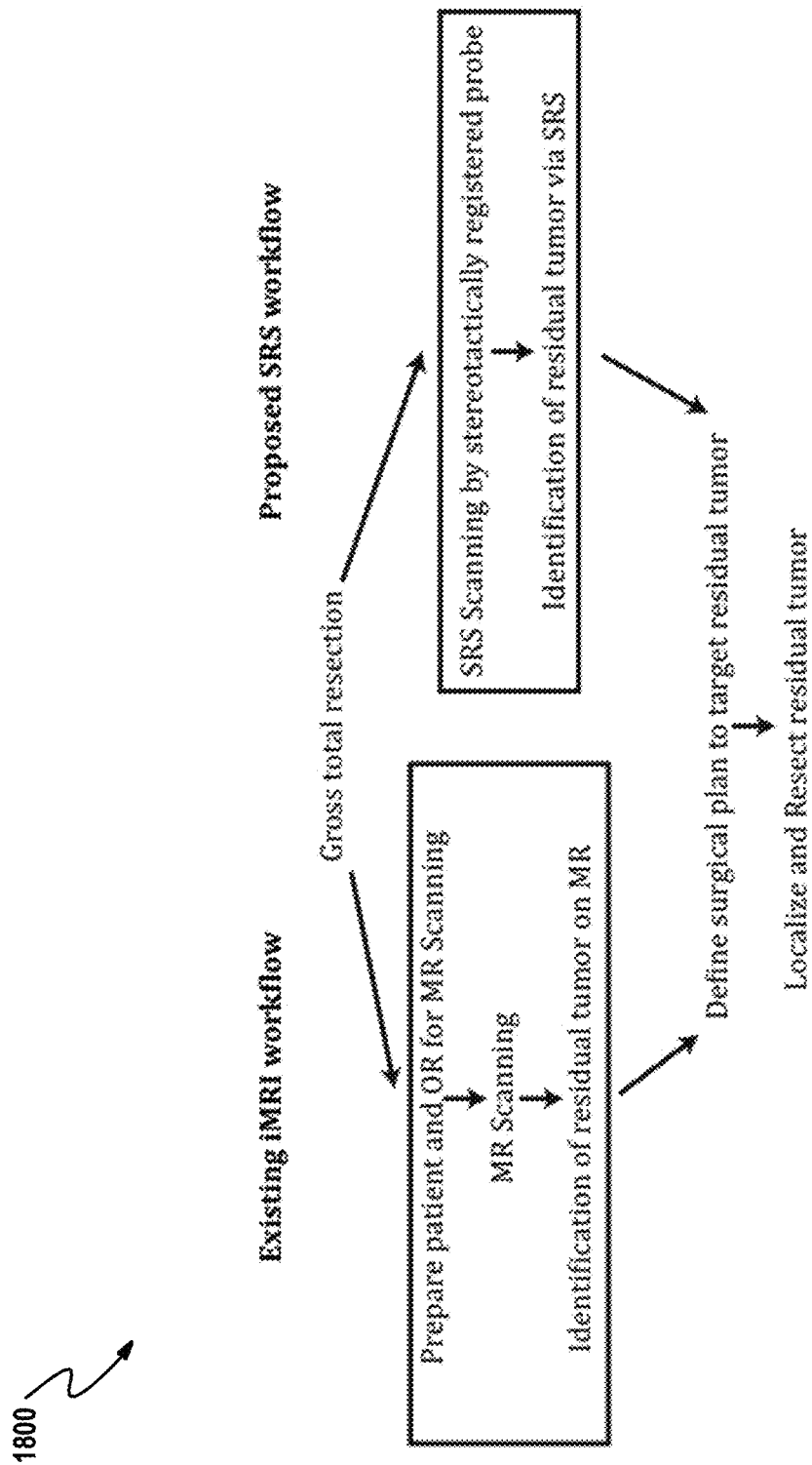
FIG. 26A is a diagram showing a comparison of intraoperative magnetic resonance imaging (MRI) and stimulated Raman scattering (SRS) workflows.
Figure 26B:
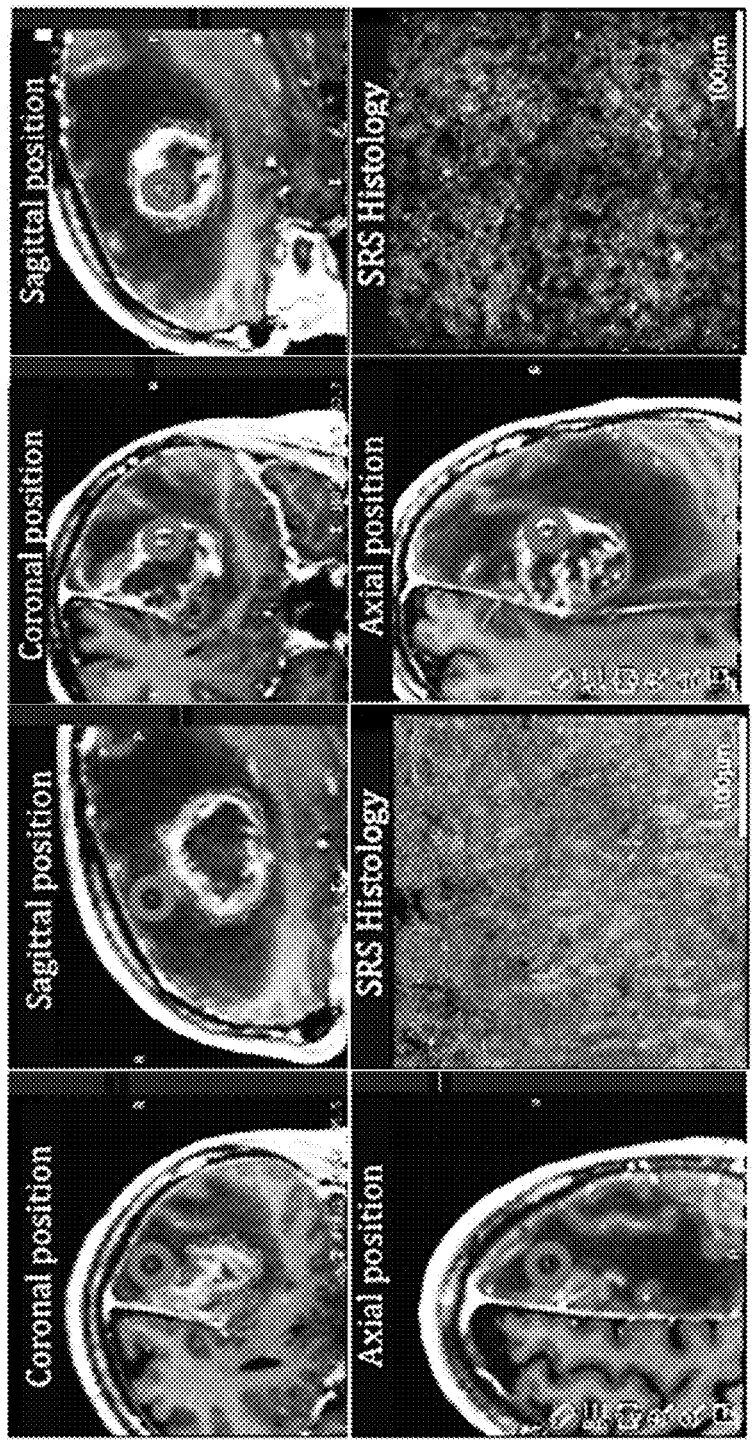
FIG. 26B shows examples of navigational and SRS data merging.
Figure 26C:
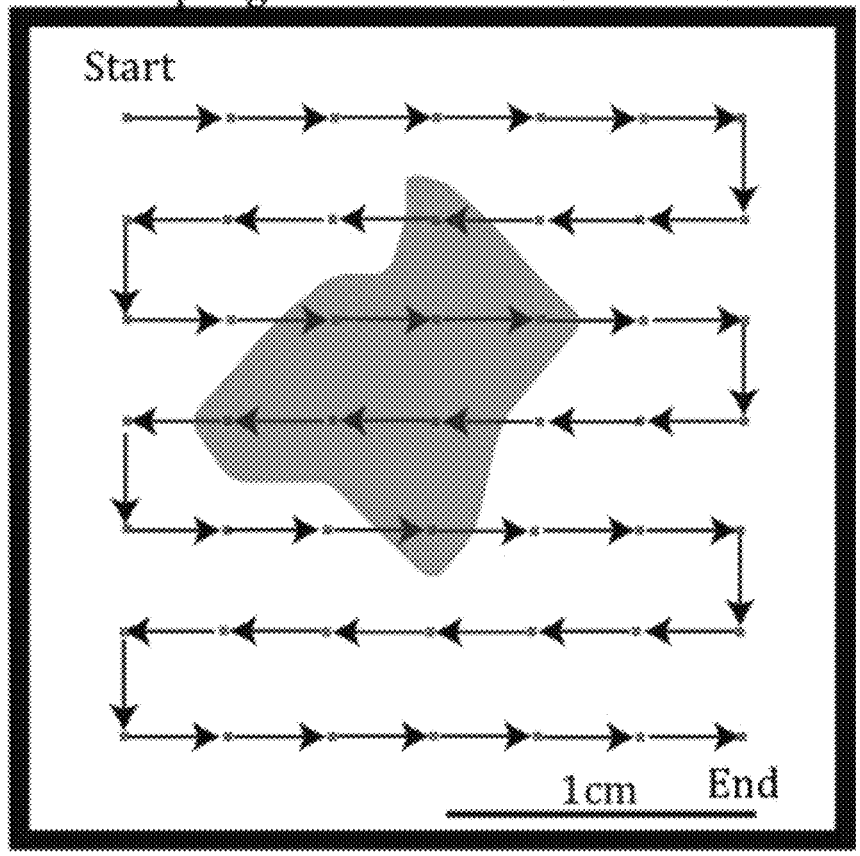
FIG. 26C shows a scan pattern for taking multiple biopsies.

SRS histology requires high magnification to resolve diagnostic cell- and tissue-level features and correspondingly has a limited field of view (FOV=350 μm in the case of preliminary results). With a handheld SRS endoscope, image acquisition and registration is carried out by scanning a cavity surface at 3 mm intervals. A 2×2 cm² resection cavity can be scanned in 2.5 minutes (assuming 50 images at 3 s per FOV including 0.5 s for image acquisition and 2.5 s for re-positioning). This time is substantially shorter than the additional time required for iMRI acquisition (on average 1.6 h), even if multiple 2×2 cm² surfaces are scanned to detect tumors over larger regions. The 3-mm spacing is based on the approach used to sample lumpectomy specimens, which are similar in size to brain tumors. This method has been demonstrated to reduce re-surgery rate from 26% to 9%. 3 mm is also about the precision of manual placement of a probe. FIG. 26A shows another exemplary a workflow 1800 for SRS imaging in glioma surgery. More specifically, FIG. 26B shows a comparison of intraoperative MRI and SRS workflows. Both workflows rely on gross total resection, image acquisition, and a frameless stereotactic navigational system to register and localize residual tumors. The main difference is that SRS eliminates the task of preparing the patient and operative environment for image acquisition. FIG. 26B shows examples of navigational and SRS data merging. Once SRS and positional data are collected with an SRS endoscope, a surgeon can navigate into any position in the surgical cavity to observe the local histologic pattern. Histologic data at a given position is based on data collected from the nearest FOV. The data is displayed on the navigational monitor along with the positional information in three orthogonal views traditionally used for navigation. FIG. 26C shows a scan pattern for taking multiple biopsies drawn to scale. A 2 cm×2 cm tumor cavity can be mapped with 360 µm FOV at 3-mm intervals in about 2.5 min. Mapped onto this pattern is a hypothetical scanning dataset where green boxes indicate FOVs that are tumor free, while red boxes indicate FOVs where there is evidence of tumor infiltration. The pink region is a simulated region at high risk for residual tumor given the concentration of "red" FOV's.

For both ex vivo and in vivo scenarios, it is often advantageous to further track the orientation of a biopsy or imaging device such as to maintain an orientation of the microscopic images with the macroscopic images. For example this may be useful to delineation tumor margins or the orientation of nerve fibers that are only visible based on the microscopic imaging. Identifying white matter fiber tract orientation often has functional significance. Key fiber tracts, such as, for example, corticospinal tracts, the arcuate fasciculus, the superior and inferior longitudinal fasciculi and optic pathways, can be identified based on their orientation. These fiber tracts are crucial for normal functioning of a nervous system and there it is advantageous to a patient if they can be preserved during surgery. Accordingly, in various embodiments, imaging methods include tracking and recording coordinates and/or the orientation of the biopsy device to provide recorded coordinates and/or orientation information corresponding to a location and/or orientation of a biological sample as it was collected, and displaying pre-operative and/or intra-operative macroscopic imaging data at the recorded coordinates and/or orientation. In various embodiments, microscopic images are displayed in the context of macroscopic images at the recorded coordinates and/or orientation in which they were acquired. In some embodiments, the biopsy device is removably coupled to a surgical suction device and positioned at a known distance and orientation from navigational beacons positioned on the surgical suction device. A surgical navigational system calculates the orientation and position of the biopsy device relative the navigational beacons. In another embodiment, at least one navigational beacon is positioned in the biopsy device for communication with a navigational system. In yet another embodiment, both a surgical suction device removably coupled to the biopsy device and the biopsy device both has navigational beacons positioned thereto for communication with a navigational system.

Automated Image Segmentation of SRS Images

Figure 27:
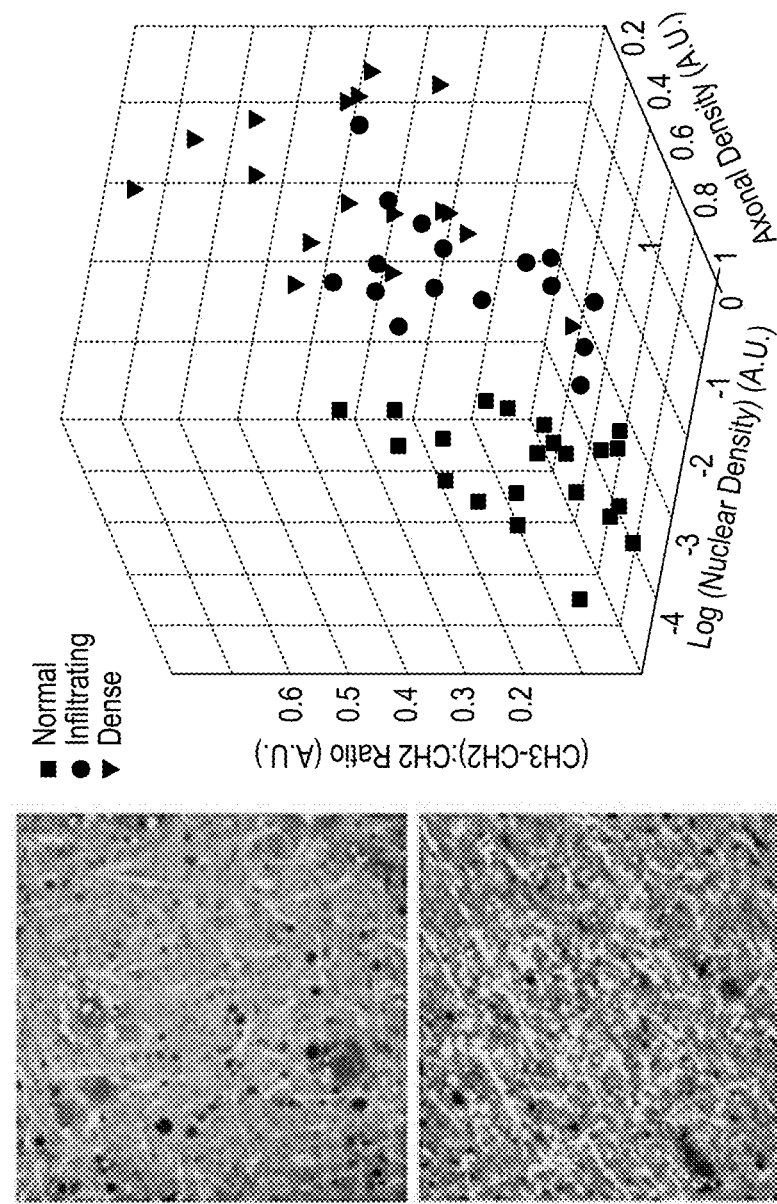
FIG. 27 shows a classification of stimulated Raman scattering (SRS) images to assess a degree of tumor infiltration.

Interpretation of histopathologic findings has a subjective component, may be time-intensive, and may require the expertise of a pathologist. Imaging data may be incorporated into an operative workflow with automated means of detecting tumor infiltration. A classification scheme might integrate robust, quantified SRS image attributes (hypercellularity, axonal density, protein:lipid ratio) into a single metric for detecting infiltration. FIG. 27 shows a classification of SRS images to assess a degree of tumor infiltration. The figure shows a three-dimensional scatter plot of quantified nuclear density, axonal density, and protein:lipid ratio in SRS images. Measurements are taken from 1477 300×300 µm$^2$. FOVs from 51 fresh tissue biopsies from 18 patients (3 epilepsy patients, 15 brain and spine tumors encompassing 8 distinct histologic subtypes). Each point on the scatterplot represents the average value of each biopsy. Biopsies were classified as predominantly normal to minimally hypercellular (n=21), infiltrating tumor (n=14), or high-density tumor (n=16) by a board-certified neuropathologist based on H&E staining. Marker color indicates the mean classifier value for each biopsy, with 0 (most likely normal) depicted in cyan (squares) and 1 (most likely tumor) depicted in red (circles and triangles). Representative FOVs from normal cortex, normal white matter, low-grade glioma, and high-grade glioma are shown.

Figure 28A:
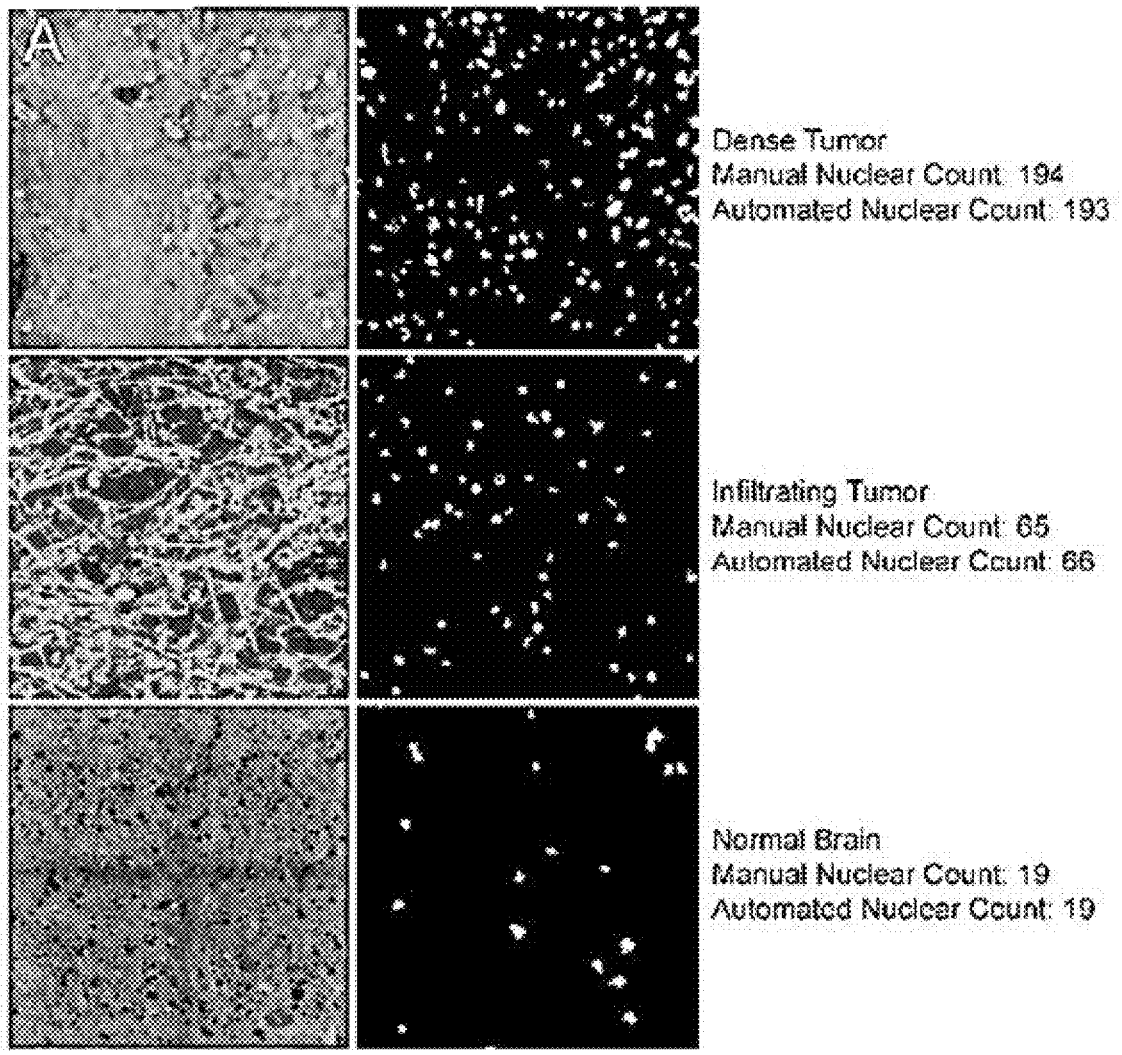
FIG. 28A shows segmentation of stimulated Raman scattering (SRS) microscopy field of views (FOVs) of nuclei detected in dense tumor (top), infiltrating tumor (middle), and normal tissue.

A program capable of automatically quantifying the number of nuclei, axonal density and protein:lipid ratio in each FOV can be used (FIG. 28A). The automated cell-counting and axonal quantification program correlated well with manual methods for distinguishing normal brain from, infiltrating and dense glioma, though some discrepancies in cell counts occurred where nuclear contrast was faint or obscured. Image quantification methods were verified by evaluating adjacent FOVs at key transitions in specimens: the gray-white junction (FIG. 29) and margins of an oligodendroglioma. The cellularity and protein:lipid ratios decreased with an accompanying increase in axonal density moving from cortex into white matter. A similar pattern existed moving from within a tumor into adjacent brain, but the difference in cellularity was approximately an order of magnitude greater.

Figure 28B:
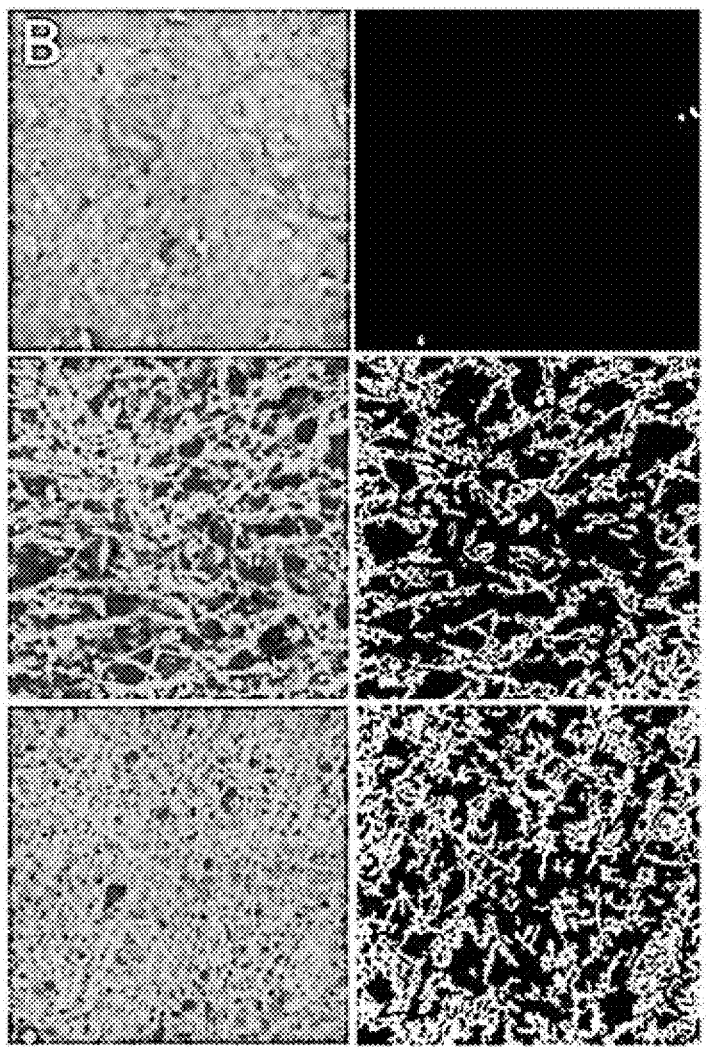
FIG. 28B shows segmentation of SRS FOVs of axons detected in dense tumor (top), infiltrating tumor (middle), and normal tissue.
Figure 28C:
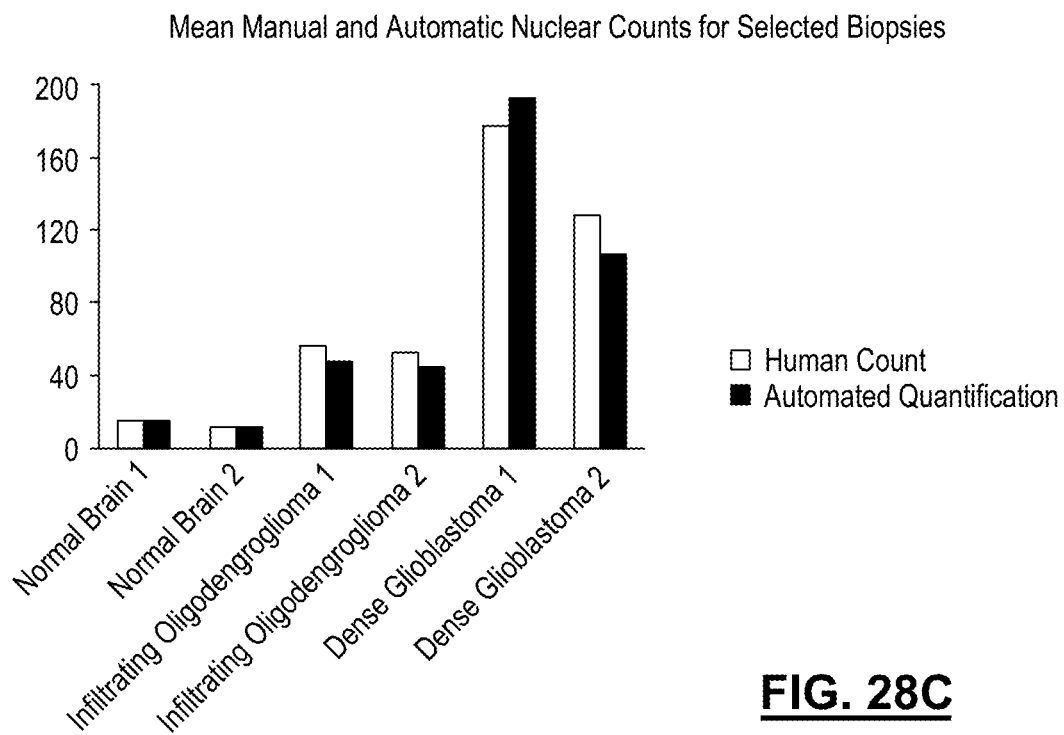
FIG. 28C is a graph showing the mean number of nuclei per FOV detected manually and by image segmentation.
Figure 28D:
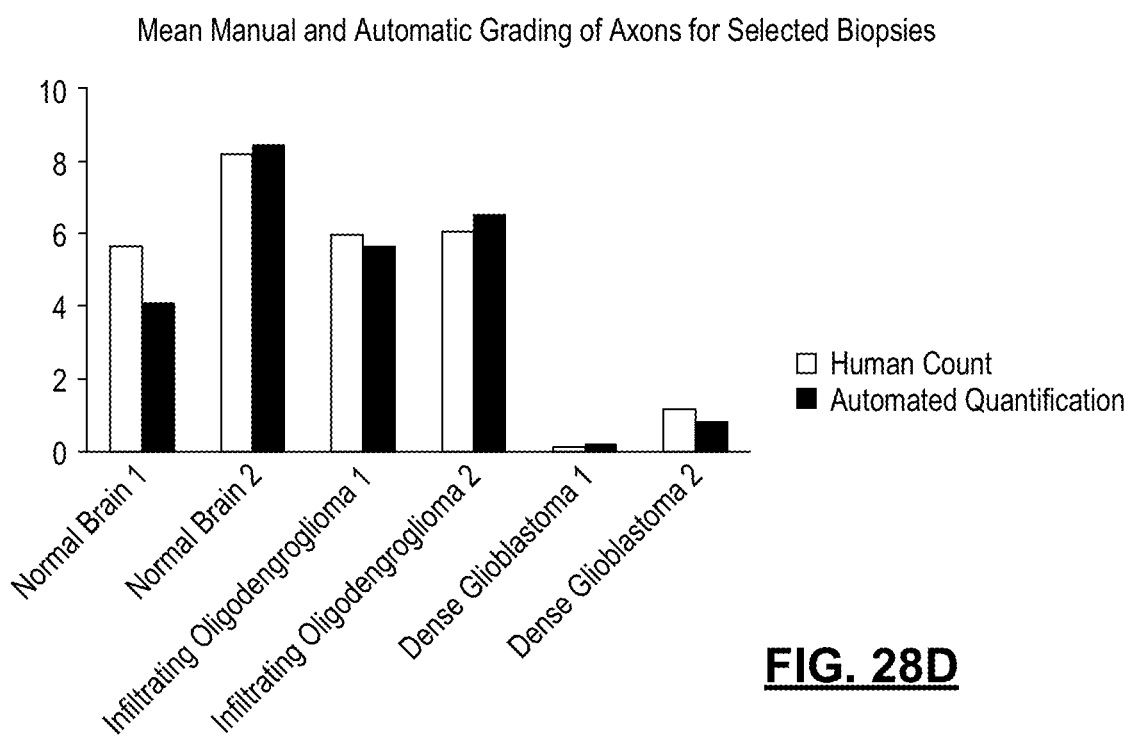
FIG. 28D is a graph showing axonal density rated manually and by image segmentation.
Figure 29A:
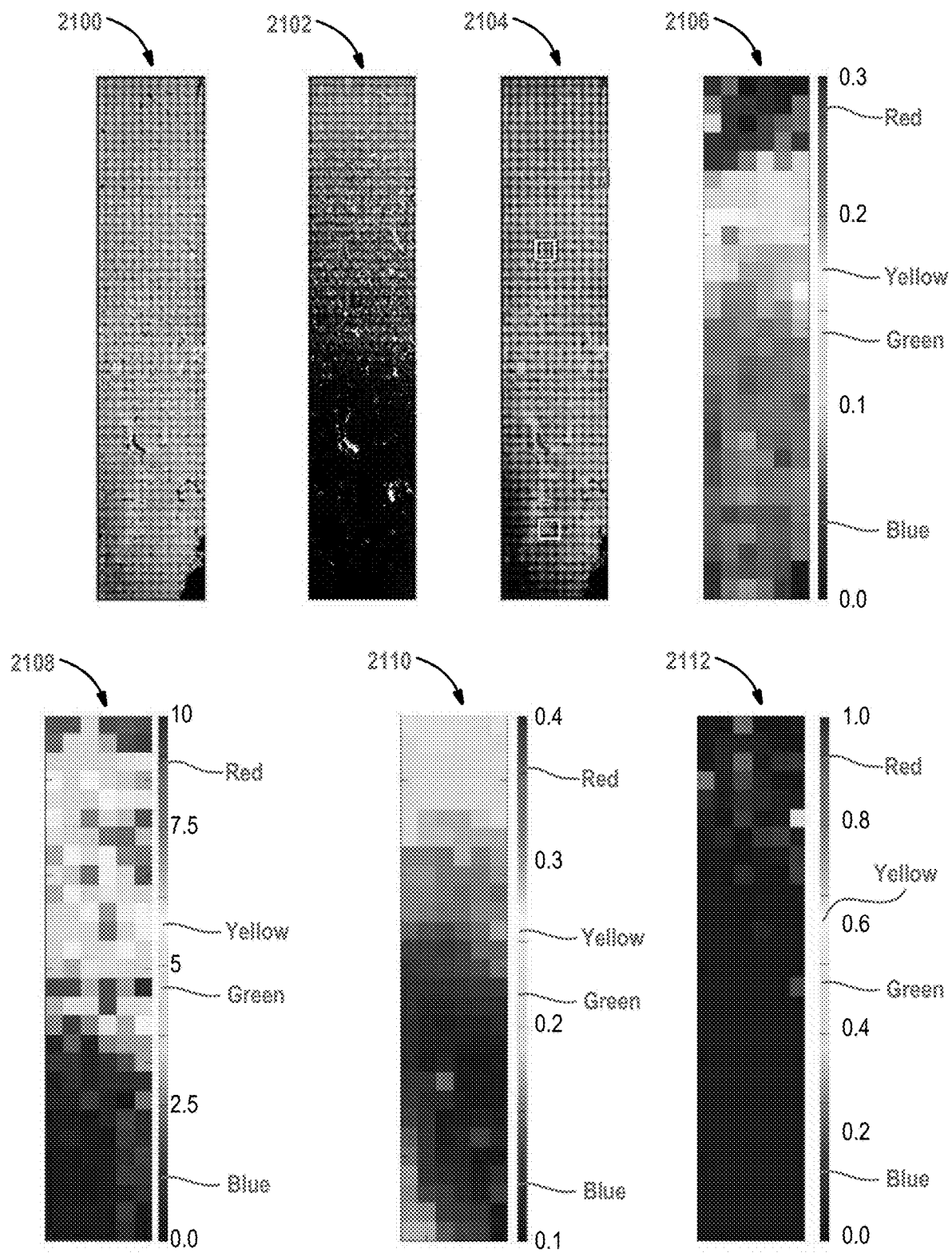
FIG. 29A shows a quantitative analysis of a normal tissue sample imaged with stimulated Raman scattering (SRS) microscopy.

FIGS. 28A-28D show a validation of SRS image segmentation. FIG. 28A shows segmentation of SRS microscopy FOVs (left) showing nuclei detected (right) in dense tumor (top), infiltrating tumor (middle), and normal tissue (bottom). The number of nuclei detected is compared to a manual count of the same FOV. FIG. 28B shows segmentation of SRS FOV images (left) showing axons detected (right) in dense tumor (top), infiltrating tumor (middle), and normal tissue (bottom). Axon perimeter length is re-normalized to a 10-point scale based on a full SRS image library and compared to a manual rating on a 10-point scale (0=no axons, 10=maximum axonal density). FIG. 28C shows mean number of nuclei per FOV detected by manual count and by image segmentation for representative normal brain (n=2), infiltrating tumor (n=2), and dense tumor (n=2) biopsies. FIG. 28D shows axonal density of FOVs manually rated and segmented as above for representative normal brain (n=2), infiltrating tumor (n=2), and dense tumor (n=2) biopsies FIG. 29 shows a quantitative analysis of a normal tissue sample imaged with SRS microscopy. The images show, SRS microscopy lipid channel 2100, SRS microscopy protein channel 2102, overlay of SRS microscopy lipid and protein images 2104, heat map of calculated axon densities (arbitrary units) for all FOVs 2106, heat map of nuclei per FOV 2108, heat map of calculated protein:lipid ratio for all FOVs 2110, and classifier values for all FOVs 2112. Insets show FOVs with high (red), average (yellow), and low (blue) classifier values. Note that while the mean classifier value is greater in cortex (top of biopsy), all FOVs have classifier values well below a cutoff of 0.5.

Cellularity, axonal density, and protein:lipid ratio of 1477 300×300 µm² FOVs from 51 fresh tissue biopsies from 18 patients (3 epilepsy patients, 15 brain and spine tumors encompassing 8 distinct histologic subtypes) are quantified and plotted. Three-dimensional plots of averaged values for each of the 51 biopsies (FIG. 27) revealed the variability in each attribute among the tissues analyzed. A plot of each of the 1477 FOV revealed a gradient of the parameters distinguishing normal from densely tumor-infiltrated tissue.

Individual tissue attributes had varying degrees of sensitivity and specificity to indicate tumor infiltration. However, to create a robust classifier for predicting tumor infiltration incorporating each tissue attribute, a quasi-likelihood approach with a generalized additive model (GAM) is used. The classifier was built from 1477 FOVs derived from three patients with temporal lobe epilepsy and 15 brain tumor patients. Half of the FOVs (n=738) were used to create the classifier, which was then tested on the other half (n=739). Classifier values ranged from 0 to 1, where 0 carried the lowest probability of tumor infiltration and 1 carried the highest probability of infiltration. The classifier distinguished between tumor-infiltrated and non-tumor-infiltrated brain with a mean sensitivity of 97.5% and specificity 98.5% (AUC 0.995). The classifier also distinguishes between categories of tumor infiltration (normal to minimal hypercellularity, infiltrating glioma, dense glioma) with a high degree of accuracy regardless of grade or histologic subtype. The classifier was in close agreement to pathologists' determination of tumor infiltration.

The classifier was created from an array of tumors encountered in and near the central nervous system so that it could be broadly generalizable. However, because glial tumors are more infiltrative and have less distinct margins than non-glial tumors, discriminating glial tumor infiltration from non-infiltrated brain poses the greatest challenge. Therefore, a separate quasi-likelihood GAM, including only glial tumors and controls, is created. The glioma-only GAM distinguishes between tumor-infiltrated and non-infiltrated brain with 97.0% sensitivity and 98.7% specificity.

Although a quasi-likelihood GAM classifier accounts for within-subject correlation and training sets are not included in building the classifier, it is still possible that some of the testing set data are correlated with some of the training set data (e.g., they come from the same subject). To break this dependence, we used a leave-one-out cross-validation approach on the dataset consisting of exclusively glial tumors (and epilepsy patients as controls). Though not as accurate as the quasi-likelihood GAM, the leave-one-out cross-validation approach yields 87.3% sensitivity and 87.5% specificity.

Data are taken from multiple FOVs from individual biopsies. Thus, the data are correlated and standard statistical models that assume the data are independent do not apply. Quasi-likelihoods methods, however, include a dispersion parameter that accounts for over- or under-dispersion in the data caused by correlation within subjects and, thus, are valid statistical methods for clustered data (e.g., FOVs within individuals). A dispersion parameter greater than 1 indicates over-dispersion and less than 1 indicates under-dispersion. A quasi-likelihood approach to build classifiers is adopted; in particular, a quasi-binomial approach. In the classifiers, covariates enter the quasi-likelihood using a GAM approach as opposed to entering linearly. This allows more flexibility in modeling a decision boundary between groups. In the quasi-likelihood GAM method, the covariates enter as cubic spline functions. The covariates of interest are axonal density, nuclear density, protein:lipid ratio, and all two-way interactions between these covariates.

Four separate quasi-likelihood GAM classifiers are built: 1) normal vs. infiltrating plus dense tumor, 2) normal vs. infiltrating tumor, and 3) normal vs. dense tumor. Stepwise regression is used to determine the best fit to each of the three cases. Two-way interactions are taken prior to fitting the GAM with a cubic spline function. Stepwise regression selects the following covariates for each of the models: 1) the three main effects and the two-way interactions between axonal and nuclear densities and axonal density and the protein:lipid ratio, 2) the three main effects and all three two-way interactions, 3) the three main effects and the interaction between axonal and nuclear densities, and 4) the three main effects and the interactions between axonal and nuclear densities and between nuclear densities and the protein:lipid ratio.

Given the model determined by stepwise regression, the data was split randomly into two equal parts, creating a training set and a testing set. The quasi-likelihood GAM is refit to the training set and predictions are obtained from the testing set. Receiver operating characteristic curves, sensitivity, specificity, and accuracy are obtained using a discriminant probability threshold of 0.5 on the predictions made from the testing set. The above analysis is performed 1000 times and reported the average and 95% confidence interval of these statistics over the 1000 runs.

To eliminate any possible correlation of data within the quasi-likelihood approach, a cross-validation approach described by Picard et al. was utilized. In this approach, a subject is left out of the training set. After the model is fitted to the training data, the left-out subject's data are predicted using the model. The above four analyses are run using the cross validation approach each time leaving out a different subject. The leave-one-out cross validation is performed on the dataset that excluded patients with non-glial tumors.

SRS microscopy images are segmented and analyzed using custom software developed in the MATLAB Image Processing Toolbox (The MathWorks, Inc., Novi, Mich.). The segmentation program has three modules. The first module imports and preprocesses an image via histogram truncation, removal of blood vessels and artifacts, division of each image into 300×300 µm² FOVs, and homomorphic filtering of each FOV. The second module segments axons from a 2845 cm$^{-1}$ channel as follows. First, each FOV is converted to a binary image using a threshold derived from the mean intensity of that FOV. The image is de-noised via image opening, and remaining objects are dilated, creating a "rough mask" of candidate objects. In parallel, the FOV is also sharpened and converted to binary using a threshold defined by Otsu's method. Image opening is performed and the result is convolved with a Sobel edge kernel, converted to binary using Otsu's thresholding, and opened again. All remaining objects are then sorted by eccentricity (defined as the ratio of the major and minor axes lengths of the bounding ellipse) and area. Those having eccentricity less than 0.85 and size less than 600 pixels are removed. Pixels included in both this mask and the rough intensity mask are counted as axons. The number of perimeter pixels belonging to the resultant objects is summed as the axonal length.

In the third module, nuclear segmentation begins with subtraction of the 2845 cm$^{-1}$ channel from the 2930 cm$^{-1}$ channel, and setting all pixels with intensities less than the FOV mean plus 1.5 standard deviations to zero. Image opening is then conducted with a 5×5 square mask, and the image is converted to binary via Otsu's thresholding. All objects smaller than one half the size of a user-selected "smallest nucleus" are then removed. A watershed algorithm is then used to separate contiguous objects containing multiple local maxima. Objects are then thickened with maintained connectedness, and holes within objects are filled in.

Methods for Analyzing Tissue Samples

The current technology also provides methods for analyzing a tissue sample. The methods include removing a tissue sample, i.e., a biopsy, from a patient using any biopsy device described herein and optically imaging the tissue sample. Imaging the tissue sample can be performed with a modality that is optically sectioning and or with a modality that is based on intrinsic spectroscopy contrast, including but not limited to stimulated Raman scattering (SRS), coherent anti-Stokes Raman scattering (CARS), confocal Raman, confocal reflection, confocal fluorescence, optical coherent tomography (OCT), two-photon excited fluorescence (TPEF), second harmonic generation (SHG), or third harmonic generation (THG).

In certain embodiments, the method further includes performing a secondary analysis of the same biopsy sample including, but not limited to, molecular biology techniques, such as DNA sequencing, RNA sequencing, transcription privileging, micro-array analysis, antibody, fluorescence in situ hybridization (FISH), chromatic immunoprecipitation (ChIP), polymerase chain reaction (PCR) or mass spectroscopy. Therefore, both histological and molecular analysis of the same tissue sample may be performed. The tissue sample could be acquired with a traditional biopsy device and prepared by frozen section, squash or touch preparation for imaging and then removed for secondary analysis. Alternatively, the tissue sample can be removed from the biopsy device by applying positive pressure through the first opening or by removing a portion of the biopsy device. For example, the tissue sample can be automatically split into a container of fixative after imaging is complete.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device comprising:
a body extending from a first end to an opposing second end and defining a collection channel extending from a first opening at the first end to a second opening at the second end, the first opening being in communication with a source of negative pressure, and the collection channel being configured to receive a biological sample from a subject;
a scanner integrated into the body, the scanner being configured to emit light across the collection channel and through the biological sample disposed in the collection channel; and
a detector integrated into the body, the detector being configured to receive light emitted from the scanner and to capture an image of the biological sample.

2. The device according to claim 1, further comprising:
a lens integrated into the body, the lens being configured to focus light emitted from the scanner to the detector.

3. The device according to claim 1, wherein the collection channel is straight.

4. The device according to claim 1, wherein the collection channel has an angled turn.

5. The device according to claim 1, wherein the source of negative pressure is a hospital's vacuum system.

6. The device according to claim 1, wherein the imaging is transmission imaging.

7. The device according to claim 1, wherein the imaging is stimulated Raman scattering (SRS) imaging.

8. The device according to claim 1, wherein the scanner comprises an optical fiber.

9. A system for receiving and imaging a biological sample, the system comprising:
a biopsy device comprising:
a body extending from a first end to an opposing second end and defining a collection channel extending from a first opening at the first end to a second opening at the second end,
a scanner integrated into the body, the scanner being configured to emit light across the collection channel and through the biological sample disposed in the collection channel; and
a detector integrated into the body, the detector being configured to receive lighted emitted from the scanner and to capture an image of the biological sample;
a source of negative pressure operably coupled to the first opening of the biopsy device and configured to provide suction for aspirating a biological sample into the collection channel; and
a screen for displaying the image captured by the detector.

10. The system according to claim 9, wherein the detector is configured to capture stimulated Raman scattering (SRS) images of the biological sample.

11. The system according to claim 9, further comprising:
a computer configured to perform an automated image analysis on the image, the analysis comprising determining a classifier value that identifies the biological sample as being normal tissue or abnormal tissue,
wherein the determining the classifier value comprises quantifying nuclear density, axonal density, a protein:lipid ratio, or a combination thereof from the SRS image.

12. The system according to claim 9, further comprising:
a navigational beacon coupled to the biopsy device,
wherein the navigational beacon provides coordinates corresponding to a location where a biological sample was collected in a subject.

13. A method of analyzing a biological sample, the method comprising:
directing a device to a tissue in a subject, the device comprising:
a body extending from a first end to an opposing second end and defining a collection channel extending from a first opening at the first end to a second opening at the second end, the first opening being in communication with a source of negative pressure;
applying negative pressure through the collection channel of the device; and
aspirating a biological sample of the tissue through the second opening of the collection channel and capturing the portion of the tissue in the collection channel,
wherein the device is configured to:
scan the biological sample in the collection channel with light emitted from a scanner integrated in the body of the device;
detect light transmitted through the biological sample with a detector integrated in the body of the device; and
capture an image of the biological sample.

14. The method according to claim 13, wherein the image is a stimulated Raman scattering (SRS) image.

15. The method according to claim 13, wherein the device is further configured to track a location where the biological sample was collected in the subject.

16. The method according to claim 15, wherein the device is in communication with a computer configured to register the image into a pre-operative dataset at a location where the biological sample was collected, the pre-operative dataset comprising a magnetic resonance imaging (MRI)-based dataset or a pre-operative computed tomography (CT)-based dataset; and to display a merged dataset on a screen, the merged dataset comprising the image of the biological sample registered with the pre-operative dataset.

17. The method according to claim 13, wherein the biological sample comprises brain tissue and the method further comprises:

operating a computer to perform an automated image analysis on the image, the analysis comprising determining a classifier value that identifies the biological sample as being normal brain tissue or abnormal brain tissue, wherein the determining the classifier value comprises quantifying nuclear density, axonal density, a protein:lipid ratio, or a combination thereof from the image.

18. The method according to claim 17, wherein the automated image analysis further comprises classifying abnormal tissue as minimally hypercellular, as an infiltrating tumor, or as a high-density tumor.

19. The method according to claim 17, wherein the computer quantifies nuclear density, axonal density, protein:lipid ratio, or a combination thereof from the image to obtain corresponding values, and compares the corresponding values to predetermined values in an image library.

20. The method according to claim 13, further comprising:

recovering the biological sample from the biopsy device; and performing a secondary analysis on the biological sample, wherein the secondary analysis comprises DNA sequencing, RNA sequencing, transcript profiling, micro-array analysis, antibody analysis, fluorescence in situ hybridization (FISH), chromatin immunoprecipitation (ChIP), polymerase chain reaction (PCR), mass spectroscopy, or a combination thereof.

* * * * *

UNITED STATES PATENT AND TRADEMARK OFFICE
CERTIFICATE OF CORRECTION

| | |
|---|---|
| PATENT NO. | : 11,419,590 B2 |
| APPLICATION NO. | : 16/994327 |
| DATED | : August 23, 2022 |
| INVENTOR(S) | : Daniel Orringer et al. |

It is certified that error appears in the above-identified patent and that said Letters Patent is hereby corrected as shown below:

In the Claims

At Column 38, Claim number 9, Line number 22, delete "lighted" and insert --light--.

Signed and Sealed this
Sixth Day of December, 2022

*Katherine Kelly Vidal*

Katherine Kelly Vidal
*Director of the United States Patent and Trademark Office*